United States Patent
Cai et al.

(10) Patent No.: US 10,874,670 B2
(45) Date of Patent: Dec. 29, 2020

(54) SUBSTITUTED FUSED HETEROAROMATIC COMPOUNDS AS KINASE INHIBITORS AND THE USE THEREOF

(71) Applicant: IMPACT THERAPEUTICS, INC., Shanghai (CN)

(72) Inventors: Suixiong Cai, Shanghai (CN); Ye Edward Tian, Shanghai (CN)

(73) Assignee: IMPACT THERAPEUTICS, INC., Shanghai (CN)

( * ) Notice: Subject to any disclaimer, the term of this patent is extended or adjusted under 35 U.S.C. 154(b) by 0 days.

(21) Appl. No.: 16/476,762

(22) PCT Filed: Jan. 9, 2018

(86) PCT No.: PCT/CN2018/071851
§ 371 (c)(1),
(2) Date: Jul. 9, 2019

(87) PCT Pub. No.: WO2018/127195
PCT Pub. Date: Jul. 12, 2018

(65) Prior Publication Data
US 2019/0358225 A1 Nov. 28, 2019

(30) Foreign Application Priority Data

Jan. 9, 2017 (CN) .......................... 2017 1 0014520

(51) Int. Cl.
| | | |
|---|---|---|
| *C07D 487/04* | (2006.01) | |
| *C07D 471/14* | (2006.01) | |
| *A61K 31/4985* | (2006.01) | |
| *A61K 31/519* | (2006.01) | |
| *A61P 35/00* | (2006.01) | |

(52) U.S. Cl.
CPC ........ *A61K 31/4985* (2013.01); *A61K 31/519* (2013.01); *A61P 35/00* (2018.01); *C07D 471/14* (2013.01); *C07D 487/04* (2013.01)

(58) Field of Classification Search
CPC ................ C07D 487/04; C07D 471/14; A61K 31/4985; A61K 31/519
USPC .......................................................... 546/82
See application file for complete search history.

(56) References Cited

U.S. PATENT DOCUMENTS 9,181,264 B2 * 11/2015 Su .................... A61P 43/00

FOREIGN PATENT DOCUMENTS

| CN | 102399218 A | 4/2012 |
|---|---|---|
| CN | 103080092 A | 5/2013 |
| CN | 106255692 A | 12/2016 |
| WO | WO 2009155527 A2 | 12/2009 |
| WO | WO 2012034526 A1 | 3/2012 |

OTHER PUBLICATIONS

Wagner et al., European Journal of Medicinal Chemistry (2016), 107, 97-108.*
Desplat et al., Journal of Enzyme Inhibition and Medicinal Chemistry, (2008), 23(5), 648-658.*
Vidaillac et al., Journal of Enzyme Inhibition and Medicinal Chemistry, (2007), 22(5), 620-631.*
Wagner; S., et al., "Development of Highly Potent Phosphodiesterase 10A (PDE10A) Inhibitors: Synthesis and in Vitro Evaluation of 1,8-dipyridinyl- and 1-pyridinyl-substituted imidazo[1,5-a]quinoxalines," European Journal of Medicinal Chemistry 107:97-108, Elsevier Masson SAS, Netherlands (2016).
English Translation of International Search Report for International Application No. PCT/CN2018/071851, State Intellectual Property Office of the P.R China, China, dated Apr. 18, 2018.

* cited by examiner

*Primary Examiner* — Niloofar Rahmani
(74) *Attorney, Agent, or Firm* — Sterne Kessler Goldstein & Fox PLLC

(57) ABSTRACT

The disclosure relates to substituted fused heteroaromatic compounds and the use thereof. Specifically, the disclosure provides compounds of the following Formula I:

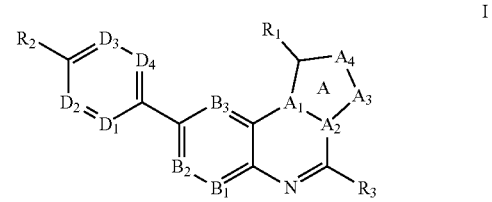

or a pharmaceutically acceptable salt or prodrug thereof, wherein $A_1$-$A_4$, $B_1$-$B_3$, $D_1$-$D_4$ and $R_1$-$R_3$ are defined herein. Compounds having Formula I are kinalse inhibitors. Therefore, compounds of the disclosure may be used to treat clinical conditions caused by DDR functional defects, such as cancer.

19 Claims, No Drawings

SUBSTITUTED FUSED HETEROAROMATIC COMPOUNDS AS KINASE INHIBITORS AND THE USE THEREOF

FIELD OF THE DISCLOSURE

This disclosure is in the field of medicinal chemistry. In particular, the disclosure relates to substituted fused heteroaromatic compounds, and the use of these compounds as kinase inhibitors, including ATM protein kinase inhibitors.

RELATED ART

Mammalian cells encounter many external and internal challenges that cause DNA damage every day, including mutations in DNA bases. These mutations cause changes in cell function, including the occurrence of malignant tumors, even directly cause cell death. Therefore, mammalian cells have evolved a sophisticated DNA damage response (DDR) mechanism to address these challenges. This mechanism detects and repairs DNA damage by short cell cycle pauses to ensure genome stability and cell survival.

The occurrence of DDR and cancer has an inextricable relationship. Scientific research has found that deficiencies in DDR repair mechanisms can lead to cancer at multiple levels, such as base mutations in the DDR gene have been found to cause a variety of cancers, including breast cancer and ovarian cancer in women with mutations in the BRCA1 or BRCA2 gene, which are much higher than in people without mutations. BRCA1 and BRCA2 are important components of DDR to repair DNA double-strand breaks based on homologous recombination. Studies have also found deletions or loss of function of key proteins in DDR cells of various malignant tumors or regulate the cell cycle, including p53, ATM, ATR, BRCA1/2 and so on.

In recent years, with the development of science and understanding of the mechanism of cell DDR, there has been great interest in the development of novel anticancer targeted therapeutic drugs for the mutation and loss of function of DDR constituent proteins. For example, PARP inhibitors can specifically kill cancer cells with BRCA1/2 mutations by inhibiting the single-strand repair mechanism of DNA damage. This mechanism of action is called synthetic lethality.

ATM kinase is one of the important constituent proteins of DDR and belongs to the PI3K related serine/threonine kinase family. ATM kinase gene was cloned when the telangiectasia ataxia syndrome was studied in 1995. ATM gene is located on human chromosome 11q22-23 and is a coding sequence comprising 66 exons and 9168 bases. ATM kinase is a large protein with a molecular weight of approximately 350 kDa. ATM kinase is one of the important components of DDR. ATM kinase is activated when DNA damage causes double-strand breaks. Its function is to achieve cell cycle transition point pause by phosphorylation of downstream proteins, repairing damaged DNA by homologous recombination or entering apoptotic mechanism (Weber and Ryan, 2016).

ATM kinase signal transduction can be roughly divided into two mechanisms: the typical mechanism is activated by DNA double-strand breaks. When DNA double-strand breaks are detected, the ATM kinase is transported to the breaking site and activated. Although the detailed activation mechanism is not well understood, the activation process includes from homodimers into active monomers (Bakkenist et al., 2003), self-phosphorylation of Ser1981 site and other sites, and acetylation. Activated ATM kinase further phosphorylates downstream substrates, including cell cycle checkpoint proteins (such as Chk1 and Chk2), DNA repair proteins (BRCA1 and RAD51), or apoptotic pathway proteins (p53). Studies have shown that there are more than 700 proteins phosphorylated after DNA double-strand breaks (Choi, Kipps and Kurzrock, 2016). In addition, ATM is involved in functions that are not directly related to DNA damage, such as metabolism, stress, etc. These functions are often referred to as atypical mechanisms (Cremona et al., 2013).

The development of new anticancer drugs targeting ATM kinase mainly depends on two considerations. Radiotherapy or cytotoxic chemotherapeutics, such as topoisomerase inhibitors and DNA methylation drugs, etc., which are usually toxic to rapidly differentiated cancer cells based on DNA damage, are greatly reduced in cytotoxicity due to the presence of DDR. Therefore, ATM inhibitors, combined with inhibitors that inhibit the function of DDR constituent proteins, such as PARP inhibitors, can greatly enhance the efficacy of these drugs. Studies by Gilardini Montani M S et al. (J Exp Clin Cancer Res, 2013, 32:95) have shown that reducing ATM expression could enhance the sensitivity of breast cancer cells to PARP inhibitors, which provided a theoretical basis for the possibility of combination of ATM inhibitors and PARP inhibitors in the treatment of breast cancer. In addition, Kubota E et al. (Cell Cycle, 2014, 13 (13): 2129-2137) found that the expression of ATM protein in gastric cancer cells was significantly correlated with the sensitivity of PARP inhibitor olaparib. ATM inhibitors enhance the sensitivity of p53-inactivated gastric cancer cells to olaparib. Therefore, the combined use of ATM inhibitors and PARP inhibitors may be used to treat gastric cancer. In addition, for cancer cells with DDR deficiency, ATM kinase inhibitors can be used alone by synthesizing lethal mechanism and targeted anticancer drugs can be developed for specific patients, which have the characteristics of good efficacy and low toxicity.

WO2012034526 disclosed fused heteroaromatic compounds as PI3K kinase inhibitors, wherein, $A^1$ is N or CH; $A^4$ and $A^5$ are independently N or $CR^2$, $R^2$ is independently selected from H, alkyl, alkenyl, alkynyl, aryl and so on; $A^2$ and $A^3$, together with B ring form a 5-membered heteroaryl or heterocycle containing 1 to 4 heteroatoms selected from N, O, and S; === is a single bond or a double bond; $R^1$ is heteroaryl.

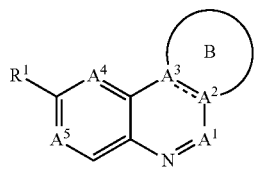

WO2015170081 disclosed imidazolidoquinolones as ATM kinase inhibitors, wherein, Q is cyclobutyl or cyclopentyl or oxetanyl, tetrahydrofuranyl or oxanyl; $R^1$ is methyl; $R^2$ is H or methyl; or $R^1$ and $R^2$ together form an azetidinyl, pyrrolidinyl or piperidinyl; $R^3$ is H or fluoro; $R^4$ is H or methyl; and $R^5$ is H or fluoro.

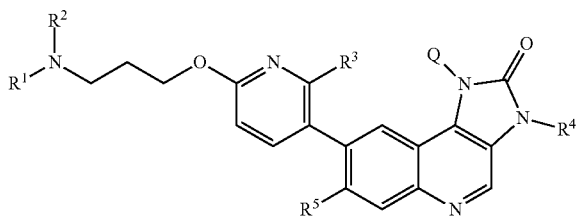

Degorce S L et al. (J Med Chem, 2016, 59: 6281-6292) reported a series of 3-quinolinformamides as ATM kinase inhibitors, and observed good efficacy of ATM kinase inhibitors combined with irinotecan in animal model.

SUMMARY OF THE DISCLOSURE

The disclosure provides novel substituted fused heteroaromatic compounds, as represented in Formulae I, II and III as kinase inhibitors, especially ATM kinase inhibitors.

The present disclosure also provides pharmaceutical compositions comprising a compound of Formula I, II or III in an effective amount for the treatment of cancer.

In a concrete embodiment, the pharmaceutical composition useful for the treatment of cancer may also contain one or more pharmaceutically acceptable carriers or diluents.

In a concrete embodiment, the pharmaceutical composition useful for the treatment of cancer may also contain at least one known anticancer drugs or its pharmaceutically acceptable salts.

The disclosure is also directed to methods for the preparation of novel compounds of Formulae I, II and III.

DETAILED DESCRIPTION OF THE DISCLOSURE

The disclosure finds novel substituted fused heteroaromatic compounds as kinase inhibitors, especially ATM kinase inhibitors, as represented in Formula I.

It should be understood that the characteristics of the embodiments described herein can be arbitrarily combined to form the technical solution of this disclosure; The definitions of each group herein shall apply to any of the embodiments described herein. For example, the definitions of substituents for alkyl groups herein shall apply to any of the embodiments described herein unless the substituents for alkyl groups are clearly defined in the embodiment.

Specifically, compounds of the present disclosure are represented by Formula I:

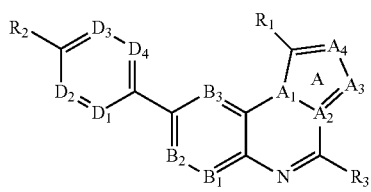

I or pharmaceutically acceptable salts or prodrugs thereof, wherein:

$A_1$ and $A_2$ each are independently C or N;
$A_3$ and $A_4$ each are independently N, O, S, or CR'; and
A ring including $A_1$-$A_4$ is an optionally substituted 5-member heteroaryl containing 1-3 heteroatoms;
$B_1$-$B_3$ each are independently N or CR'';
$D_1$-$D_4$ each are independently N or CR''';
$R_1$ is optionally substituted alkyl, alkoxy, amino, carbocyclic group, heterocyclic group, aryl or heteroaryl;
$R_2$ is H, optionally alkoxy, amino, carbocyclic group, heterocyclic group, aryl or heteroaryl;
R', R'', R''' and $R_3$ each independently are H, halo, optionally substituted amino, optionally substituted alkoxy, optionally substituted $C_{1-10}$ alkyl (e.g. haloalkyl, hydroxyalkyl, aminoalkyl, carboxyalkyl), alkenyl, alkynyl, nitro, cyano, acylamido, hydroxy, thiol, acyloxy, azido, carboxy, ethylenedioxo, hydroxyacylamido or optionally substituted alkylthio.

In one or more embodiment, $A_1$ in compound of Formula I is N. In one or more embodiment, $A_2$ in compound of Formula I is C.

In one or more of the foregoing embodiments, in compound of Formula I, $A_1$ is N, $A_2$ is C.

In one or more of the foregoing embodiments, in compound of Formula I, $A_3$ and $A_4$ are each independently N.

In one or more of the foregoing embodiments, in compound of Formula I, ring including $A_1$-$A_4$ is triazolyl ring, imidazolyl ring or pyrrolyl ring.

In one or more of the foregoing embodiments, in compound of Formula I, $B_1$ is CR'', preferably, $B_1$ is CH. In one or more embodiments, in compound of Formula I, $R_3$ is H. In one or more embodiments, in compound of Formula I, R' is H.

In one or more of the foregoing embodiments, in compound of Formula I, $B_1$ is CH, R' and $R_3$ are H. In one or more embodiments, $B_2$ and $B_3$ each independently are CH or N.

In one or more of the foregoing embodiments, in compound of Formula I, $B_3$ is CH.

In one or more of the foregoing embodiments, in compound of Formula I, $B_3$ is CH, $B_1$ and $B_2$ is CH.

In one or more of the foregoing embodiments, in compound of Formula I, $B_3$ is N.

In one or more of the foregoing embodiments, in compound of Formula I, $B_3$ is N, $B_1$ and $B_2$ are CH.

In one or more of the foregoing embodiments, in compound of Formula I, $A_1$ is N, $A_2$ is C, $B_1$ is CH, R' and $R_3$ are H.

In one or more of the foregoing embodiments, in compound of Formula I, $A_1$ is N, $A_2$ is C, $B_1$-$B_3$ are CH, R' and $R_3$ are H.

In one or more of the foregoing embodiments, in compound of Formula I, $A_1$ is N, $A_2$ is C, $B_1$ and $B_2$ are CH, $B_3$ is N, R' and $R_3$ are H.

In one or more of the foregoing embodiments, in compound of Formula I, the ring including $B_1$-$B_3$ is phenyl or pyridyl. Preferably, the ring including $B_1$-$B_3$ is phenyl or $B_3$ is pyridyl including N.

In one or more of the foregoing embodiments, in compound of Formula I, the 6-member ring including $A_1$ and $A_2$ is pyrazinyl or pyrimidinyl, preferably pyrazinyl.

In one or more of the foregoing embodiments, in compound of Formula I, the A ring including $A_1$-$A_4$, the 6-member ring including $A_1$-$A_2$ and the ring including $B_1$-$B_3$ are fused to form pyrido[2,3-e][1,2,4]triazolo[4,3-a]pyrazinyl, pyrido[3,4-e][1,2,4]triazolo[4,3-a]pyrazinyl, pyrido[3,2-e][1,2,4]triazolo[4,3-a]pyrazinyl, [1,2,4]triazolo[4,3-a]quinoxalinyl, imidazo[1,5-c]quinazolinyl, imidazo[1,5-a]quinoxalinyl, imidazo[1,2-a]quinoxalinyl, or pyrrolo[1,2-a]quinoxalinyl.

In one or more of the foregoing embodiments, in compound of Formula I, the substituent on $R_1$ is selected from the group consisting of $C_{1-6}$ alkyl, heterocyclic, aryl, heteroaryl and —$NR_9R_{10}$ groups, wherein the number of the substituents is 1-4, and $R_9$ and $R_{10}$ are independently selected from hydrogen and $C_{1-6}$ alkyl groups. In certain embodiments, $R_1$ is an optionally substituted alkyl group, heterocyclic group, aryl group or heteroaryl group, wherein the substituent on the alkyl group may be one heterocyclic group such as tetrahydrofuryl, tetrahydropyranyl, pyranyl, piperidyl, piperazinyl, pyrrolidinyl, imidazolidinyl, imidazolinyl, dihydroindolyl, dihydroisoindolyl, morpholinyl, pyrazolidinyl, pyrazolinyl and the like; the substituents on the heterocyclic group, aryl group and heteroaryl group may be 1-4 substituents selected from $C_{1-6}$ alkyl and —$NR_9R_{10}$ groups.

In one or more of the foregoing embodiments, in compound of Formula I, $R_1$ is selected from the group consisting of tetrahydropyranyl that is not substituted or optionally substituted with 1-4 $C_{1-6}$ alkyl groups, piperidyl that is not substituted or optionally substituted with —$NR_9R_{10}$ or 1-4 $C_{1-6}$ alkyl groups, morpholinyl that is not substituted or optionally substituted with 1-4 $C_{1-6}$ alkyl groups, imidazolyl, piperazinyl that is optionally substituted with 1-4 $C_{1-6}$ alkyl groups, $C_{1-6}$ alkyl that is optionally substituted with a heterocyclic group (tetrahydrofuryl, tetrahydropyranyl, pyranyl, piperidyl, piperazinyl, pyrrolidinyl, imidazolidinyl, imidazolinyl, dihydroindolyl, dihydroisoindolyl, morpholinyl, pyrazolidinyl and pyrazolidinyl, etc); wherein $R_9$ and $R_{10}$ are independently selected from hydrogen and $C_{1-6}$ alkyl groups. In certain embodiments, in compound of Formula I, $R_1$ is selected from the group consisting of tetrahydropyranyl that is not substituted or optionally substituted with 1-2 $C_{1-4}$ alkyl groups, piperidyl that is not substituted or optionally substituted with —$NR_9R_{10}$ or 1-2 $C_{1-4}$ alkyl groups, morpholinyl that is not substituted or optionally substituted with 1-2 $C_{1-4}$ alkyl groups, and piperazinyl that is optionally substituted with 1-3 $C_{1-4}$ alkyl groups. Preferred $R_1$ is selected from optionally substituted heterocyclic groups, including:

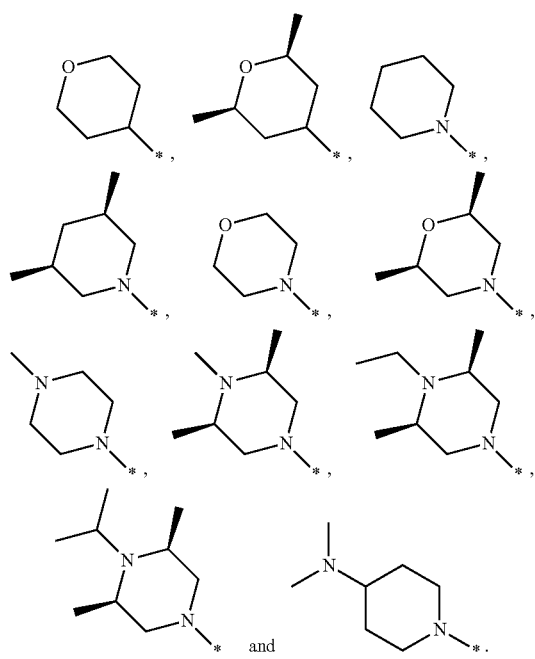

More preferably, $R_1$ is selected from:

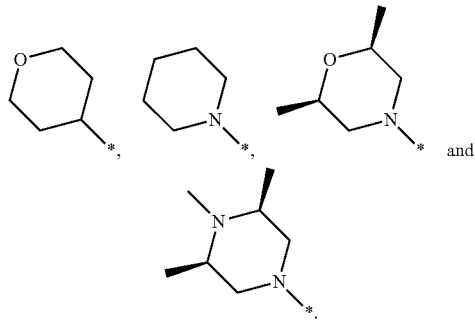

In one or more of the foregoing embodiments, in compound of Formula I, the ring comprising $D_1$-$D_4$ is optionally substituted pyridinyl, optionally substituted phenyl, optionally substituted pyrimidinyl, or optionally substituted pyrazinyl. Preferably, the ring comprising $D_r$ $D_4$ in compound of Formula I is optionally substituted phenyl. In some embodiment, the substituents on the ring comprising $D_1$-$D_4$ contain R''' in addition to $R_2$.

In one or more of the foregoing embodiments, in compound of Formula I, $D_1$ is CH, $D_2$ is N, $D_3$ is N, and $D_4$ is CH; in some embodiments, $D_1$ is N, $D_2$ is CH, $D_3$ is CH, $D_4$ is CH; in some embodiments, $D_1$ is CH, $D_2$ is N, $D_3$ is CH, $D_4$ is CH; in some embodiments, $D_1$ is CR''', $D_2$ is CR''', $D_3$ is CR''', $D_4$ is CH; in some embodiments, $D_1$ is CH, $D_2$ is CR''', $D_3$ is CR''', $D_4$ is CH; in some embodiments, $D_1$ is CH, $D_2$ is CR''', $D_3$ is CH, $D_4$ is CH; in some embodiments, $D_1$ is CR''', $D_2$ is CR''', $D_3$ is CR''', $D_4$ is CR'''; $D_1$ is CR''', $D_2$ is CR''', $D_3$ is CH, $D_4$ is CH, wherein preferably, R''' independently is H, halo, $C_{1-4}$ alkyl and halo $C_{1-4}$ alkyl. More preferably, R''' independently is halo and halo $C_{1-4}$ alkyl.

In one or more of the foregoing embodiments, in compound of Formula I, the substituent on $R_2$ may be selected from the group consisting of —$NR_9R_{10}$, $C_{1-4}$ alkyl, and $C_{1-6}$ alkyl substituted with —$NR_9R_{10}$, wherein the number of the substituents is 1-4, and $R_9$ and $R_{10}$ are independently selected from hydrogen and $C_{1-6}$ alkyl groups.

In one or more of the foregoing embodiments, in compound of Formula I, $R_2$ is selected from the group consisting of hydrogen, —$NR_9R_{10}$, $C_{1-6}$ alkyl optionally substituted with —$NR_9R_{10}$, $C_{1-6}$ alkoxy optionally substituted with —$NR_9R_{10}$, $C_{1-6}$ alkyl-NH— optionally substituted with —$NR_9R_{10}$, piperazinyl optionally substituted with 1-3 $C_{1-4}$ alkyl groups, piperidyl optionally substituted with —$NR_9R_{10}$ or —$NR_9R_{10}$-substituted $C_{1-6}$ alkyl, and $C_{3-8}$ cycloalkyl optionally substituted with —$NR_9R_{10}$, $R_9$ and $R_{10}$ are independently selected from hydrogen or $C_{1-6}$ alkyl groups. In certain embodiments, $R_2$ is selected from the group consisting of $C_{3-8}$ cycloalkyl optionally substituted with —$NR_9R_{10}$, piperidyl optionally substituted with —$NR_9R_{10}$ or —$NR_9R_{10}$-substituted $C_{1-6}$ alkyl, piperazinyl optionally substituted with 1-3 $C_{1-4}$ alkyl groups, and $C_{1-6}$ alkoxy optionally substituted with —$NR_9R_{10}$. Preferred $R_2$ includes:

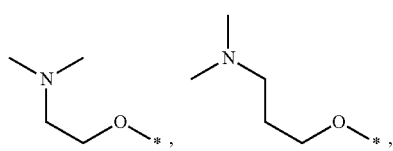

-continued

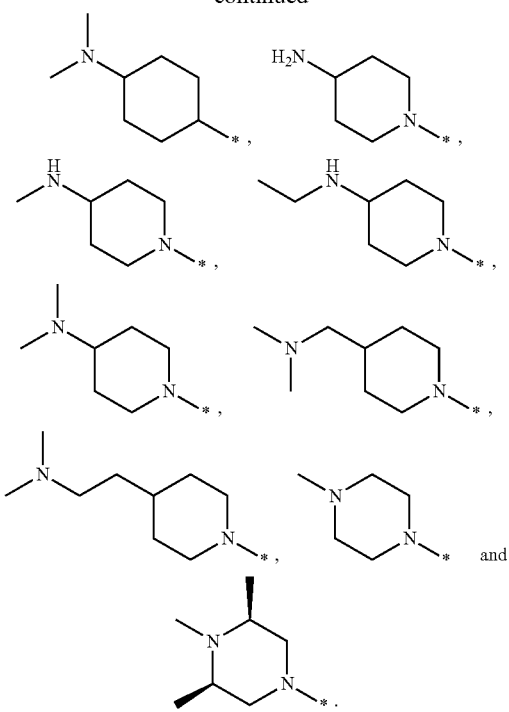

More preferably R₂ is selected from:

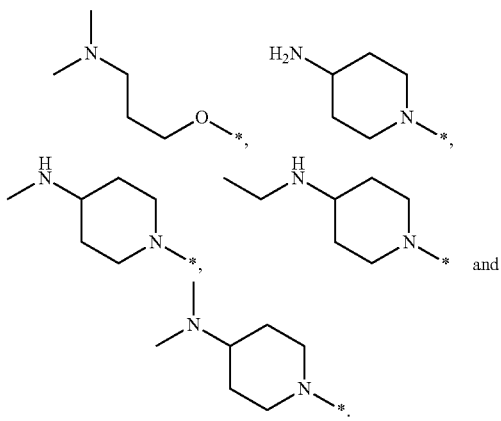

One group of preferred compounds of the present disclosure are represented by Formula II:

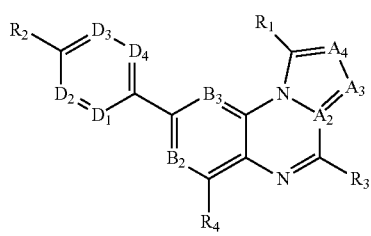

II or pharmaceutically acceptable salts or prodrugs thereof, wherein:

$A_2$-$A_4$, $B_2$-$B_3$, $D_1$-$D_4$ and $R_1$-$R_3$ are defined as in Formula I;

$R_4$ independently is H, halo, optionally substituted amino, optionally substituted alkoxy, optionally substituted $C_{1-10}$ alkyl (e.g. haloalkyl, hydroxyalkyl, aminoalkyl, carboxyalkyl), alkenyl, alkynyl, nitro, cyano, acylamido, hydroxy, thiol, acyloxy, azido, carboxy, ethylenedioxo, hydroxyacylamido or optionally substituted alkylthiol.

In one or more of the foregoing embodiments of compound of Formula II, the said $A_2$-$A_4$, $B_2$-$B_3$, $D_1$-$D_4$ and $R_1$-$R_3$ are described in any embodiment of Formula I.

In one or more of the foregoing embodiments, in compound of Formula II, $R_3$ and $R_4$ are H.

In one or more of the foregoing embodiments, in compound of Formula II, $A_2$ is C.

In one or more of the foregoing embodiments, in compound of Formula II, $A_3$ and $A_4$ each are N.

In one or more of the foregoing embodiments, in compound of Formula II, the ring including $A_2$-$A_4$ is a triazolyl, imidazolyl or pyrrolyl ring.

In one or more of the foregoing embodiments, in compound of Formula II, R' is H.

In one or more of the foregoing embodiments, in compound of Formula II, $A_2$ is C, R' and $R_3$ are H.

In one or more of the foregoing embodiments, in compound of Formula II, $B_2$ and $B_3$ each independently are CH or N.

In one or more of the foregoing embodiments, in compound of Formula II, the ring including $B_2$-$B_3$ is a phenyl or pyridyl ring. Preferably, the ring including $B_2$-$B_3$ is a phenyl ring or a pyridyl ring in which $B_3$ is N.

In one or more of the foregoing embodiments, in compound of Formula II, the 6-member ring including $A_2$ is a pyrazinyl ring.

In one or more of the foregoing embodiments, in compound of Formula II, the ring including $A_2$-$A_4$, the 6-member ring including $A_2$ and the ring including $B_2$-$B_3$ are fused to form pyrido[2,3-e][1,2,4]triazolo[4,3-a]pyrazinyl, pyrido [3,4-e][1,2,4]triazolo[4,3-a]pyrazinyl, pyrido[3,2-e][1,2,4]triazolo[4,3-a]pyrazinyl, [1,2,4]triazolo[4,3-a]quinoxalinyl, imidazo[1,5-a]quinoxalinyl, imidazo[1,2-a]quinoxalinyl or pyrrolo[1,2-a]quinoxalinyl.

In one or more of the foregoing embodiments, in compound of Formula II, $R_1$ is selected from the group consisting of tetrahydropyranyl that is not substituted or optionally substituted with 1-4 $C_{1-6}$ alkyl groups, piperidyl that is not substituted or optionally substituted with —$NR_9R_{10}$ or 1-4 $C_{1-6}$ alkyl groups, morpholinyl that is not substituted or optionally substituted with 1-4 $C_{1-6}$ alkyl groups, imidazolyl, piperazinyl that is optionally substituted with 1-4 $C_{1-6}$ alkyl groups, $C_{1-6}$ alkyl that is optionally substituted with a heterocyclic group (for example, tetrahydrofuryl, tetrahydropyranyl, pyranyl, piperidyl, piperazinyl, pyrrolidinyl, imidazolidinyl, imidazolinyl, dihydroindolyl, dihydroisoindolyl, morpholinyl, pyrazolidinyl and pyrazolidinyl, etc); wherein $R_9$ and $R_{10}$ are independently selected from hydrogen and $C_{1-6}$ alkyl groups. In certain embodiments, in compound of Formula I, $R_1$ is selected from the group consisting of tetrahydropyranyl that is not substituted or optionally substituted with 1-2 $C_{1-4}$ alkyl groups, piperidyl that is not substituted or optionally substituted with —$NR_9R_{10}$ or 1-2 $C_{1-6}$ alkyl groups, morpholinyl that is not substituted or optionally substituted with 1-2 $C_{1-4}$ alkyl groups, and piperazinyl that is optionally substituted with 1-3 $C_{1-4}$ alkyl groups. Preferred $R_1$ is selected from optionally substituted heterocyclic groups, including:

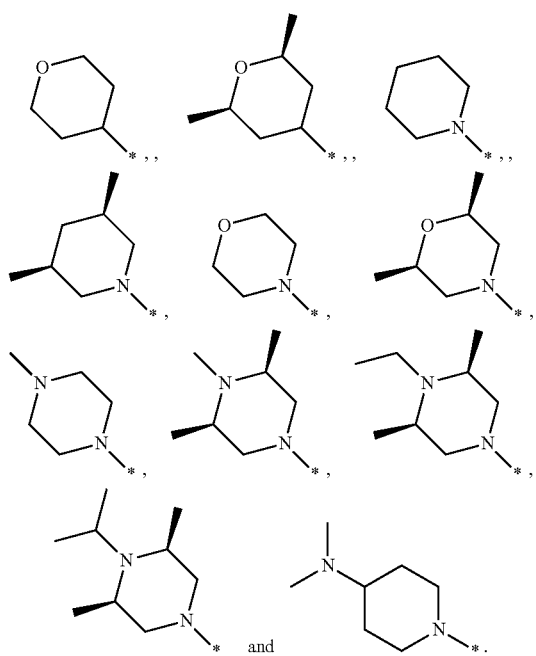

More preferably, R₁ is selected from:

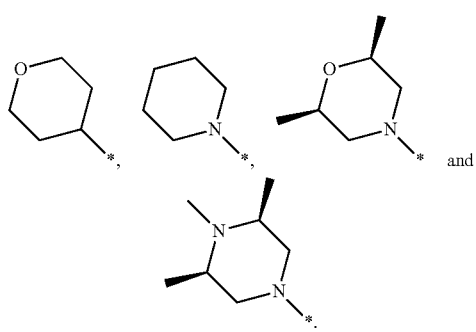

In one or more of the foregoing embodiments, the ring including $D_1$-$D_4$ in compound of Formula II is an optionally substituted pyridyl ring, an optionally substituted phenyl ring, an optionally substituted pyrimidinyl ring or an optionally substituted pyrazinyl ring. Preferably, the ring including $D_1$-$D_4$ in compound of Formula I is an optionally substituted phenyl ring. More preferably, the ring including $D_1$-$D_4$ is a phenyl ring in which $D_1$ and/or $D_2$ are substituted with R', or a phenyl ring in which $D_2$ and/or $D_3$ are substituted with R'. Preferably, R''' is selected from the group consisting of H, halo, $C_{1-4}$ alkyl and halo $C_{1-4}$ alkyl. More preferably, R''' is selected from the group consisting of halo and halo $C_{1-4}$ alkyl.

In one or more of the foregoing embodiments, in compound of Formula II, $R_2$ is selected from the group consisting of hydrogen, —$NR_9R_{10}$, $C_{1-6}$ alkyl optionally substituted with —$NR_9R_{10}$, $C_{1-6}$ alkoxy optionally substituted with —$NR_9R_{10}$, $C_{1-6}$ alkyl-NH— optionally substituted with —$NR_9R_{10}$, piperazinyl optionally substituted with 1-3 $C_{1-4}$ alkyl groups, piperidyl optionally substituted with —$NR_9R_{10}$, and $C_{3-8}$ cycloalkyl optionally substituted with —$NR_9R_{10}$, wherein $R_9$ and $R_{10}$ are independently selected from the group consisting of hydrogen and $C_{1-6}$ alkyl. In certain embodiments, $R_2$ is selected from the group consisting of $C_{3-8}$ cycloalkyl optionally substituted with —$NR_9R_{10}$, piperidyl optionally substituted with —$NR_9R_{10}$ or —$NR_9R_{10}$-substituted $C_{1-6}$ alkyl, piperazinyl optionally substituted with 1-3 $C_{1-4}$ alkyl groups, and $C_{1-6}$ alkoxy optionally substituted with —$NR_9R_{10}$. Preferred $R_2$ includes:

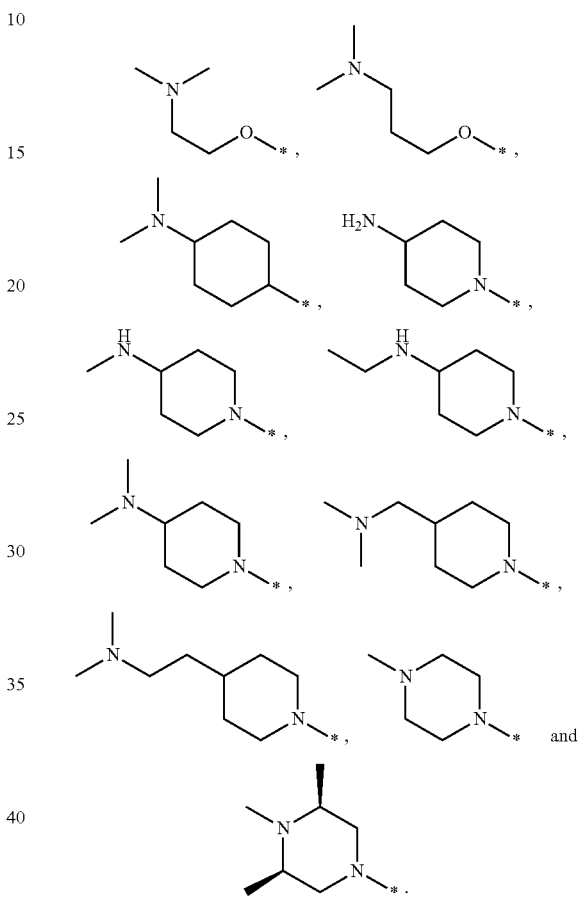

More preferably, $R_2$ is selected from:

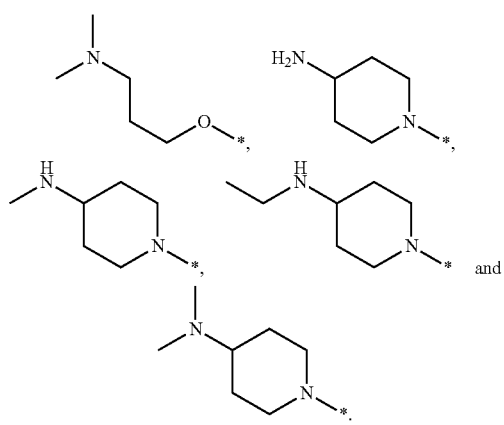

One group of preferred compounds of the present disclosure are represented by Formula IIIa or IIIb (Formula III):

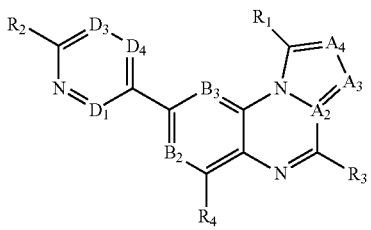

(IIIa)

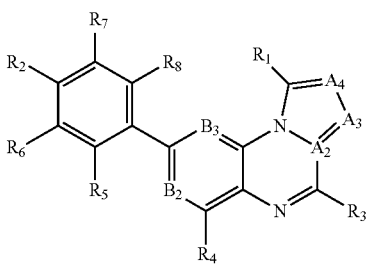

(IIIb)

wherein, $A_2$-$A_4$, $B_2$-$B_3$, $D_1$, $D_3$-$D_4$ and $R_1$-$R_4$ are defined as in Formulae I and II;

in Formula IIIb, $R_5$-$R_8$ are independently hydrogen, halo, optionally substituted amino, optionally substituted alkoxy, optionally substituted $C_{1-10}$ alkyl (e.g. haloalkyl, hydroxyalkyl, aminoalkyl, carboxyalkyl), alkenyl, alkynyl, nitro, cyano, acylamido, hydroxy, thiol, acyloxy, azido, carboxy, ethylenedioxo, hydroxyacylamido or optionally substituted alkylthiol.

In one or more embodiments of compounds of Formulae IIIa and IIIb, the said $A_2$-$A_4$, $B_2$-$B_3$, $D_1$, $D_3$-$D_4$ and $R_1$-$R_3$ are described in any embodiment of Formula I or II.

In one or more of the foregoing embodiments, in compound of Formula IIIa, $R_3$ and $R_4$ are H. In one or more of the foregoing embodiments, in compound of Formula IIIb, $R_5$-$R_8$ are H.

In one or more of the foregoing embodiments, in compound of Formula IIIb, $R_5$ and $R_6$ are independently H, halo, $C_{1-4}$ alkyl or halo $C_{1-4}$ alkyl.

In one or more of the foregoing embodiments, in compound of Formula IIIb, $R_5$ and $R_6$ are independently halo or halo $C_{1-4}$ alkyl.

In one or more of the foregoing embodiments, in compound of Formula IIIb, $R_6$ and $R_7$ are independently H, halo, $C_{1-4}$ alkyl or halo $C_{1-4}$ alkyl.

In one or more of the foregoing embodiments, in compound of Formula IIIa or IIIb, $A_2$ is C.

In one or more of the foregoing embodiments, in compound of Formula IIIa or IIIb, $A_3$ and $A_4$ each are N.

In one or more of the foregoing embodiments, in compound of Formula IIIa or IIIb, the ring including $A_2$-$A_4$ is a triazolyl ring, an imidazolyl ring or a pyrrolyl ring.

In one or more of the foregoing embodiments, in compound of Formula IIIa or IIIb, R' is H.

In one or more of the foregoing embodiments, in compound of Formula IIIa or IIIb, $A_2$ is C, and R' and $R_3$ are H.

In one or more of the foregoing embodiments, in compound of Formula IIIa or IIIb, the ring including $B_2$-$B_3$ is a phenyl ring or a pyridyl ring. Preferably, the said ring including $B_2$-$B_3$ is a phenyl ring, or a pyridyl ring in which $B_3$ is N.

In one or more of the foregoing embodiments, in compound of Formula IIIa or IIIb, the 6-member ring including $A_2$ is a pyrazinyl ring.

In one or more of the foregoing embodiments, in compound of Formula IIIa or IIIb, the ring including $A_2$-$A_4$, the 6-member ring including $A_2$ and the ring including $B_2$-$B_3$ are fused to form pyrido[2,3-e][1,2,4]triazolo[4,3-a]pyrazinyl, pyrido[3,4-e][1,2,4]triazolo[4,3-a]pyrazinyl, pyrido[3,2-e][1,2,4]triazolo[4,3-a]pyrazinyl, [1,2,4]triazolo[4,3-a]quinoxalinyl, imidazo[1,5-a]quinoxalinyl, imidazo[1,2-a]quinoxalinyl or pyrrolo[1,2-a]quinoxalinyl. In preferred embodiments, the ring including $A_2$-$A_4$, the 6-member ring including $A_2$ and the ring including $B_2$-$B_3$ are fused to form pyrido[2,3-e][1,2,4]triazolo[4,3-a]pyrazinyl, [1,2,4]triazolo[4,3-a]quinoxalinyl, pyrido[3,4-e][1,2,4]triazolo[4,3-a]pyrazinyl or pyrido[3,2-e][1,2,4]triazolo[4,3-a]pyrazinyl.

In one or more of the foregoing embodiments, in compound of Formula IIIa or IIIb, $R_1$ is selected from the group consisting of tetrahydropyranyl that is not substituted or optionally substituted with 1-4 $C_{1-6}$ alkyl groups, piperidyl that is not substituted or optionally substituted with —$NR_9R_{10}$ or 1-4 $C_{1-6}$ alkyl groups, morpholinyl that is not substituted or optionally substituted with 1-4 $C_{1-6}$ alkyl groups, imidazolyl, piperazinyl that is optionally substituted with 1-4 $C_{1-6}$ alkyl groups, and $C_{1-6}$ alkyl that is optionally substituted with a heterocyclic group (for example, tetrahydrofuryl, tetrahydropyranyl, pyranyl, piperidyl, piperazinyl, pyrrolidinyl, imidazolidinyl, imidazolinyl, dihydroindolyl, dihydroisoindolyl, morpholinyl, pyrazolidinyl and pyrazolidinyl, etc); wherein $R_9$ and $R_{10}$ are independently selected from hydrogen and $C_{1-6}$ alkyl groups. In certain embodiments, in compound of Formula I, $R_1$ is selected from the group consisting of tetrahydropyranyl that is not substituted or optionally substituted with 1-2 $C_{1-4}$ alkyl groups, piperidyl that is not substituted or optionally substituted with —$NR_9R_{10}$ or 1-2 $C_{1-4}$ alkyl groups, and piperazinyl that is optionally substituted with 1-3 $C_{1-4}$ alkyl groups. Preferred $R_1$ is selected from optionally substituted heterocyclic groups, including:

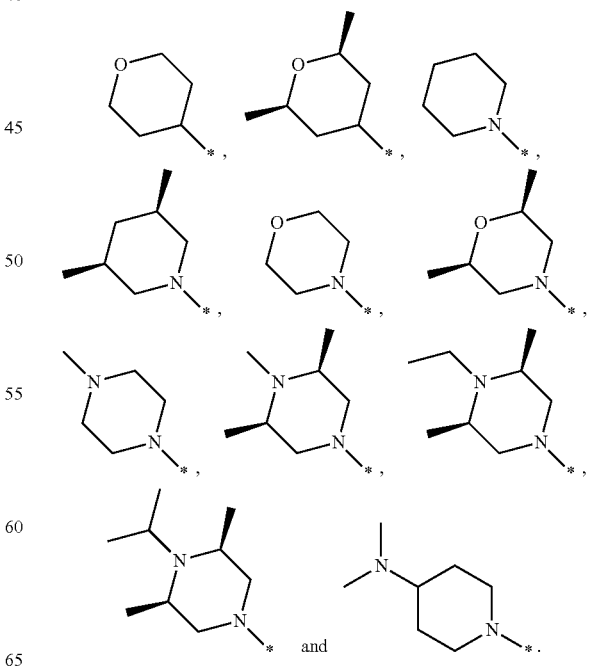

More preferably, $R_1$ is selected from:

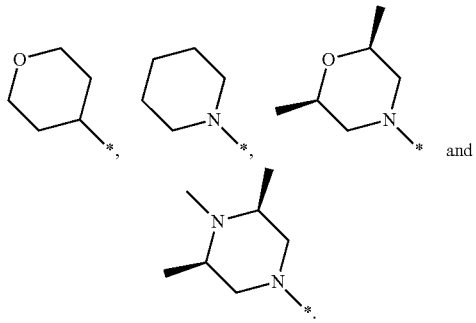

In one or more of the foregoing embodiments, in compound of Formula IIIa, the ring including $D_1$-$D_4$ is an optionally substituted pyridyl ring, an optionally substituted pyrimidinyl ring or an optionally pyrazinyl ring. It should be understood that the substituents on the ring including $D_1$-$D_4$ in the present disclosure may further include R''' in addition to $R_2$. Preferably, R''' is selected from the group consisting of halo, $C_{1-4}$ alkyl and halo $C_{1-4}$ alkyl.

In one or more of the foregoing embodiments, in compound of Formula IIIa or IIIb, $R_2$ is selected from the group consisting of hydrogen, —$NR_9R_{10}$, $C_{1-6}$ alkyl optionally substituted with —$NR_9R_{10}$, $C_{1-6}$ alkoxy optionally substituted with —$NR_9R_{10}$, $C_{1-6}$ alkyl-NH— optionally substituted with —$NR_9R_{10}$, $C_{1-6}$ alkyl-$NHR_9$— optionally substituted with —$NR_9R_{10}$, piperazinyl optionally substituted with 1-3 $C_{1-4}$ alkyl groups, piperidyl optionally substituted with —$NR_9R_{10}$, and $C_{3-8}$ cycloalkyl optionally substituted with —$NR_9R_{10}$, wherein $R_9$ and $R_{10}$ are independently selected from the group consisting of hydrogen and $C_{1-6}$ alkyl. In certain embodiments, $R_2$ is selected from the group consisting of $C_{3-8}$ cycloalkyl optionally substituted with —$NR_9R_{10}$, piperidyl optionally substituted with —$NR_9R_{10}$ or —$NR_9R_{10}$-substituted $C_{1-6}$ alkyl, piperazinyl optionally substituted with 1-3 $C_{1-4}$ alkyl groups, and $C_{1-6}$ alkoxy optionally substituted with —$NR_9R_{10}$. Preferred $R_2$ includes:

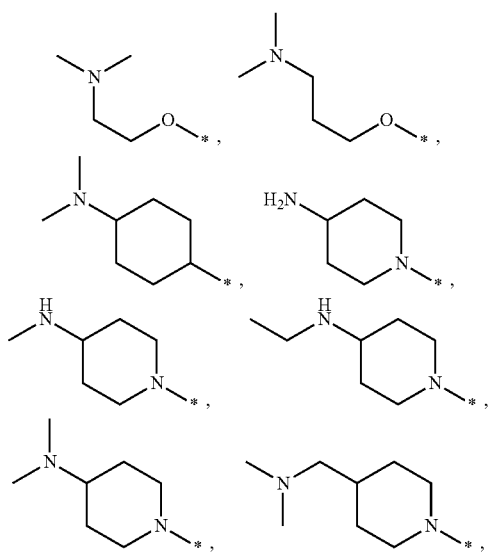

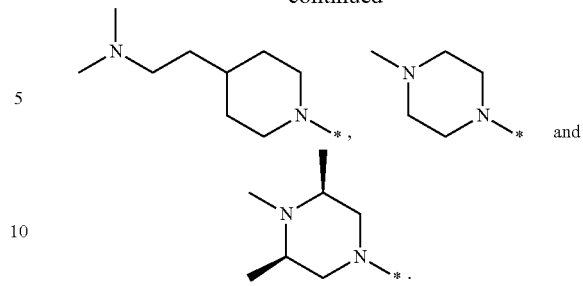

More preferably, $R_2$ is selected from:

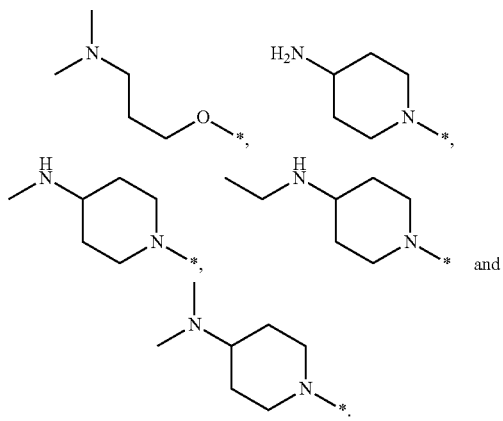

In one or more of the foregoing embodiments, in Formulae I, II, IIa and IIIb, the substituents on the A ring are selected from one or more of the said heteroaryl substituents in the present disclosure.

In one or more of the foregoing embodiments, in Formulae I, II, IIa and IIIb, the said alkyl, alkoxy, amino, carbocyclic group, heterocyclic group, aryl or heteroaryl groups for $R_1$ may be selected from one or more of the alkyl, alkoxy, amino, carbocyclic group, heterocyclic group, aryl or heteroaryl substituents described in the present disclosure.

In one or more of the foregoing embodiments, in Formulae I, II, IIIa and IIIb, the said alkoxy, amino, carbocyclic group, heterocyclic group, aryl or heteroaryl groups for $R_2$ may be selected from one or more of the alkoxy, amino, carbocyclic group, heterocyclic group, aryl or heteroaryl substituents described in the present disclosure.

In one or more of the foregoing embodiments, in Formulae I, II, IIIa and IIIb, the said optionally substituted amino, optionally substituted alkoxy, optionally substituted $C_{1-10}$ alkyl and optionally substituted alkylthio substituents for R', R'', R''' and $R_3$ are selected from one or more of the amino, alkoxy, alkyl and alkylthio substituents described in the present disclosure.

In one or more of the foregoing embodiments, in Formula IIIb, the said optionally substituted amino, optionally substituted alkoxy, optionally substituted $C_{1-10}$ alkyl and optionally substituted alkylthio substituents for $R_5$-$R_8$ are selected from one or more of the amino, alkoxy, $C_{1-10}$ alkyl and alkylthio substituents described in the present disclosure.

In one or more of the foregoing embodiments, in Formula III, an exemplary preferred compound is compound of Formula IIIb.

In one or more of the foregoing embodiments, an exemplary preferred compound is compound of Formula IIIb, wherein $A_2$ is C; $A_3$ and $A_4$ are N; $B_2$ is CH; $B_3$ is N or CH; $R_6$ is haloalkyl or halo; $R_5$, $R_7$ and $R_8$ are H or halo; $R_1$ is an optionally substituted heterocyclic group; $R_2$ is an optionally substituted heterocyclic group or $C_{1-6}$ alkoxy substituted with —$NR_9R_{10}$, wherein $R_9$ and $R_{10}$ are independently selected from hydrogen and $C_{1-6}$ alkyl. More preferably, $B_3$ is N or CH; $R_6$ is $CF_3$, F, Br or Cl; $R_5$, $R_7$ and $R_8$ are H or halo; $R_2$ is the said optionally substituted heterocyclic group or $C_{1-6}$ alkoxy substituted with —$NR_9R_{10}$.

In one or more of the foregoing embodiments, preferred compounds of Formulae I, II, IIIa and IIIb include, without limitation:

N,N-dimethyl-3-((5-(1-(tetrahydro-2H-pyran-4-yl)pyrido[2,3-e][1,2,4]triazolo[4,3-a]pyrazin-8-yl)pyridin-2-yl)oxy)propan-1-amine (Example 1);

N,N-dimethyl-3-(4-(1-(tetrahydro-2H-pyran-4-yl)pyrido[2,3-e][1,2,4]triazolo[4,3-a]pyrazin-8-yl)phenoxy)propan-1-amine (Example 2);

N,N-dimethyl-3-((5-(1-(tetrahydro-2H-pyran-4-yl)-[1,2,4]triazolo[4,3-a]quinoxalin-8-yl)pyridin-2-yl)oxy)propan-1-amine (Example 3);

N,N-dimethyl-3-(4-(1-(tetrahydro-2H-pyran-4-yl)-[1,2,4]triazolo[4,3-a]quinoxalin-8-yl)phenoxy)propan-1-amine (Example 4);

N,N-dimethyl-3-((6-(1-(tetrahydro-2H-pyran-4-yl)-[1,2,4]triazolo[4,3-a]quinoxalin-8-yl)pyridin-3-yl)oxy)propan-1-amine (Example 5);

N,N-dimethyl-3-((5-(1-(tetrahydro-2H-pyran-4-yl)-[1,2,4]triazolo[4,3-a]quinoxalin-8-yl)pyrimidin-2-yl)oxy)propan-1-amine (Example 6);

N,N-dimethyl-3-((2-(1-(tetrahydro-2H-pyran-4-yl)-[1,2,4]triazolo[4,3-a]quinoxalin-8-yl)pyrimidin-5-yl)oxy)propan-1-amine (Example 7);

N,N-dimethyl-3-((5-(1-(tetrahydro-2H-pyran-4-yl)-[1,2,4]triazolo[4,3-a]quinoxalin-8-yl)pyrazin-2-yl)oxy)propan-1-amine (Example 8);

N,N-dimethyl-2-(4-(1-(tetrahydro-2H-pyran-4-yl)-[1,2,4]triazolo[4,3-a]quinoxalin-8-yl)phenoxy)ethan-1-amine (Example 9);

N-(3-(dimethylamino)propyl)-4-(1-(tetrahydro-2H-pyran-4-yl)-[1,2,4]triazolo[4,3-a]quinoxalin-8-yl)aniline (Example 10);

N-(3-(dimethylamino)propyl)-N-methyl-4-(1-(tetrahydro-2H-pyran-4-yl)-[1,2,4]triazolo[4,3-a]quinoxalin-8-yl)aniline (Example 11);

N,N-dimethyl-1-(4-(1-(tetrahydro-2H-pyran-4-yl)-[1,2,4]triazolo[4,3-a]quinoxalin-8-yl)phenyl)piperidin-4-amine (Example 12);

8-(4-(4-methylpiperazin-1-yl)phenyl)-1-(tetrahydro-2H-pyran-4-yl)-[1,2,4]triazolo[4,3-a]quinoxaline (Example 13);

1-(tetrahydro-2H-pyran-4-yl)-8-(4-((3S,5R)-3,4,5-trimethylpiperazin-1-yl)phenyl)-[1,2,4]triazolo[4,3-a]quinoxaline (Example 14);

N,N-dimethyl-1-(5-(1-(tetrahydro-2H-pyran-4-yl)-[1,2,4]triazolo[4,3-a]quinoxalin-8-yl)pyridin-2-yl)piperidin-4-amine (Example 15);

8-(6-(4-methylpiperazin-1-yl)pyridin-3-yl)-1-(tetrahydro-2H-pyran-4-yl)-[1,2,4]triazolo[4,3-a]quinoxaline (Example 16);

1-(tetrahydro-2H-pyran-4-yl)-8-(6-((3S,5R)-3,4,5-trimethylpiperazin-1-yl)pyridin-3-yl)-[1,2,4]triazolo[4,3-a]quinoxaline (Example 17);

N,N-dimethyl-4-(4-(1-(tetrahydro-2H-pyran-4-yl)-[1,2,4]triazolo[4,3-a]quinoxalin-8-yl)phenyl)cyclohexan-1-amine (Example 18);

N,N-dimethyl-4-(5-(1-(tetrahydro-2H-pyran-4-yl)-[1,2,4]triazolo[4,3-a]quinoxalin-8-yl)pyridin-2-yl)cyclohexan-1-amine (Example 19);

N,N-dimethyl-3-(4-(1-(piperidin-1-yl)-[1,2,4]triazolo[4,3-a]quinoxalin-8-yl)phenoxy)propan-1-amine (Example 20);

N,N-dimethyl-3-(4-(1-morpholino-[1,2,4]triazolo[4,3-a]quinoxalin-8-yl)phenoxy)propan-1-amine (Example 21);

N,N-dimethyl-3-(4-(1-(4-methylpiperazin-1-yl)-[1,2,4]triazolo[4,3-a]quinoxalin-8-yl)phenoxy)propan-1-amine (Example 22);

N,N-dimethyl-3-(4-(1-((3S,5R)-3,4,5-trimethylpiperazin-1-yl)-[1,2,4]triazolo[4,3-a]quinoxalin-8-yl)phenoxy)propan-1-amine (Example 23);

N,N-dimethyl-3-((5-(1-morpholino-[1,2,4]triazolo[4,3-a]quinoxalin-8-yl)pyridin-2-yl)oxy)propan-1-amine (Example 24);

N,N-dimethyl-3-((5-(1-(4-methylpiperazin-1-yl)-[1,2,4]triazolo[4,3-a]quinoxalin-8-yl)pyridin-2-yl)oxy)propan-1-amine (Example 25);

N,N-dimethyl-3-((5-(1-((3S,5R)-3,4,5-trimethylpiperazin-1-yl)-[1,2,4]triazolo[4,3-a]quinoxalin-8-yl)pyridin-2-yl)oxy)propan-1-amine (Example 26);

N,N-dimethyl-3-(4-(1-(morpholinomethyl)-[1,2,4]triazolo[4,3-a]quinoxalin-8-yl)phenoxy)propan-1-amine (Example 27);

3-(4-(1-(1H-imidazol-1-yl)-[1,2,4]triazolo[4,3-a]quinoxalin-8-yl)phenoxy)-N,N-dimethylpropan-1-amine (Example 28);

3-(4-(1-(1H-imidazol-4-yl)-[1,2,4]triazolo[4,3-a]quinoxalin-8-yl)phenoxy)-N,N-dimethylpropan-1-amine (Example 29);

N,N-dimethyl-3-(4-(1-(tetrahydro-2H-pyran-4-yl)pyrido[3,4-e][1,2,4]triazolo[4,3-a]pyrazin-8-yl)phenoxy)propan-1-amine (Example 30);

N,N-dimethyl-3-(4-(9-(tetrahydro-2H-pyran-4-yl)pyrido[3,2-e][1,2,4]triazolo[4,3-a]pyrazin-2-yl)phenoxy)propan-1-amine (Example 31);

N,N-dimethyl-3-(4-(1-(tetrahydro-2H-pyran-4-yl)imidazo[1,2-a]quinoxalin-8-yl)phenoxy)propan-1-amine (Example 32);

N,N-dimethyl-3-((5-(1-(tetrahydro-2H-pyran-4-yl)imidazo[1,5-c]quinazolin-9-yl)pyridin-2-yl)oxy)propan-1-amine (Example 33);

N,N-dimethyl-3-(4-(1-(tetrahydro-2H-pyran-4-yl)imidazo[1,5-c]quinazolin-9-yl)phenoxy)propan-1-amine (Example 34);

N,N-dimethyl-3-((5-(1-morpholinoimidazo[1,5-c]quinazolin-9-yl)pyridin-2-yl)oxy)propan-1-amine (Example 35);

N,N-dimethyl-3-(4-(1-morpholinoimidazo[1,5-c]quinazolin-9-yl)phenoxy)propan-1-amine (Example 36);

N,N-dimethyl-3-(4-(1-(tetrahydro-2H-pyran-4-yl)imidazo[1,5-a]quinoxalin-8-yl)phenoxy)propan-1-amine (Example 37);

N,N-dimethyl-3-(4-(1-(tetrahydro-2H-pyran-4-yl)-pyrrolo[1,2-a]quinoxalin-8-yl)phenoxy)propan-1-amine (Example 38);

8-phenyl-1-(tetrahydro-2H-pyran-4-yl)-[1,2,4]triazolo[4,3-a]quinoxaline (Example 39);

N,N,N-trimethyl-3-((4-(1-(tetrahydro-2H-pyran-4-yl)-[1,2,4]triazolo[4,3-a]quinoxalin-8-yl)phenyl)amino)propan-1-aminium (Example 40);

1-(4-(1-(tetrahydro-2H-pyran-4-yl)-[1,2,4]triazolo[4,3-a]quinoxalin-8-yl)phenyl)piperidin-4-amine (Example 41);

N-methyl-1-(4-(1-(tetrahydro-2H-pyran-4-yl)-[1,2,4]triazolo[4,3-a]quinoxalin-8-yl)phenyl)piperidin-4-amine (Example 42);

N-ethyl-1-(4-(1-(tetrahydro-2H-pyran-4-yl)-[1,2,4]triazolo[4,3-a]quinoxalin-8-yl)phenyl)piperidin-4-amine (Example 43);

1-(2-fluoro-4-(1-(tetrahydro-2H-pyran-4-yl)-[1,2,4]triazolo[4,3-a]quinoxalin-8-yl)phenyl)-N,N-dimethylpiperidin-4-amine (Example 44);

1-(2-chloro-4-(1-(tetrahydro-2H-pyran-4-yl)-[1,2,4]triazolo[4,3-a]quinoxalin-8-yl)phenyl)-N,N-dimethylpiperidin-4-amine (Example 45);

N,N-dimethyl-1-(2-methyl-4-(1-(tetrahydro-2H-pyran-4-yl)-[1,2,4]triazolo[4,3-a]quinoxalin-8-yl)phenyl)piperidin-4-amine (Example 46);

N,N-dimethyl-1-(4-(1-(tetrahydro-2H-pyran-4-yl)-[1,2,4]triazolo[4,3-a]quinoxalin-8-yl)-2-(trifluoromethyl)phenyl)piperidin-4-amine (Example 47);

1-(3-fluoro-4-(1-(tetrahydro-2H-pyran-4-yl)-[1,2,4]triazolo[4,3-a]quinoxalin-8-yl)phenyl)-N,N-dimethylpiperidin-4-amine (Example 48);

1-(3-chloro-4-(1-(tetrahydro-2H-pyran-4-yl)-[1,2,4]triazolo[4,3-a]quinoxalin-8-yl)phenyl)-N,N-dimethylpiperidin-4-amine (Example 49);

N,N-dimethyl-1-(3-methyl-4-(1-(tetrahydro-2H-pyran-4-yl)-[1,2,4]triazolo[4,3-a]quinoxalin-8-yl)phenyl)piperidin-4-amine (Example 50);

N,N-dimethyl-1-(4-(1-(tetrahydro-2H-pyran-4-yl)-[1,2,4]triazolo[4,3-a]quinoxalin-8-yl)-3-(trifluoromethyl)phenyl)piperidin-4-amine (Example 51);

N,N-dimethyl-1-(6-(1-(tetrahydro-2H-pyran-4-yl)-[1,2,4]triazolo[4,3-a]quinoxalin-8-yl)pyridin-3-yl)piperidin-4-amine (Example 52);

N,N-dimethyl-1-(1-(4-(1-(tetrahydro-2H-pyran-4-yl)-[1,2,4]triazolo[4,3-a]quinoxalin-8-yl)phenyl)piperidin-4-yl)methanamine (Example 53);

N,N-dimethyl-2-(1-(4-(1-(tetrahydro-2H-pyran-4-yl)-[1,2,4]triazolo[4,3-a]quinoxalin-8-yl)phenyl)piperidin-4-yl)ethan-1-amine (Example 54);

3-(2-fluoro-4-(1-((3S,5R)-3,4,5-trimethylpiperazin-1-yl)-[1,2,4]triazolo[4,3-a]quinoxalin-8-yl)phenoxy)-N,N-dimethylpropan-1-amine (Example 55);

3-(2-chloro-4-(1-((3S,5R)-3,4,5-trimethylpiperazin-1-yl)-[1,2,4]triazolo[4,3-a]quinoxalin-8-yl)phenoxy)-N,N-dimethylpropan-1-amine (Example 56);

N,N-dimethyl-3-(2-(trifluoromethyl)-4-(1-((3S,5R)-3,4,5-trimethylpiperazin-1-yl)-[1,2,4]triazolo[4,3-a]quinoxalin-8-yl)phenoxy)propan-1-amine (Example 57);

N,N-dimethyl-1-(4-(1-((3S,5R)-3,4,5-trimethylpiperazin-1-yl)-[1,2,4]triazolo[4,3-a]quinoxalin-8-yl)phenyl)piperidin-4-amine (Example 58);

1-(2-fluoro-4-(1-((3S,5R)-3,4,5-trimethylpiperazin-1-yl)-[1,2,4]triazolo[4,3-a]quinoxalin-8-yl)phenyl)-N,N-dimethylpiperidin-4-amine (Example 59);

1-(2-chloro-4-(1-((3S,5R)-3,4,5-trimethylpiperazin-1-yl)-[1,2,4]triazolo[4,3-a]quinoxalin-8-yl)phenyl)-N,N-dimethylpiperidin-4-amine (Example 60);

N,N-dimethyl-1-(2-(trifluoromethyl)-4-(1-((3S,5R)-3,4,5-trimethylpiperazin-1-yl)-[1,2,4]triazolo[4,3-a]quinoxalin-8-yl)phenyl)piperidin-4-amine (Example 61);

1-(2-fluoro-6-(trifluoromethyl)-4-(1-((3S,5R)-3,4,5-trimethylpiperazin-1-yl)-[1,2,4]triazolo[4,3-a]quinoxalin-8-yl)phenyl)-N,N-dimethylpiperidin-4-amine (Example 62);

1-(2-chloro-6-(trifluoromethyl)-4-(1-((3S,5R)-3,4,5-trimethylpiperazin-1-yl)-[1,2,4]triazolo[4,3-a]quinoxalin-8-yl)phenyl)-N,N-dimethylpiperidin-4-amine (Example 63);

1-(4-(1-(4-(dimethylamino)piperidin-1-yl)-[1,2,4]triazolo[4,3-a]quinoxalin-8-yl)phenyl)-N,N-dimethylpiperidin-4-amine (Example 64);

N,N-dimethyl-1-(4-(1-(morpholinomethyl)-[1,2,4]triazolo[4,3-a]quinoxalin-8-yl)phenyl)piperidin-4-amine (Example 65);

N-methyl-1-(4-(1-(morpholinomethyl)-[1,2,4]triazolo[4,3-a]quinoxalin-8-yl)phenyl)piperidin-4-amine (Example 66);

8-phenyl-1-(tetrahydro-2H-pyran-4-yl)pyrido[3,4-e][1,2,4]triazolo[4,3-a]pyrazine (Example 67);

N,N-dimethyl-1-(4-(1-(tetrahydro-2H-pyran-4-yl)pyrido[3,4-e][1,2,4]triazolo[4,3-a]pyrazin-8-yl)phenyl)methanamine (Example 68);

N,N-dimethyl-3-(4-(1-(tetrahydro-2H-pyran-4-yl)pyrido[3,4-e][1,2,4]triazolo[4,3-a]pyrazin-8-yl)phenoxy)propan-1-amine (Example 69);

N-methyl-1-(4-(1-(tetrahydro-2H-pyran-4-yl)pyrido[3,4-e][1,2,4]triazolo[4,3-a]pyrazin-8-yl)phenyl)piperidin-4-amine (Example 70);

N,N-dimethyl-1-(4-(1-(tetrahydro-2H-pyran-4-yl)pyrido[3,4-e][1,2,4]triazolo[4,3-a]pyrazin-8-yl)phenyl)piperidin-4-amine (Example 71);

N,N-dimethyl-1-(4-(9-(tetrahydro-2H-pyran-4-yl)pyrido[3,2-e][1,2,4]triazolo[4,3-a]pyrazin-2-yl)phenyl)piperidin-4-amine (Example 72);

1-(4-(9-(tetrahydro-2H-pyran-4-yl)pyrido[3,2-e][1,2,4]triazolo[4,3-a]pyrazin-2-yl)phenyl)piperidin-4-amine (Example 73);

N-methyl-1-(4-(9-(tetrahydro-2H-pyran-4-yl)pyrido[3,2-e][1,2,4]triazolo[4,3-a]pyrazin-2-yl)phenyl)piperidin-4-amine (Example 74);

N-ethyl-1-(4-(9-(tetrahydro-2H-pyran-4-yl)pyrido[3,2-e][1,2,4]triazolo[4,3-a]pyrazin-2-yl)phenyl)piperidin-4-amine (Example 75);

N,N-dimethyl-1-(5-(9-(tetrahydro-2H-pyran-4-yl)pyrido[3,2-e][1,2,4]triazolo[4,3-a]pyrazin-2-yl)pyridin-2-yl)piperidin-4-amine (Example 76);

N-methyl-1-(4-(9-(morpholinomethyl)pyrido[3,2-e][1,2,4]triazolo[4,3-a]pyrazin-2-yl)phenyl)piperidin-4-amine (Example 77);

N,N-dimethyl-1-(4-(9-(morpholinomethyl)pyrido[3,2-e][1,2,4]triazolo[4,3-a]pyrazin-2-yl)phenyl)piperidin-4-amine (Example 78);

N,N-dimethyl-3-(4-(9-(morpholinomethyl)pyrido[3,2-e][1,2,4]triazolo[4,3-a]pyrazin-2-yl)phenoxy)propan-1-amine (Example 79);

N,N-dimethyl-3-(4-(9-((3S,5R)-3,4,5-trimethylpiperazin-1-yl)pyrido[3,2-e][1,2,4]triazolo[4,3-a]pyrazin-2-yl)phenoxy)propan-1-amine (Example 80);

3-(2-fluoro-4-(9-((3S,5R)-3,4,5-trimethylpiperazin-1-yl)pyrido[3,2-e][1,2,4]triazolo[4,3-a]pyrazin-2-yl)phenoxy)-N,N-dimethylpropan-1-amine (Example 81);

3-(2-chloro-4-(9-((3S,5R)-3,4,5-trimethylpiperazin-1-yl)pyrido[3,2-e][1,2,4]triazolo[4,3-a]pyrazin-2-yl)phenoxy)-N,N-dimethylpropan-1-amine (Example 82);

N,N-dimethyl-3-(2-(trifluoromethyl)-4-(9-((3S,5R)-3,4,5-trimethylpiperazin-1-yl)pyrido[3,2-e][1,2,4]triazolo[4,3-a]pyrazin-2-yl)phenoxy)propan-1-amine (Example 83);

N,N-dimethyl-1-(4-(9-((3S,5R)-3,4,5-trimethylpiperazin-1-yl)pyrido[3,2-e][1,2,4]triazolo[4,3-a]pyrazin-2-yl)phenyl)piperidin-4-amine (Example 84);

1-(2-fluoro-4-(9-((3S,5R)-3,4,5-trimethylpiperazin-1-yl) pyrido[3,2-e][1,2,4]triazolo[4,3-a]pyrazin-2-yl)phenyl)-N,N-dimethylpiperidin-4-amine (Example 85);

1-(2-chloro-4-(9-((3S,5R)-3,4,5-trimethylpiperazin-1-yl) pyrido[3,2-e][1,2,4]triazolo[4,3-a]pyrazin-2-yl)phenyl)-N,N-dimethylpiperidin-4-amine (Example 86);

N,N-dimethyl-1-(2-(trifluoromethyl)-4-(9-((3S,5R)-3,4,5-trimethylpiperazin-1-yl)pyrido[3,2-e][1,2,4]triazolo[4,3-a]pyrazin-2-yl)phenyl)piperidin-4-amine (Example 87);

1-(2-fluoro-6-(trifluoromethyl)-4-(9-((3S,5R)-3,4,5-trimethylpiperazin-1-yl)pyrido[3,2-e][1,2,4]triazolo[4,3-a]pyrazin-2-yl)phenyl)-N,N-dimethylpiperidin-4-amine (Example 88);

1-(2-chloro-6-(trifluoromethyl)-4-(9-((3S,5R)-3,4,5-trimethylpiperazin-1-yl)pyrido[3,2-e][1,2,4]triazolo[4,3-a]pyrazin-2-yl)phenyl)-N,N-dimethylpiperidin-4-amine (Example 89);

1-(2-(4-(4-(dimethylamino)piperidin-1-yl)phenyl)pyrido[3,2-e][1,2,4]triazolo[4,3-a]pyrazin-9-yl)-N,N-dimethylpiperidin-4-amine (Example 90);

1-(2-(4-(4-(dimethylamino)piperidin-1-yl)-3-fluorophenyl)pyrido[3,2-e][1,2,4]triazolo[4,3-a]pyrazin-9-yl)-N,N-dimethylpiperidin-4-amine (Example 91);

1-(2-(3-chloro-4-(4-(dimethylamino)piperidin-1-yl)phenyl) pyrido[3,2-e][1,2,4]triazolo[4,3-a]pyrazin-9-yl)-N,N-dimethylpiperidin-4-amine (Example 92);

1-(2-(4-(4-(dimethylamino)piperidin-1-yl)-3-(trifluoromethyl)phenyl)pyrido[3,2-e][1,2,4]triazolo[4,3-a]pyrazin-9-yl)-N,N-dimethylpiperidin-4-amine (Example 93);

N-methyl-1-(2-fluoro-4-(1-((3S,5R)-3,4,5-trimethylpiperazin-1-yl)-[1,2,4]triazolo[4,3-a]quinoxalin-8-yl)phenyl)piperidin-4-amine (Example 94);

N-methyl-1-(2-(trifluoromethyl)-4-(1-((3S,5R)-3,4,5-trimethylpiperazin-1-yl)-[1,2,4]triazolo[4,3-a]quinoxalin-8-yl)phenyl)piperidin-4-amine (Example 95);

N-ethyl-1-(2-fluoro-4-(1-((3S,5R)-3,4,5-trimethylpiperazin-1-yl)-[1,2,4]triazolo[4,3-a]quinoxalin-8-yl)phenyl)piperidin-4-amine (Example 96);

N-ethyl-1-(2-(trifluoromethyl)-4-(1-((3S,5R)-3,4,5-trimethylpiperazin-1-yl)-[1,2,4]triazolo[4,3-a]quinoxalin-8-yl)phenyl)piperidin-4-amine (Example 97);

N,N-dimethyl-1-(2-(trifluoromethyl)-4-(1-((3S,5R)-4-ethyl-3,5-dimethylpiperazin-1-yl)-[1,2,4]triazolo[4,3-a]quinoxalin-8-yl)phenyl)piperidin-4-amine (Example 98);

N,N-dimethyl-1-(2-(trifluoromethyl)-4-(1-((3S,5R)-4-isopropyl-3,5-dimethylpiperazin-1-yl)-[1,2,4]triazolo[4,3-a]quinoxalin-8-yl)phenyl)piperidin-4-amine (Example 99);

N,N-dimethyl-3-(2-fluoro-4-(1-((2S,6R)-2,6-dimethylmorpholino)-[1,2,4]triazolo[4,3-a]quinoxalin-8-yl)phenoxy)propan-1-amine (Example 100);

N,N-dimethyl-3-(2-chloro-4-(1-((2S,6R)-2,6-dimethylmorpholino)-[1,2,4]triazolo[4,3-a]quinoxalin-8-yl)phenoxy)propan-1-amine (Example 101);

N,N-dimethyl-3-(2-(trifluoromethyl)-4-(1-((2S,6R)-2,6-dimethylmorpholino)-[1,2,4]triazolo[4,3-a]quinoxalin-8-yl)phenoxy)propan-1-amine (Example 102);

1-(4-(1-((2S,6R)-2,6-dimethylmorpholino)-[1,2,4]triazolo [4,3-a]quinoxalin-8-yl)phenyl)-N,N-dimethylpiperidin-4-amine (Example 103);

1-(4-(1-((2S,6R)-2,6-dimethylmorpholino)-[1,2,4]triazolo [4,3-a]quinoxalin-8-yl)-2-fluorophenyl)-N,N-dimethylpiperidin-4-amine (Example 104);

1-(2-chloro-4-(1-((2S,6R)-2,6-dimethylmorpholino)-[1,2,4] triazolo[4,3-a]quinoxalin-8-yl)phenyl)-N,N-dimethylpiperidin-4-amine (Example 105);

1-(4-(1-((2S,6R)-2,6-dimethylmorpholino)-[1,2,4]triazolo [4,3-a]quinoxalin-8-yl)-2-(trifluoromethyl)phenyl)-N,N-dimethylpiperidin-4-amine (Example 106);

1-(4-(1-((2S,6R)-2,6-dimethylmorpholino)-[1,2,4]triazolo [4,3-a]quinoxalin-8-yl)-2-(trifluoromethyl)phenyl)-N-methylpiperidin-4-amine (Example 107);

1-(4-(1-((2S,6R)-2,6-dimethylmorpholino)-[1,2,4]triazolo [4,3-a]quinoxalin-8-yl)-2-(trifluoromethyl)phenyl)-N-ethylpiperidin-4-amine (Example 108);

N,N-dimethyl-3-(2-(trifluoromethyl)-4-(1-((2R,6S)-2,6-dimethyltetrahydro-2H-pyran-4-yl)-[1,2,4]triazolo[4,3-a] quinoxalin-8-yl)phenoxy)propan-1-amine (Example 109);

N,N-dimethyl-1-(2-(trifluoromethyl)-4-(1-((2R,6S)-2,6-dimethyltetrahydro-2H-pyran-4-yl)-[1,2,4]triazolo[4,3-a] quinoxalin-8-yl)phenyl)piperidin-4-amine (Example 110);

N,N-dimethyl-3-(4-(1-(piperidin-1-yl)-[1,2,4]triazolo[4,3-a]quinoxalin-8-yl)-2-(trifluoromethyl)phenoxy)propan-1-amine (Example 111);

1-(2-fluoro-4-(1-(piperidin-1-yl)-[1,2,4]triazolo[4,3-a]quinoxalin-8-yl)phenyl)-N,N-dimethylpiperidin-4-amine (Example 112);

1-(2-chloro-4-(1-(piperidin-1-yl)-[1,2,4]triazolo[4,3-a]quinoxalin-8-yl)phenyl)-N,N-dimethylpiperidin-4-amine (Example 113);

N,N-dimethyl-1-(4-(1-(piperidin-1-yl)-[1,2,4]triazolo[4,3-a]quinoxalin-8-yl)-2-(trifluoromethyl)phenyl)piperidin-4-amine (Example 114);

3-(4-(1-((3R,5S)-3,5-dimethylpiperidin-1-yl)-[1,2,4]triazolo[4,3-a]quinoxalin-8-yl)-2-(trifluoromethyl)phenoxy)-N,N-dimethylpropan-1-amine (Example 115);

1-(4-(1-((3R,5S)-3,5-dimethylpiperidin-1-yl)-[1,2,4]triazolo[4,3-a]quinoxalin-8-yl)-2-(trifluoromethyl)phenyl)-N,N-dimethylpiperidin-4-amine (Example 116);

1-(2-fluoro-4-(9-((3S,5R)-3,4,5-trimethylpiperazin-1-yl) pyrido[3,2-e][1,2,4]triazolo[4,3-a]pyrazin-2-yl)phenyl)-N-methylpiperidin-4-amine (Example 117);

N-methyl-1-(2-(trifluoromethyl)-4-(9-((3S,5R)-3,4,5-trimethylpiperazin-1-yl)pyrido[3,2-e][1,2,4]triazolo[4,3-a] pyrazin-2-yl)phenyl)piperidin-4-amine (Example 118);

N-ethyl-1-(2-fluoro-4-(9-((3S,5R)-3,4,5-trimethylpiperazin-1-yl)pyrido[3,2-e][1,2,4]triazolo[4,3-a]pyrazin-2-yl) phenyl)piperidin-4-amine (Example 119);

N-ethyl-1-(2-(trifluoromethyl)-4-(9-((3S,5R)-3,4,5-trimethylpiperazin-1-yl)pyrido[3,2-e][1,2,4]triazolo[4,3-a] pyrazin-2-yl)phenyl)piperidin-4-amine (Example 120);

N,N-dimethyl-1-(2-(trifluoromethyl)-4-(9-((3S,5R)-4-ethyl-3,5-dimethylpiperazin-1-yl)pyrido[3,2-e][1,2,4]triazolo [4,3-a]pyrazin-2-yl)phenyl)piperidin-4-amine (Example 121);

N,N-dimethyl-1-(2-(trifluoromethyl)-4-(9-((3S,5R)-4-isopropyl-3,5-dimethylpiperazin-1-yl)pyrido[3,2-e][1,2,4] triazolo[4,3-a]pyrazin-2-yl)phenyl)piperidin-4-amine (Example 122);

3-(4-(9-((2S,6R)-2,6-dimethylmorpholino)pyrido[3,2-e][1,2,4]triazolo[4,3-a]pyrazin-2-yl)-2-(trifluoromethyl)phenoxy)-N,N-dimethylpropan-1-amine (Example 123);

1-(4-(9-((2S,6R)-2,6-dimethylmorpholino)pyrido[3,2-e][1,2,4]triazolo[4,3-a]pyrazin-2-yl)phenyl)-N,N-dimethylpiperidin-4-amine (Example 124);

1-(4-(9-((2S,6R)-2,6-dimethylmorpholino)pyrido[3,2-e][1,2,4]triazolo[4,3-a]pyrazin-2-yl)-2-fluorophenyl)-N,N-dimethylpiperidin-4-amine (Example 125);

1-(2-chloro-4-(9-((2S,6R)-2,6-dimethylmorpholino)pyrido [3,2-e][1,2,4]triazolo[4,3-a]pyrazin-2-yl)phenyl)-N,N-dimethylpiperidin-4-amine (Example 126);

1-(4-(9-((2S,6R)-2,6-dimethylmorpholino)pyrido[3,2-e][1,2,4]triazolo[4,3-a]pyrazin-2-yl)-2-(trifluoromethyl)phenyl)-N,N-dimethylpiperidin-4-amine (Example 127);

1-(4-(9-((2S,6R)-2,6-dimethylmorpholino)pyrido[3,2-e][1,2,4]triazolo[4,3-a]pyrazin-2-yl)-2-(trifluoromethyl)phenyl)-N-methylpiperidin-4-amine (Example 128);

1-(4-(9-((2S,6R)-2,6-dimethylmorpholino)pyrido[3,2-e][1,2,4]triazolo[4,3-a]pyrazin-2-yl)-2-(trifluoromethyl)phenyl)-N-ethylpiperidin-4-amine (Example 129);

3-(4-(9-((2R,6S)-2,6-dimethyltetrahydro-2H-pyran-4-yl)pyrido[3,2-e][1,2,4]triazolo[4,3-a]pyrazin-2-yl)-2-(trifluoromethyl)phenoxy)-N,N-dimethylpropan-1-amine (Example 130);

1-(4-(9-((2R,6S)-2,6-dimethyltetrahydro-2H-pyran-4-yl)pyrido[3,2-e][1,2,4]triazolo[4,3-a]pyrazin-2-yl)-2-(trifluoromethyl)phenyl)-N,N-dimethylpiperidin-4-amine (Example 131);

N,N-dimethyl-3-(2-(trifluoromethyl)-4-(9-(piperidin-1-yl)pyrido[3,2-e][1,2,4]triazolo[4,3-a]pyrazin-2-yl)phenoxy)propan-1-amine (Example 132);

N,N-dimethyl-1-(4-(9-(piperidin-1-yl)pyrido[3,2-e][1,2,4]triazolo[4,3-a]pyrazin-2-yl)phenyl)piperidin-4-amine (Example 133);

1-(2-fluoro-4-(9-(piperidin-1-yl)pyrido[3,2-e][1,2,4]triazolo[4,3-a]pyrazin-2-yl)phenyl)-N,N-dimethylpiperidin-4-amine (Example 134);

1-(2-chloro-4-(9-(piperidin-1-yl)pyrido[3,2-e][1,2,4]triazolo[4,3-a]pyrazin-2-yl)phenyl)-N,N-dimethylpiperidin-4-amine (Example 135);

N,N-dimethyl-1-(4-(9-(piperidin-1-yl)pyrido[3,2-e][1,2,4]triazolo[4,3-a]pyrazin-2-yl)-2-(trifluoromethyl)phenyl)piperidin-4-amine (Example 136);

3-(4-(9-((3R,5S)-3,5-dimethylpiperidin-1-yl)pyrido[3,2-e][1,2,4]triazolo[4,3-a]pyrazin-2-yl)-2-(trifluoromethyl)phenoxy)-N,N-dimethylpropan-1-amine (Example 137);

1-(4-(9-((3R,5S)-3,5-dimethylpiperidin-1-yl)pyrido[3,2-e][1,2,4]triazolo[4,3-a]pyrazin-2-yl)-2-(trifluoromethyl)phenyl)-N,N-dimethylpiperidin-4-amine (Example 138);

3-(2-fluoro-4-(9-(tetrahydro-2H-pyran-4-yl)pyrido[3,2-e][1,2,4]triazolo[4,3-a]pyrazin-2-yl)phenoxy)-N,N-dimethylpropan-1-amine (Example 139);

3-(2-chloro-4-(9-(tetrahydro-2H-pyran-4-yl)pyrido[3,2-e][1,2,4]triazolo[4,3-a]pyrazin-2-yl)phenoxy)-N,N-dimethylpropan-1-amine (Example 140);

N,N-dimethyl-3-(4-(9-(tetrahydro-2H-pyran-4-yl)pyrido[3,2-e][1,2,4]triazolo[4,3-a]pyrazin-2-yl)-2-(trifluoromethyl)phenoxy)propan-1-amine (Example 141);

1-(2-fluoro-4-(9-(tetrahydro-2H-pyran-4-yl)pyrido[3,2-e][1,2,4]triazolo[4,3-a]pyrazin-2-yl)phenyl)-N,N-dimethylpiperidin-4-amine (Example 142);

1-(2-chloro-4-(9-(tetrahydro-2H-pyran-4-yl)pyrido[3,2-e][1,2,4]triazolo[4,3-a]pyrazin-2-yl)phenyl)-N,N-dimethylpiperidin-4-amine (Example 143);

N,N-dimethyl-1-(4-(9-(tetrahydro-2H-pyran-4-yl)pyrido[3,2-e][1,2,4]triazolo[4,3-a]pyrazin-2-yl)-2-(trifluoromethyl)phenyl)piperidin-4-amine (Example 144);

1-(3-fluoro-4-(9-(tetrahydro-2H-pyran-4-yl)pyrido[3,2-e][1,2,4]triazolo[4,3-a]pyrazin-2-yl)phenyl)-N,N-dimethylpiperidin-4-amine (Example 145);

3-(2-bromo-4-(1-((3S,5R)-3,4,5-trimethylpiperazin-1-yl)-[1,2,4]triazolo[4,3-a]quinoxalin-8-yl)phenoxy)-N,N-dimethylpropan-1-amine (Example 146);

3-(3-fluoro-4-(1S,5R)-3,4,5-trimethylpiperazin-1-yl)-[1,2,4]triazolo[4,3-a]quinoxalin-8-yl)phenoxy)-N,N-dimethylpropan-1-amine (Example 147);

3-(2-fluoro-6-(trifluoromethyl)-4-(1-((3S,5R)-3,4,5-trimethylpiperazin-1-yl)-[1,2,4]triazolo[4,3-a]quinoxalin-8-yl)phenoxy)-N,N-dimethylpropan-1-amine (Example 148);

3-(2-chloro-6-(trifluoromethyl)-4-(1-((3S,5R)-3,4,5-trimethylpiperazin-1-yl)-[1,2,4]triazolo[4,3-a]quinoxalin-8-yl)phenoxy)-N,N-dimethylpropan-1-amine (Example 149);

3-(2-chloro-3-fluoro-4-(1-((3S,5R)-3,4,5-trimethylpiperazin-1-yl)-[1,2,4]triazolo[4,3-a]quinoxalin-8-yl)phenoxy)-N,N-dimethylpropan-1-amine (Example 150);

1-(2-bromo-4-(1-((3S,5R)-3,4,5-trimethylpiperazin-1-yl)-[1,2,4]triazolo[4,3-a]quinoxalin-8-yl)phenyl)-N,N-dimethylpiperidin-4-amine (Example 151);

and pharmaceutically acceptable salts or prodrugs thereof.

The term "hydrogen (H)" as employed herein includes its isotopes D and T.

The term "alkyl" as employed herein refers to alkyl itself or straight or branched chain radicals of up to ten carbons. Useful alkyl groups include straight-chained or branched $C_{1-10}$ alkyl groups, more preferably $C_{1-6}$ alkyl groups, e.g., $C_{1-4}$ alkyl. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "alkenyl" as employed herein means a straight or branched chain radical of 2-10 carbon atoms, unless the chain length is limited thereto, wherein there is at least one double bond between two of the carbon atoms in the chain. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

Useful alkoxy groups include oxygen substituted by $C_{1-10}$ alkyl groups, preferred $C_1$-$C_6$ alkoxy or $C_1$-$C_4$ alkoxy, mentioned above. The alkyl in the alkoxy group may be optionally substituted. Alkoxy substituents include, without limitation, halo, morpholino, amino including alkylamino and dialkylamino, and carboxy including esters thereof.

Useful alkylthio groups include sulfur substituted by $C_{1-10}$ alkyl groups. The alkyl in the alkylthio group may be optionally substituted. Also included are the sulfoxides and sulfones of such alkylthio groups.

Useful amino and optionally substituted amino groups include $NR_9R_{10}$, wherein $R_9$ and $R_{10}$ are hydrogen, optionally substituted $C_{1-10}$ alkyl (e.g. $C_{1-6}$ alkyl or $C_{1-4}$ alkyl), cycloalkyl, aryl, heteroaryl, or amino; or $R_9$ and $R_{10}$ are combined with the N to form a 5-8 membered heterocyclic ring structure, such as a piperidine; or $R_9$ and $R_{10}$ are combined with the N and an additional N or O atom to form a 5-8 membered heterocyclic ring, such as a piperazine. The alkyl and heterocyclic ring are optionally substituted.

Useful halo or halogen groups include fluoro, chloro, bromo and iodo.

The term "aryl" as employed herein by itself or as part of another group refers to monocyclic, bicyclic or tricyclic aromatic groups containing from 6 to 14 carbon atoms in the ring portion.

Useful aryl groups include $C_6$-$C_{14}$ aryl, preferably $C_6$-$C_{10}$ aryl. Typical $C_6$-$C_{14}$ aryl groups include phenyl, naphthyl, phenanthrenyl, anthracenyl, indenyl, azulenyl, biphenyl, biphenylenyl and fluorenyl groups.

The term "heteroaryl" as employed herein refers to groups having 5 to 14 ring atoms; 6, 10 or 14 π electrons shared in a cyclic array; and containing, as ring atom, carbon atoms and 1-3 heteroatoms selected from oxygen, nitrogen and sulfur.

Useful heteroaryl groups include thienyl (thiophenyl), benzo[d]isothiazol-3-yl, benzo[b]thienyl, naphtho[2,3-b]thienyl, thianthrenyl, furyl (furanyl), pyranyl, isobenzofuranyl, chromenyl, xanthenyl, phenoxanthiinyl, pyrrolyl, imidazolyl, pyrazolyl, pyridyl (pyridinyl, including without limitation 2-pyridyl, 3-pyridyl, and 4-pyridyl), pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-amino-isocoumarin, pyrido[1,2-a]pyrimidin-4-one, tetrahydrocyclopenta[c]pyrazol-3-yl, pyrazolo[1,5-a]pyrimidinyl, pyrrolopyridyl such as pyrrolo[2,3-b]pyridyl, benzoisoxazolyl such as 1,2-benzoisoxazol-3-yl, benzimidazolyl, 2-oxindolyl, thiadiazolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "carbocycle (carbocyclic group)" as employed herein include cycloalkyl and partially saturated carbocyclic groups. Useful cycloalkyl groups are $C_3$-$C_8$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

The term "heterocycle (heterocyclic group)" is used herein to mean a saturated or partially saturated 3-7 membered monocyclic, or 7-10 membered bicyclic ring system, which consists of carbon atoms and one to four heteroatoms independently selected from the group consisting of O, N, and S, wherein the nitrogen and sulfur heteroatoms can be optionally oxidized, the nitrogen can be optionally quaternized. The term also includes any bicyclic group in which any of the above-defined heterocyclic rings is fused to a benzene ring. The heterocyclic ring of heterocycle can be substituted on carbon or on a nitrogen atom if the resulting compound is stable.

Useful saturated or partially saturated heterocyclic groups include tetrahydrofuranyl, tetrahydropyranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups, which are optionally substituted.

In this disclosure, when substituted, the aryl, heteroaryl, carbocyclic and heterocyclic groups may be substituted by one or more (such as 1, 2, 3, or 4) substituents selected from the group consisting of halo, hydroxy, carboxyl, amino, nitro, cyano, $C_{1-6}$ acylamino, $C_{1-6}$ acyloxy, $C_{1-6}$ alkoxy, aryloxy, alkylthio, $C_{1-6}$ alkyl, $C_{6-10}$ aryl, $C_{3-8}$ cycloalkyl, $C_{2-6}$ alkenyl, $C_{2-6}$ alkynyl, $C_{6-10}$ aryl($C_{2-6}$)alkenyl, $C_{6-10}$ aryl($C_{2-6}$)alkynyl, saturated and unsaturated heterocyclic and heteroaryl, methylenedioxy, $C_{1-6}$ haloalkyl, $C_{6-10}$ aryl($C_{1-6}$)alkyl, $C_{1-6}$ hydroxyalkyl, ureido, thiol, azido, carbonyl, di($C_{1-10}$ alkyl)amino, alkylsulfonyl, aminosulfonyl, dialkylaminosulfonyl, and alkylsulfiniyl, and the like. The substituent itself may also be optionally substituted.

In this disclosure, when substituted, alkyl, alkoxy, alkylthio, alkenyl, alkynyl, and cycloalkyl may be optionally substituted by one or more (such as 1, 2, 3, or 4) substituents selected from the group consisting of halo, hydroxy, carboxyl, amino, nitro, cyano, $C_{1-6}$ acylamino, $C_{1-6}$ acyloxy, $C_{1-6}$ alkoxy, aryloxy, alkylthio, $C_{1-6}$ alkyl, $C_{6-10}$ aryl, $C_{3-8}$ cycloalkyl, $C_{2-6}$ alkenyl, $C_{2-6}$ alkynyl, $C_{6-10}$ aryl($C_{2-6}$)alkenyl, $C_{6-10}$ aryl($C_{2-6}$)alkynyl, saturated and unsaturated heterocyclic and heteroaryl, methylenedioxy, $C_{1-6}$ haloalkyl, $C_{6-10}$ aryl($C_{1-6}$)alkyl, $C_{1-6}$ hydroxyalkyl, ureido, thiol, azido, carbonyl, di($C_{1-10}$ alkyl)amino, alkylsulfonyl, aminosulfonyl, dialkylaminosulfonyl, and alkylsulfiniyl, and the like. The substituent itself may also be optionally substituted.

In preferred embodiments, when substituted, alkyl, alkoxy, alkylthio, alkenyl, alkynyl, cycloalkyl, carbonyl, carbocyclic and heterocyclic groups, may be optionally substituted by one or more (such as 1, 2, 3, or 4) substituents selected from the group consisting of halo, hydroxy, carboxyl, amino, nitro, cyano, $C_{1-6}$ acylamino, $C_{1-6}$ acyloxy, $C_{1-6}$ alkoxy, aryloxy, alkylthio, $C_{1-6}$ alkyl, $C_{6-10}$ aryl, $C_{3-8}$ cycloalkyl, $C_{2-6}$ alkenyl, $C_{2-6}$ alkynyl, $C_{6-10}$ aryl($C_{2-6}$)alkenyl, $C_{6-10}$ aryl($C_{2-6}$)alkynyl, saturated and unsaturated heterocyclic and heteroaryl.

It should be understood that in each embodiment, when the substituent is an aryl or a substituent with an aryl, a heteraryl or a substituent with a heteraryl, or a heterocyclic group or a substituent with a heterocyclic group, the number thereof is usually 1.

The term "arylalkyl" is used herein to mean any of the above-mentioned $C_{1-10}$ alkyl groups substituted by any of the above-mentioned $C_{6-14}$ aryl groups. Preferably the arylalkyl group is benzyl, phenethyl or naphthylmethyl.

The term "arylalkenyl" is used herein to mean any of the above-mentioned $C_{2-10}$ alkenyl groups substituted by any of the above-mentioned $C_{6-14}$ aryl groups.

The term "arylalkynyl" is used herein to mean any of the above-mentioned $C_{2-10}$ alkynyl groups substituted by any of the above-mentioned $C_{6-14}$ aryl groups.

The term "aryloxy" is used herein to mean oxygen substituted by any of the above-mentioned $C_{6-14}$ aryl groups, which may be optionally substituted. Useful aryloxy groups include phenoxy and 4-methylphenoxy.

The term "arylalkoxy" is used herein to mean any of the above mentioned $C_{1-10}$ alkoxy groups substituted by any of the above-mentioned aryl groups, which may be optionally substituted. Useful arylalkoxy groups include benzyloxy and phenethyloxy.

Useful haloalkyl groups include $C_{1-10}$ alkyl, or preferably $C_{1-6}$ alkyl substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido. Useful acyl includes $C_{1-6}$ acyl, such as acetyl.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

It should be appreciated that in compound of Formula I, when $A_1$-$A_4$ in the ring including $A_1$-$A_4$ are selected from different atoms, this ring, together with the ring including $A_1$-$A_2$ fused thereto, should meet the valence bond theory. Hence, in certain cases, when selected from C or N, $A_1$, $A_2$, $A_3$ and $A_4$ may be —CH—, —N=, —NH— or —CH$_2$—.

In addition, it should be understood that one or more groups may be selected from each of the ranges defined for $A_1$-$A_4$, $B_1$-$B_3$, $D_1$-$D_4$, $R_1$-$R_{10}$, R', R" and R'" in the above Formulae I, II, IIIa and IIIb respectively and combined to form preferred embodiments of the present disclosure; and the various technical features in the various embodiments described in the present disclosure, the definitions of the various groups, and the various technical features described specifically hereafter (e.g., in the Examples) may be combined with each other to form preferred technical solutions. For example, in certain embodiments, $A_1$ is preferably N; in certain embodiments, $A_2$ is preferably C; in certain embodiments, the ring including $A_1$-$A_4$ is preferably a triazolyl ring, an imidazolyl ring or a pyrrolyl ring; in certain embodiments, $B_1$ is CR", more preferably CH; in certain embodiments, $B_3$ is N; in certain embodiments, $R_3$ is hydrogen. In certain embodiments, R' is H; in certain embodiments, $B_1$ is CH, and R' and $R_3$ are H; in certain embodiments, $A_1$ is N, $A_2$ is C, $B_1$ is CH, and R' and $R_3$ are H; in certain embodiments, the ring including $B_1$-$B_3$ is a phenyl or pyridyl ring; preferably, the ring including $B_1$-$B_3$ is a phenyl ring, or a pyridyl ring in which $B_3$ is N; in certain embodiments, the 6-member ring including $A_1$-$A_2$ is a pyrazinyl ring; in certain embodiments, the ring including $A_1$-$A_4$, the 6-member ring including $A_1$-$A_2$ and the ring including $B_1$-$B_3$ are fused to form pyrido[2,3-e][1,2,4]triazolo[4,3-a]pyrazinyl, pyrido[3,4-e][1,2,4]triazolo[4,3-a]pyrazinyl, pyrido[3,2-e][1,2,4]triazolo[4,3-a]pyrazinyl, [1,2,4]triazolo [4,3-a]quinoxalinyl, imidazo[1,5-c]quinazolinyl, imidazo[1,5-a]quinoxalinyl, imidazo[1,2-a]quinoxalinyl or pyrrolo[1,2-a]quinoxalinyl; in certain embodiments, $R_1$ is selected from the group consisting of tetrahydropyranyl that is not substituted or optionally substituted with 1-4 $C_{1-6}$ alkyl, piperidyl that is not substituted or optionally substituted with —$NR_9R_{10}$ or 1-4 $C_{1-6}$ alkyl, morpholinyl that is not substituted or optionally substituted with 1-4 $C_{1-6}$ alkyl, imidazolyl, piperazinyl that is optionally substituted with 1-4 $C_{1-6}$ alkyl, $C_{1-6}$ alkyl that is optionally substituted with a heterocyclic group; in certain embodiments, the ring including $D_1$-$D_4$ is an optionally substituted pyridyl ring, an optionally substituted phenyl ring, an optionally substituted pyrimidinyl ring or an optionally pyrazinyl ring; preferably, the ring including $D_1$-$D_4$ is an optionally substituted phenyl ring; in certain embodiments, $R_2$ is selected from the group consisting of hydrogen, —$NR_9R_{10}$, $C_{1-6}$ alkyl optionally substituted with —$NR_9R_{10}$, $C_{1-6}$ alkoxy optionally substituted with —$NR_9R_{10}$, $C_{1-6}$ alkyl-NH— optionally substituted with —$NR_9R_{10}$, piperazinyl optionally substituted with 1-3 $C_{1-4}$ alkyl, piperidyl optionally substituted with —$NR_9R_{10}$, and $C_{3-8}$ cycloalkyl optionally substituted with —$NR_9R_{10}$, wherein $R_9$ and $R_{10}$ are independently selected from the group consisting of hydrogen and $C_{1-6}$ alkyl; in certain embodiments, R'" is H, $C_{1-4}$ alkyl, halo or halo $C_{1-4}$ alkyl. The various technical features in the above various embodiments may be combined arbitrarily. Therefore, for example, in certain embodiments, the ring including $A_1$-$A_4$, the 6-member ring including $A_1$-$A_2$ and the ring including $B_1$-$B_3$ in the compounds of the present disclosure are fused to form pyrido[2,3-e][1,2,4]triazolo[4,3-a]pyrazinyl, pyrido [3,4-e][1,2,4]triazolo[4,3-a]pyrazinyl, pyrido[3,2-e][1,2,4]triazolo[4,3-a]pyrazinyl, [1,2,4]triazolo[4,3-a]quinoxalinyl, imidazo[1,5-c]quinazolinyl, imidazo[1,5-a]quinoxalinyl, imidazo[1,2-a]quinoxalinyl or pyrrolo[1,2-a]quinoxalinyl; the ring including $D_1$-$D_4$ is an optionally substituted pyridinyl ring, an optionally substituted phenyl ring, an optionally substituted pyrimidinyl ring, or an optionally substituted pyrazinyl ring; R', R" and $R_3$ are H; R'" is H, $C_{1-4}$ alkyl, halo or halo $C_{1-4}$ alkyl; $R_1$ is selected from the group consisting of tetrahydropyranyl that is not substituted or optionally substituted with 1-4 $C_{1-6}$ alkyl, piperidyl that is not substituted or optionally substituted with —$NR_9R_{10}$ or 1-4 $C_{1-6}$ alkyl, morpholinyl that is not substituted or optionally substituted with 1-4 $C_{1-6}$ alkyl, imidazolyl, piperazinyl that is optionally substituted with 1-4 $C_{1-6}$ alkyl, $C_{1-6}$ alkyl that is optionally substituted with a heterocyclic group; $R_2$ is selected from the group consisting of hydrogen, —$NR_9R_{10}$, $C_{1-6}$ alkyl optionally substituted with —$NR_9R_{10}$, $C_{1-6}$ alkoxy optionally substituted with —$NR_9R_{10}$, $C_{1-6}$ alkyl-NH— optionally substituted with —$NR_9R_{10}$, $C_{1-6}$ alkyl-$NHR_9$— optionally substituted with —$NR_9R_{10}$, piperazinyl optionally substituted with 1-3 $C_{1-4}$ alkyl groups, piperidyl optionally substituted with —$NR_9R_{10}$, and $C_{3-8}$ cycloalkyl optionally substituted with —$NR_9R_{10}$, wherein $R_9$ and $R_{10}$ are independently selected from the group consisting of hydrogen and $C_{1-6}$ alkyl.

In certain embodiments, the ring including $A_1$-$A_4$, the 6-member ring including $A_1$-$A_2$ and the ring including $B_1$-$B_3$ in the compounds of the present disclosure are fused to form [1,2,4]triazolo[4,3-a]quinoxalinyl; the ring including $D_1$-$D_4$ is an optionally substituted pyridinyl, phenyl, pyrimidinyl or pyrazinyl ring, including one substituted with $R_2$; R', R" and $R_3$ are H; R'" is H, $C_{1-4}$ alkyl, halo or halo $C_{1-4}$ alkyl; preferably, R'" is located at the positions of $D_1$ and/or $D_2$, or at the positions of $D_2$ and/or $D_3$; $R_1$ is selected from the group consisting of tetrahydropyranyl that is not substituted or optionally substituted with 1-4 $C_{1-6}$ alkyl groups, piperidyl that is not substituted or optionally substituted with —$NR_9R_{10}$ or 1-4 $C_{1-6}$ alkyl groups, morpholinyl that is not substituted or optionally substituted with 1-4 $C_{1-6}$ alkyl groups, imidazolyl, piperazinyl that is optionally substituted with 1-4 $C_{1-6}$ alkyl, $C_{1-6}$ alkyl that is optionally substituted with one heterocyclic group (preferably one morpholinyl); $R_2$ is selected from the group consisting of —$NR_9R_{10}$, $C_{1-6}$ alkoxy optionally substituted with —$NR_9R_{10}$, $C_{1-6}$ alkyl-NH— optionally substituted with —$NR_9R_{10}$, $C_{1-6}$ alkyl-$NHR_9$— optionally substituted with —$NR_9R_{10}$, piperazinyl optionally substituted with 1-3 $C_{1-4}$ alkyl groups, piperidyl optionally substituted with —$NR_9R_{10}$, and $C_{3-8}$ cycloalkyl optionally substituted with —$NR_9R_{10}$, wherein $R_9$ and $R_{10}$ are independently selected from the group consisting of hydrogen and $C_{1-6}$ alkyl. In these embodiments, preferred $R_1$ is selected from the group consisting of:

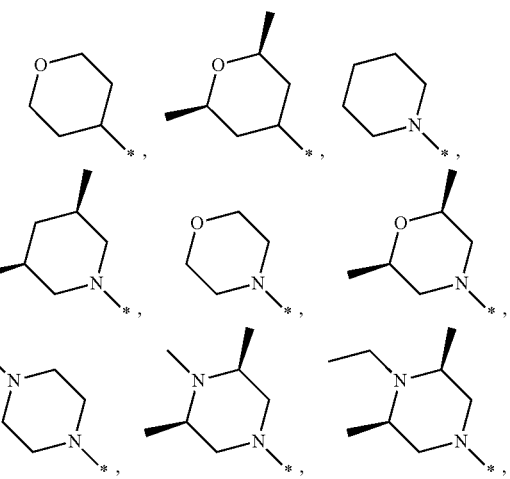

-continued

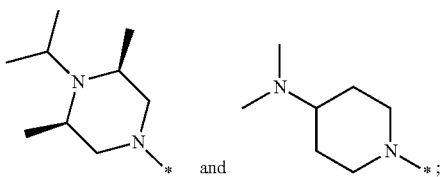

preferred R₂ is selected from the group consisting of:

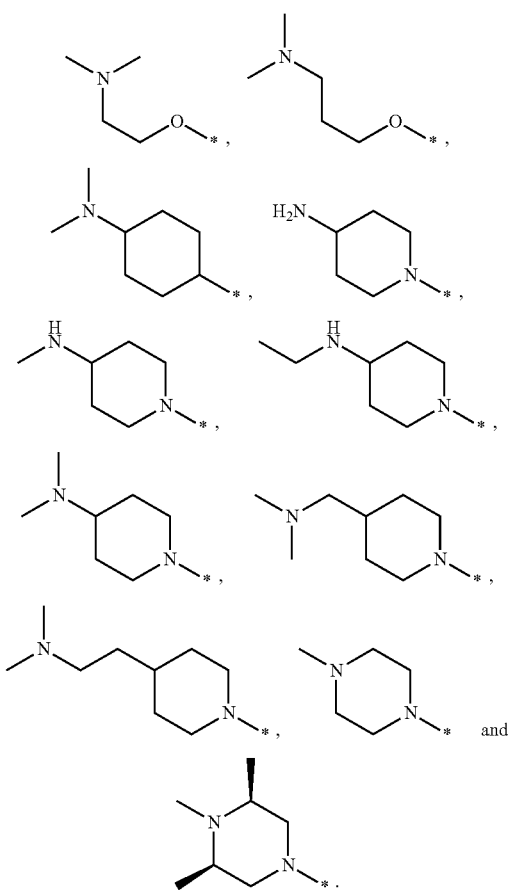

In these embodiments, more preferred R₁ is selected from the group consisting of:

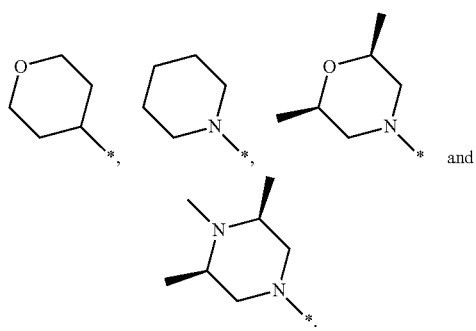

more preferred R₂ is selected from the group consisting of:

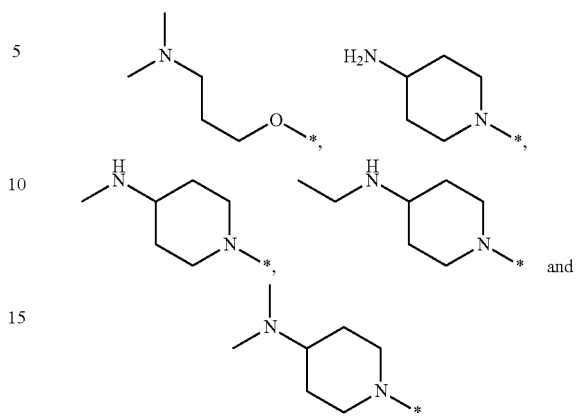

In certain embodiments, the ring including $A_1$-$A_4$, the 6-member ring including $A_1$-$A_2$ and the ring including $B_1$-$B_3$ in the compounds of the present disclosure are fused to form pyridino[2,3-e][1,2,4]triazolo pyrazinyl and pyridino[3,4-e][1,2,4]triazolo[4,3-a]pyrazinyl; the ring including $D_1$-$D_4$ is a pyridyl or phenyl ring; R', R", R''' and $R_3$ are H; $R_1$ is selected from tetrahydropyranyl; and $R_2$ is selected from the group consisting of $C_{1-6}$ alkoxy optionally substituted with —$NR_9R_{10}$, $C_{1-6}$ alkyl optionally substituted with —$NR_9R_{10}$, and piperidyl optionally substituted with —$NR_9R_{10}$, wherein $R_9$ and $R_{10}$ are independently selected from the group consisting of hydrogen and $C_{1-6}$ alkyl. In certain embodiments, the ring including $A_1$-$A_4$, the 6-member ring including $A_1$-$A_2$ and the ring including $B_1$-$B_3$ in the compounds of the present disclosure are fused to form imidazo[1,5-c]quinazolinyl, imidazo[1,5-a]quinoxalinyl, imidazo[1,2-a]quinoxalinyl or pyrrolo[1,2-a]quinoxalinyl; the ring including $D_1$-$D_4$ is a pyridyl or phenyl ring; R', R", R''' and $R_3$ are H; $R_1$ is selected from tetrahydropyranyl and morpholinyl; and $R_2$ is selected from the group consisting of $C_{1-6}$ alkoxy optionally substituted with —$NR_9R_{10}$, wherein $R_9$ and $R_{10}$ are independently selected from $C_{1-6}$ alkyl. In these embodiments, preferred $R_1$ and $R_2$ are those described in any of the preceding embodiments.

In embodiments, the ring including $A_1$-$A_4$, the 6-member ring including $A_1$-$A_2$ and the ring including $B_1$-$B_3$ in the compounds of the present disclosure are fused to form pyrido[3,2-e][1,2,4]triazolo[4,3-a]pyrazinyl; the ring including $D_1$-$D_4$ is a pyridyl or phenyl ring, preferably a phenyl ring; R', R" and $R_3$ are H; R''' is H, $C_{1-4}$ alkyl, halo or halo $C_{1-4}$ alkyl, preferably H, halo or halo $C_{1-4}$ alkyl; preferably, R''' is located at the positions of $D_1$ and/or $D_2$, or at the positions of $D_2$ and/or $D_3$; $R_1$ is selected from tetrahydropyranyl that is not substituted or optionally substituted with 1-4 $C_{1-6}$ alkyl, piperidyl that is not substituted or optionally substituted with —$NR_9R_{10}$ or 1-4 $C_{1-6}$ alkyl, morpholinyl that is not substituted or optionally substituted with 1-4 $C_{1-6}$ alkyl, piperazinyl that is optionally substituted with 1-4 $C_{1-6}$ alkyl, $C_{1-6}$ alkyl that is optionally substituted with a heterocyclic group; and $R_2$ is selected from the group consisting of alkoxy optionally substituted with —$NR_9R_{10}$ and piperidyl optionally substituted with —$NR_9R_{10}$, wherein $R_9$ and $R_{10}$ are independently selected from hydrogen and $C_{1-6}$ alkyl.

In these embodiments, preferred $R_1$ is selected from the group consisting of:

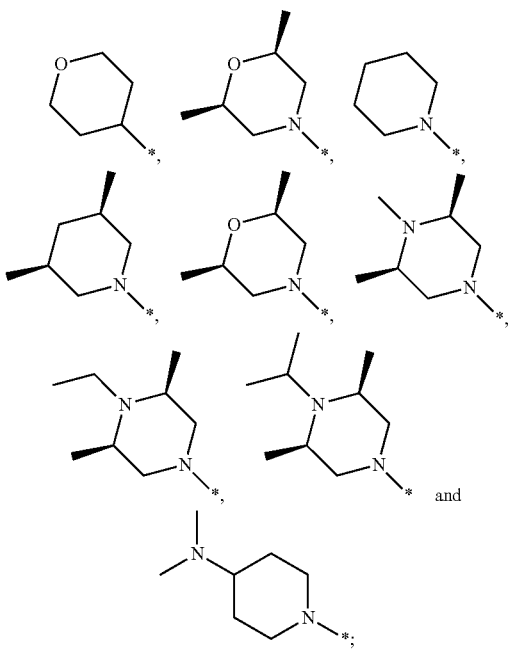

preferred R₂ is selected from the group consisting of:

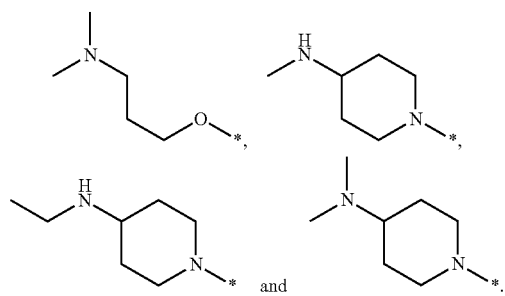

In addition, it should be understood that $A_1$-$A_4$, $B_1$-$B_3$ and $D_1$-$D_4$ in Formulae I, II, IIIa and IIIb in the present disclosure should be selected to meet the valence bond theory. Therefore, for example, in certain cases, in order to meet the valence bond theory, C in a ring may be CH or $CH_2$, or N may be NH when they are not substituted.

Some of the compounds of the present disclosure may exist as stereoisomers including optical isomers. The disclosure includes all stereoisomers and both the racemic mixtures of such stereoisomers as well as the individual enantiomers that may be separated according to methods that are well known to those of ordinary skill in the art.

Examples of pharmaceutically acceptable salts include inorganic and organic acid salts, such as hydrochloride, hydrobromide, phosphate, sulphate, citrate, lactate, tartrate, maleate, fumarate, mandelate and oxalate; and inorganic and organic base salts with bases, such as sodium hydroxy, tris(hydroxymethyl)aminomethane (TRIS, tromethamine) and N-methyl-glucamine.

Examples of prodrugs of the compounds of the disclosure include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (J. Med. Chem. 42:3623-3628 (1999)) and Greenwald, et al., (J. Med. Chem. 42:3657-3667 (1999)); and acetals and ketals of alcohol containing compounds (e.g., those obtained by condensation with chloromethyl methyl ether or chloromethyl ethyl ether according to methods known in the art).

The compounds of this disclosure may be prepared using methods known to those skilled in the art, or the novel methods of this disclosure. Specifically, the compounds of this disclosure with Formulae I, or II or III can be prepared as illustrated by the exemplary reaction in Scheme 1. A 50% toluene solution of 2,3-diamino-5-bromopyridine and ethyl glyoxylate was mixed with dioxane, and the mixture was heated to react to produce 2-hydroxy-7-bromopyrido[2,3-b]pyrazine. 2-Hydroxy-7-bromopyrido[2,3-b]pyrazine was dissolved in $POCl_3$ and heated to react to produce 2-chloro-7-bromopyrido[2,3-b]pyrazine. 2-Chloro-7-bromopyrido[2,3-b]pyrazine was reacted with hydrazine hydrate in ethanol under heating to react to produce 2-hydrazino-7-bromopyrido[2,3-b]pyrazine. 2-Hydrazino-7-bromopyrido[2,3-b]pyrazine and tetrahydropyran-4-carbaldehyde were reacted in MeOH at room temperature to obtain an intermediate, and then the intermediate was reacted with (diacetoxyiodo)benzene (PIDA) in DCM at room temperature, produced 8-bromo-1-(tetrahydro-2H-pyran-4-yl)pyrido[2,3-e][1,2,4]triazolo[4,3-a]pyrazine. 8-Bromo-1-(tetrahydro-2H-pyran-4-yl)pyrido[2,3-e][1,2,4]triazolo[4,3-a]pyrazine, (6-(3-(dimethylamino)propyl)pyridin-3-yl)boronic acid, cesium carbonate and [1,1'-bis(diphenylphosphino)ferrocene]-palladium(II) dichloride dichloromethane complex were reacted in dioxane and water under heating to produce the targeted compound N,N-dimethyl-3-((5-(1-(tetrahydro-2H-pyran-4-yl)pyrido[2,3-e][1,2,4]triazolo[4,3-a]pyrazin-8-yl)pyrid-2-yl)oxo)propan-1-amine.

Scheme 1

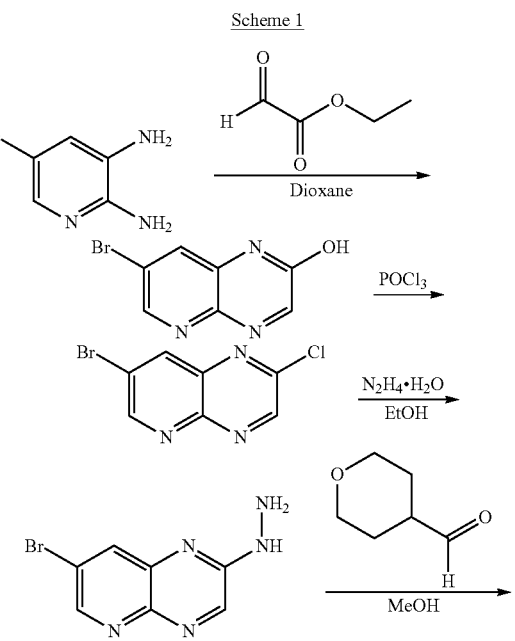

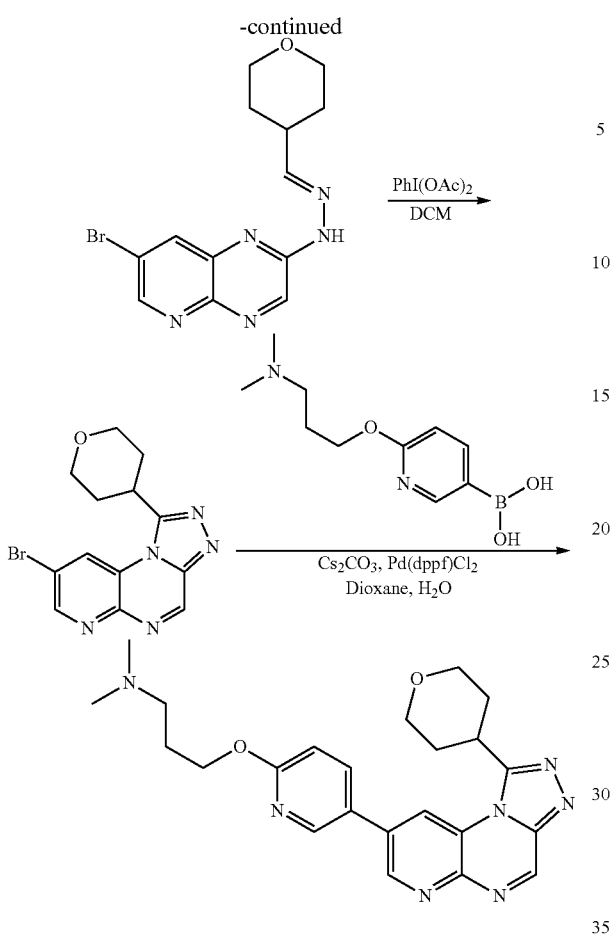

Other related compounds can be prepared similarly. For example, replacement of (6-(3-(dimethylamino)propyl)pyridin-3-yl)boronic acid with N,N-dimethyl-3-(4-(4,4,5,5-tetramethyl-1,3,2-dioxaborolan-2-yl)phenoxy)propan-1-amine produced the targeted compound N,N-dimethyl-3-(4-(1-(tetrahydro-2H-pyran-4-yl)pyrido[2,3-e][1,2,4]triazolo[4,3-a]pyrazin-8-yl)phenoxy)propan-1-amine. Replacement of 2,3-diamino-5-bromopyridine with 3,4-diamino-6-bromopyridine produced the targeted compound N,N-dimethyl-3-(4-(1-(tetrahydro-2H-pyran-4-yl)pyrido[3,4-e][1,2,4]triazolo[4,3-a]pyrazin-8-yl)phenoxy)propan-1-amine.

The compounds of this disclosure can be prepared as illustrated by the exemplary reaction in Scheme 2. Reaction of 2-hydroxyquinoxaline and liquid bromine in acetic acid at room temperature produced 2-hydroxy-7-bromoquinoxaline. 2-Hydroxy-7-bromoquinoxaline was dissolved in POCl₃, and reacted under heating in the presence of DMF as a catalyst to produce 2-chloro-7-bromoquinoxaline. Reaction of 2-chloro-7-bromoquinoxaline and hydrazine hydrate in ethanol under heating produced the targeted product 2-hydrazino-7-bromoquinoxaline. Reaction of 2-hydrazino-7-bromoquinoxaline and tetrahydropyran-4-carbaldehyde in methanol at room temperature produced an intermediate, and then reaction of the intermediate with (diacetoxyiodo)benzene in DCM at room temperature produced 8-bromo-1-(tetrahydro-2H-pyran-4-yl)-[1,2,4]triazolo[4,3-a]quinoxaline. Reaction of 8-bromo-1-(tetrahydro-2H-pyran-4-yl)-[1,2,4]triazolo[4,3-a]quinoxaline, (6-(3-(dimethylamino)propyl)pyridin-3-yl)boronic acid, cesium carbonate and [1,1'-bis(diphenylphosphino)ferrocene]-palladium(II) dichloride dichloromethane complex in dioxane and water under heating produced the targeted product N,N-dimethyl-3-((5-(1-(tetrahydro-2H-pyran-4-yl)-[1,2,4]triazolo[4,3-a]quinoxalin-8-yl)pyridin-2-yl)oxy)propan-1-amine.

Scheme 2

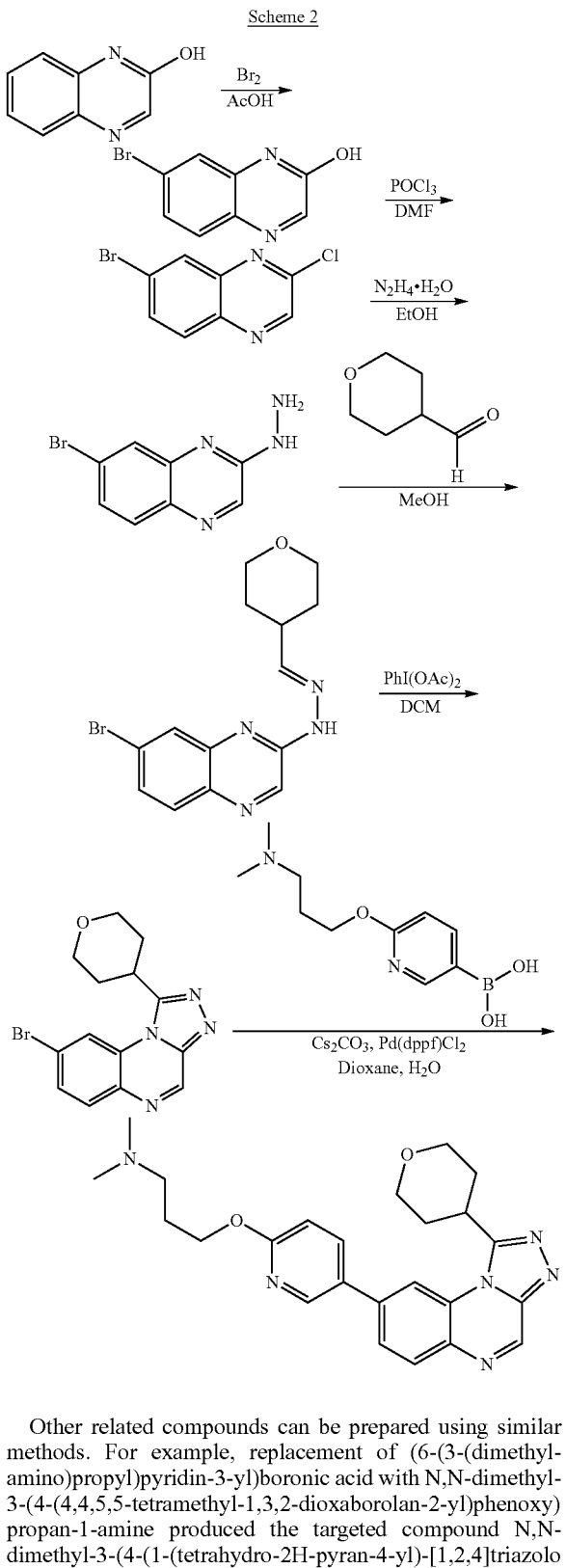

Other related compounds can be prepared using similar methods. For example, replacement of (6-(3-(dimethylamino)propyl)pyridin-3-yl)boronic acid with N,N-dimethyl-3-(4-(4,4,5,5-tetramethyl-1,3,2-dioxaborolan-2-yl)phenoxy)propan-1-amine produced the targeted compound N,N-dimethyl-3-(4-(1-(tetrahydro-2H-pyran-4-yl)-[1,2,4]triazolo

[4,3-a]quinoxalin-8-yl)phenoxy)propan-1-amine.
Replacement of tetrahydropyran-4-carbaldehyde with morpholinyl-4-carbaldehyde produced the targeted compound N,N-dimethyl-3-(4-(1-morpholinyl-[1,2,4]triazolo[4,3-a]quinoxalin-8-yl)phenoxy)propan-1-amine. Replacement of tetrahydropyran-4-carbaldehyde with (2R,6S)-2,6-dimethyl-tetrahydro-2H-pyrane-4-carbonyl chloride produced the targeted compound N,N-dimethyl-3-(2-(trifluoromethyl)-4-(1-((2R,6S)-2,6-dimethyltetrahydro-2H-pyran-4-yl)-[1,2,4]triazolo[4,3-a]quinoxalin-8-yl)phenoxy)propan-1-amine. Replacement of tetrahydropyranyl-4-carbaldehyde with 4-(dimethylamino)piperidine-1-carbonyl chloride produced the targeted compound N,N-dimethyl-1-(4-(1-(4-(dimethylamino)piperidin-1-yl)-[1,2,4]triazolo[4,3-a]quinoxalin-8-yl)phenyl)piperidin-4-amine. Replacement of tetrahydropyran-4-carbaldehyde with (2R,6S)-2,6-dimethylmorpholine-4-carbonyl chloride produced the targeted compound N,N-dimethyl-3-(2-(trifluoromethyl)-4-(1-((2R,6S)-2,6-dimethylmorpholino)-[1,2,4]triazolo[4,3-a]quinoxalin-8-yl)phenoxy)propan-1-amine. Replacement of (6-(3-(dimethylamino)propyl)pyridin-3-yl)boronic acid with N,N-dimethyl-1-(4-(4,4,5,5-tetramethyl-1,3,2-dioxaborolan-2-yl)phenyl)piperidin-4-amine produced the targeted compound N,N-dimethyl-1-(4-(1-((2R,6S)-2,6-dimethyl-morpholino)-[1,2,4]triazolo[4,3-a]quinoxalin-8-yl)phenyl)piperidin-4-amine. Replacement of tetrahydropyran-4-carbaldehyde with piperidine-1-carbonyl chloride produced the targeted compound N,N-dimethyl-1-(2-(trifluoromethyl)-4-(1-(piperidin-1-yl)-[1,2,4]triazolo[4,3-a]quinoxalin-8-yl)phenyl)piperidin-4-amine. Replacement of tetrahydropyran-4-carbaldehyde with (3S,5R)-3,5-dimethylpiperidine-1-carbonyl chloride produced the targeted compound N,N-dimethyl-1-(2-(trifluoromethyl)-4-(1-((3R,5S)-3,5-dimethylpiperidin-1-yl)-[1,2,4]triazolo[4,3-a]quinoxalin-8-yl)phenyl)piperidin-4-amine.

The compounds of this disclosure can be prepared as illustrated by the exemplary reaction in Scheme 3. Reaction of 8-bromo-1-(tetrahydro-2H-pyran-4-yl)-[1,2,4]triazolo[4,3-a]quinoxaline and bis(pinacolato)diboron in dioxane under heating in the presence of potassium acetate and [1,1'-bis(diphenylphosphino)ferrocene]-palladium(II) dichloride as a catalyst produced 1-(tetrahydro-2H-pyran-4-yl)-8-(4,4,5,5-tetramethyl-1,3,2-dioxaborolan-2-yl)-[1,2,4]triazolo[4,3-a]quinoxaline. Reaction of 1-(tetrahydro-2H-pyran-4-yl)-8-(4,4,5,5-tetramethyl-1,3,2-dioxaborolan-2-yl)-[1,2,4]triazolo[4,3-a]quinoxaline and N,N-dimethyl-3-((6-bromopyridin-3-yl)oxy)propan-1-amine in a mixed solvent of dioxane and water under heating in the presence of cesium carbonate and [1,1'-bis(diphenylphosphino)ferrocene]-palladium(II) dichloride as a catalyst produced the targeted compound N,N-dimethyl-3-((6-(1-(tetrahydro-2H-pyran-4-yl)-[1,2,4]triazolo[4,3-a]quinoxalin-8-yl)pyridin-3-yl)oxy)propan-1-amine.

Scheme 3

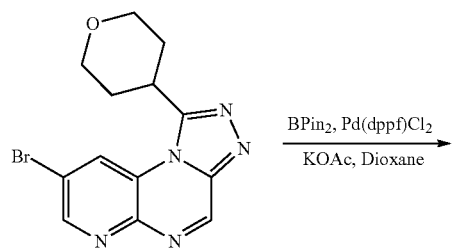

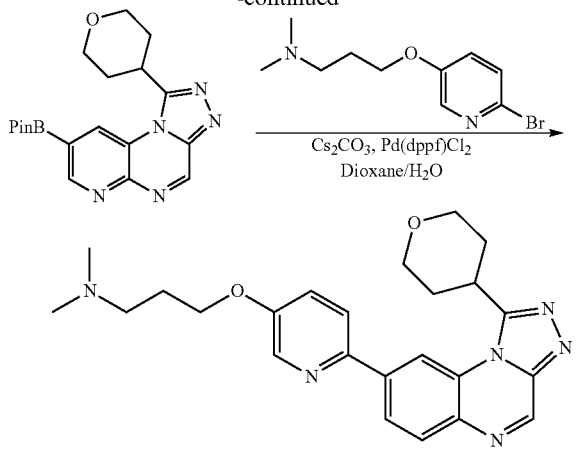

Other related compounds can be prepared using similar methods. For example, replacement of N,N-dimethyl-3-((6-bromopyridin-3-yl)oxy)propan-1-amine with 1-(4-bromophenyl)-N,N-dimethylpiperidin-4-amine produced the targeted compound N,N-dimethyl-1-(4-(1-(tetrahydro-2H-pyran-4-yl)-[1,2,4]triazolo[4,3-a]quinoxalin-8-yl)phenyl)piperidin-4-amine. Replacement of N,N-dimethyl-3-((6-bromopyrid-3-yl)oxy)propan-1-amine with 1-(4-bromophenyl)-4-methylpiperazine produced the targeted compound 8-(4-(4-methylpiperazin-1-yl)phenyl)-1-(tetrahydro-2H-pyran-4-yl)-[1,2,4]triazolo[4,3-a]quinoxaline. Replacement of N,N-dimethyl-3-((6-bromopyridin-3-yl)oxy)propan-1-amine with $N^1$-(4-bromophenyl)-$N^3$,$N^3$-dimethylpropan-1,3-diamine produced the targeted compound N-(3-(dimethylamino)propyl)-4-(1-(tetrahydro-2H-pyran-4-yl)-[1,2,4]triazolo[4,3-a]quinoxalin-8-yl)phenylamine. Replacement of N,N-dimethyl-3-((6-bromopyridin-3-yl)oxy)propan-1-amine with 4-(4-(dimethylamino)cyclohexyl)phenyl trifluoromethanesulfonate produced the targeted compound N,N-dimethyl-4-(4-(1-(tetrahydro-2H-pyran-4-yl)-[1,2,4]triazolo[4,3-a]quinoxalin-8-yl)phenyl)cyclohexylamine.

The compounds of this disclosure can be prepared as illustrated by the exemplary reaction in Scheme 4. Reaction of tert-butyl (2R,6S)-2,6-dimethylpiperazin-1-carbonate and triphosgene in DCM and pyridine at room temperature produced tert-butyl (2R,6S)-4-(chloroformyl)-2,6-dimethylpiperazin-1-carbonate. Reaction of tert-butyl (2R,6S)-4-(chloroformyl)-2,6-dimethylpiperazin-1-carbonate with DMC solution of 7-bromo-2-hydrazinoquinoxaline in N,N-di-isopropylethylamine at room temperature produced tert-butyl (2R,6S)-4-(2-(7-bromoquinoxalin-2-yl)hydrazino-1-formyl)-2,6-dimethyl piperazin-1-carbonate. Reaction of tert-butyl (2R,6S)-4-(2-(7-bromoquinoxalin-2-yl)hydrazino-1-formyl)-2,6-dimethylpiperazin-1-carbonate in POCl₃ under heating produced 8-bromo-1-((2R,6S)-3,5-dimethylpiperazin-1-yl)-[1,2,4]triazolo[4,3-a]quinoxaline. Reaction of 8-bromo-1-((2R,6S)-3,5-dimethylpiperazin-1-yl)-[1,2,4]triazolo[4,3-a]quinoxaline, formic acid and 40% formalin in methanol under heating produced 8-bromo-1-((2R,6S)-3,4,5-trimethylpiperazin-1-yl)-[1,2,4]triazolo[4,3-a]quinoxaline. Reaction of 8-bromo-1-((2R,6S)-3,4,5-trimethylpiperazin-1-yl)-[1,2,4]triazolo[4,3-a]quinoxaline and 3-(N,N-dimethylamino)propoxyphenylboronic acid pinacol ester in dioxane and water under heating in the presence of [1,1'-bis(diphenylphosphino)ferrocene]-palladium(II) dichloride and cesium carbonate as catalysts produced the compound N,N-dimethyl-3-(4-(1-((2R,6S)-3,4,5-trimethylpiperazin-1-yl)-[1,2,4]triazolo[4,3-a]quinoxalin-8-yl)phenoxy)propan-1-amine.

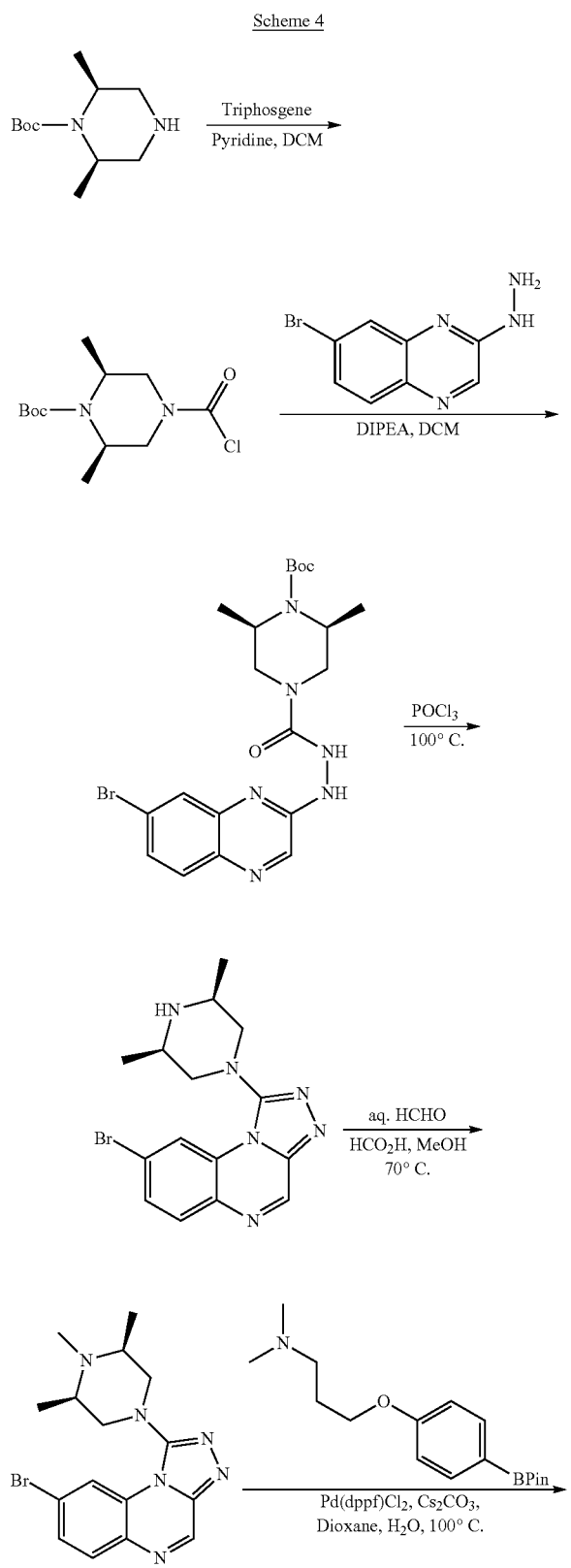

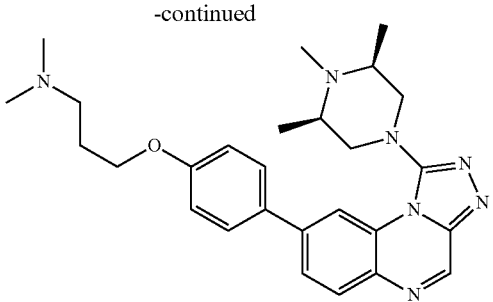

Other related compounds can be prepared using similar methods. For example, replacement of 3-(N,N-dimethylamino)propoxyphenylboronic acid pinacol ester with N,N-dimethyl-1-(4-(4,4,5,5-tetramethyl-1,3,2-dioxaborolan-2-yl)phenyl)piperidin-4-amine produced the targeted compound N,N-dimethyl-1-(4-(1-((3S,5R)-3,4,5-trimethylpiperazin-1-yl)-[1,2,4]triazolo[4,3-a]quinoxalin-8-yl)phenyl)piperidin-4-amine. Replacement of 7-bromo-2-hydrazinoquinoxaline with 3-hydrazino-6-chloropyrido[2,3-b]piperazine produced the targeted compound N,N-dimethyl-3-(4-(9-((3S,5R)-3,4,5-trimethylpiperazin-1-yl)pyrido[3,2-e][1,2,4]triazolo[4,3-a]pyrazin-2-yl)phenoxy)propan-1-amine. Replacement of 3-(N,N-dimethylamino)propoxyphenylboronic acid pinacol ester with N,N-dimethyl-1-(4-(4,4,5,5-tetramethyl-1,3,2-dioxaborolan-2-yl)-2-(trifluoromethyl)phenyl)piperidin-4-amine produced the targeted compound N,N-dimethyl-1-(2-trifluoromethyl-4-(9-((3S,5R)-3,4,5-trimethylpiperazin-1-yl)pyrido[3,2-e][1,2,4]triazolo[4,3-a]pyrazin-2-yl)phenyl)piperidin-4-amine. Replacement of formalin with ethyl iodide produced the targeted compound N,N-dimethyl-1-(2-(trifluoromethyl)-4-(9-((3S,5R)-4-ethyl-3,5-dimethylpiperazin-1-yl)pyrido[3,2-e][1,2,4]triazolo[4,3-a]pyrazin-2-yl)phenyl)piperidin-4-amine.

The compounds of this disclosure can be prepared as illustrated by the exemplary reaction in Scheme 5. 6-Chloropyrido[2,3-b]pyrazin-3(4H)-one was reacted with benzotriazol-1-yl-oxytripyrrolidinophosphonium hexafluorophosphate and N,N-di-isopropyl ethylamine in N,N-dimethyl formamide at room temperature, and then reacted with hydrazine hydrate at 0° C. to produce 3-hydrazino-6-chloropyrido[2,3-b]piperazine. Reaction of 3-hydrazino-6-chloropyrido[2,3-b]pyrazine with tetrahydropyran-4-carbaldehyde in methanol at room temperature produced 6-chloro-3-(2-((tetrahydro-2H-pyran-4-yl)methylene)hydrazino)pyrido[2,3-b]pyrazine. The intermediate was reacted with (diacetoxyiodo)benzene in DCM at room temperature to produce 2-chloro-9-(tetrahydro-2H-pyran-4-yl)pyrido[3,2-e][1,2,4]triazolo[4,3-a]pyrazine. Reaction of 2-chloro-9-(tetrahydro-2H-pyran-4-yl)pyrido[3,2-e][1,2,4]triazolo[4,3-a]pyrazine with 3-(N,N-dimethylamino)propoxyphenylboronic acid pinacol ester in a mixed solvent of dioxane and water under heating in the presence of cesium carbonate and tetra(triphenylphosphine)palladium as catalysts produced the targeted compound N,N-dimethyl-3-(4-(9-(tetrahydro-2H-pyran-4-yl)pyrido[3,2-e][1,2,4]triazolo[4,3-a]pyrazin-2-yl)phenoxy)propan-1-amine.

Scheme 5

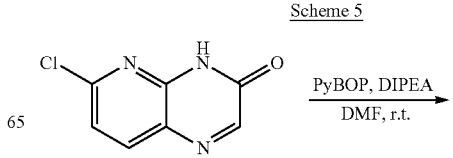

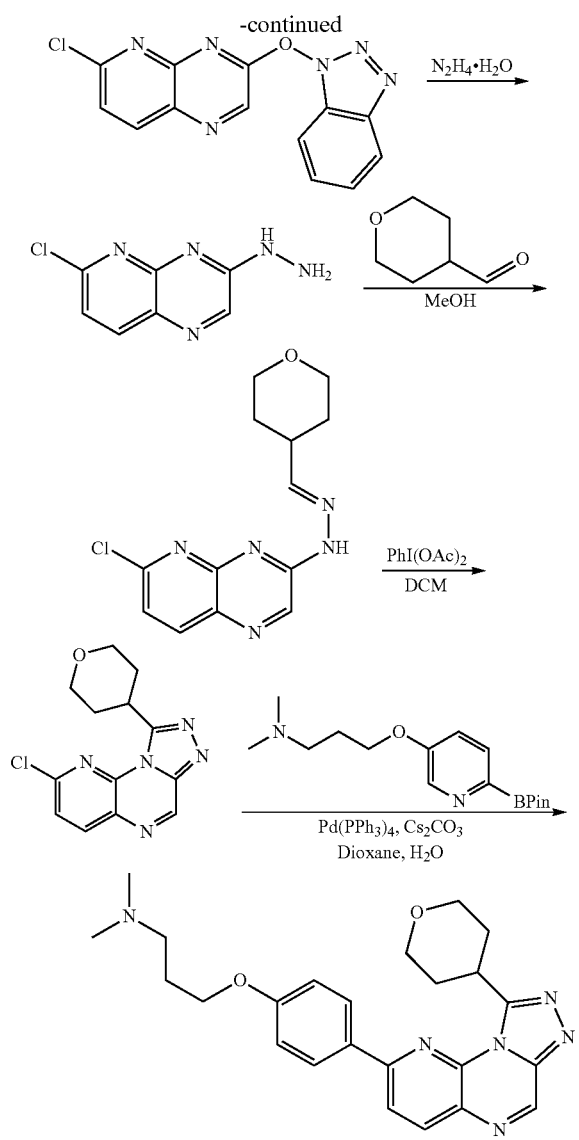

Other related compounds can be prepared using similar methods. For example, replacement of 3-(N,N-dimethylamino)propoxyphenylboronic acid pinacol ester with N,N-dimethyl-1-(4-(4,4,5,5-tetramethyl-1,3,2-dioxaborolan-2-yl)phenyl)piperidin-4-amine produced the targeted compound N,N-dimethyl-1-(4-(9-(tetrahydro-2H-pyran-4-yl)pyrido[3,2-e][1,2,4]triazolo[4,3-a]pyrazin-2-yl)phenyl)piperidin-4-amine. Replacement of tetrahydropyran-4-carbaldehyde with 2-morpholinylacetaldehyde produced the targeted product N,N-dimethyl-3-(4-(9-(morpholinylmethyl)pyrido[3,2-e][1,2,4]triazolo[4,3-a]pyrazin-2-yl)phenoxy)propan-1-amine. Replacement of tetrahydropyran-4-carbaldehyde with 4-(dimethylamino)piperidine-1-carbonyl chloride produced the targeted product N,N-dimethyl-1-(2-(4-(4-(dimethylamino)piperidin-1-yl)-phenyl)pyrido[3,2-e][1,2,4]triazolo[4,3-a]pyrazin-9-yl)piperidin-4-ylamine.
Replacement of tetrahydropyran-4-carbaldehyde with (2R, 6S)-2,6-dimethylmorpholine-4-carbonyl chloride produced the targeted compound N,N-dimethyl-1-(4-(9-((2S,6R)-2,6-dimethyl morpholinyl)pyrido[3,2-e][1,2,4]triazolo[4,3-a]pyrazin-2-yl)phenyl)piperidin-4-amine. Replacement of tetrahydropyran-4-carbaldehyde with (2R,6S)-2,6-dimethyltetrahydro-2H-pyrane-4-carbonyl chloride produced the targeted compound N,N-dimethyl-1-(2-(trifluoromethyl)-4-(9-((2R,6S)-2,6-dimethyltetrahydro-2H-pyran-4-yl)pyrido[3,2-e][1,2,4]triazolo[4,3-a]pyrazin-2-yl)phenyl)piperidin-4-amine. Replacement of tetrahydropyran-4-carbaldehyde with piperidine-1-carbonyl chloride produced the targeted compound N,N-dimethyl-3-(2-(trifluoromethyl)-4-(9-(piperidin-1-yl)pyrido[3,2-e][1,2,4]triazolo[4,3-a]pyrazin-2-yl)phenoxy)propan-1-amine.
Replacement of tetrahydropyran-4-carbaldehyde with (3S, 5R)-3,5-dimethylpiperidine-1-carbonyl chloride produced the targeted compound N,N-dimethyl-3-(2-(trifluoromethyl)-4-(9-((3R,5S)-3,5-dimethylpiperidin-1-yl)pyrido[3,2-e][1,2,4]triazolo[4,3-a]pyrazin-2-yl)phenoxy)propan-1-amine.

One important aspect of the present disclosure is the find that the compounds of Formula I, II and III are kinase inhibitors, especially ATM kinase inhibitors. Therefore, these compounds can be used to treat or prevent a variety of clinical diseases caused by DDR dysfunction or diseases that benefit from the inhibition of kinase activity, such as cancer. In some embodiments, a disease that may be treated or prevented by a compound, medicinal composition, or method of the present disclosure is a DDR-mediated or kinase-mediated disease, as described below.

The present disclosure includes a treatment or prevention method comprising administering to an animal an effective amount of a compound of Formula I, II or III, or a pharmaceutically acceptable salt or prodrug thereof, wherein the treatment or prevention method is used for the treatment or prevention of clinical conditions caused by DDR dysfunction or diseases benefiting from the inhibition of kinase activity, or DDR-mediated or kinase-mediated diseases, such as cancer. Such diseases include, but are not limited to, liver cancer, melanoma, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head and neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In practicing the therapeutic methods, effective amounts of compositions containing therapeutically effective concentrations of the compounds of Formula I, II or III formulated for oral, intravenous, local or topical application, for the treatment of cancer and other diseases, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to an effective regimen. The amount may cure the disease but, typically, is administered in order to ameliorate the symptoms of the disease. Typically, repeated administration is required to achieve the desired amelioration of symptom.

In another embodiment, there is provided a pharmaceutical composition comprising a kinase inhibitor of Formula I or a pharmaceutically acceptable salt thereof and a pharmaceutically acceptable carrier.

Another embodiment of the present disclosure is directed to a pharmaceutical composition effective to treat or prevent cancer comprising a compound of Formula I, II or III, or a pharmaceutically acceptable salt or prodrug thereof, which functions as a kinase inhibitor, in combination with at least one known anticancer agent or a pharmaceutically acceptable salt thereof. In particular, the compound herein can be combined with other anticancer drugs related to the mechanism of DNA damage and repair, including PARP inhibitors Olaparib, Niraprib, Rucaparib and Talazoparib; HDAC inhibitors Volinota, Romididesin, Papiseta and Bailesta; and so on. And the compound herein can be combined with other anticancer drugs related to cell division detection sites, including Chk1/2 inhibitors, CDK4/6 inhibitors such as Paposinib, Wee1/ATR inhibitors, and so on. Known anticancer agents which may be used for combination therapy include, but not are limited to alkylating agents, such as busulfan cis-platin, mitomycin C, and carboplatin; antimitotic agent such as colchicine, vinblastine, paclitaxel, and docetaxel; topoisomerase I inhibitors, such as camptothecin and topotecan; topoisomerase II inhibitors, such as doxorubicin, and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; antibodies such as campath, trastuzumab and rituximab. Other known anticancer agents which may be used for combination therapy include melphalan, chlorambucil, cyclophosphamide, iphosfamide, vincristine, mitoguazone, epirubicin, aclacinomycin, bleomycin, mitoxantrone, methylhydroxy ellipticine, fludarabine, octreotide, retinoic acid, tamoxifen, arsenic trioxide, gemcitabine, letrozole, fulvestrant, bendamustine, pralatrexate, pemetrexed, nelarabine, temozolomide, zoledronic acid, irinotecan, ixabepilone, cabazitazel, vinorebine, panitumumab, Ofatumumab, avastin, imatinib, gefitinib, erlotinib, lapatinib, sorafinib, sunitinib, nilotinib, dasatinib, pazopanib, bortezomib, vorinostat, romidepsin, torisel, everolimus, thalidomide, lenalidomide, and thioguanine.

In practicing the methods of the present disclosure, the compound of the disclosure may be administered together with at least one known anticancer agent as part of a unitary pharmaceutical composition. Alternatively, the compound of the disclosure may be administered apart from at least one known anticancer agent. In one embodiment, the compound of the disclosure and at least one known anticancer agent are administered substantially simultaneously, i.e. the compounds are administered at the same time or one after the other, so long as the compounds reach therapeutic levels in the blood at the same time. In another embodiment, the compound of the disclosure and at least one known anticancer agent are administered according to their individual dose schedule, so long as the compounds reach therapeutic levels in the blood.

Another embodiment of the present disclosure is directed to a bioconjugate, which functions as a kinase inhibitor, that comprises a compound described herein and is effective to inhibit neoplasia. The bioconjugate that inhibits neoplasia is consisted of a compound described herein and at least one known therapeutically useful antibody, such as trastuzumab or rituximab, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of the therapeutically useful antibodies, such as trastuzumab or rituximab.

Similarly, another embodiment of the present disclosure is directed to a composition effective to inhibit neoplasia comprising a compound of Formula I, II or III, or its pharmaceutically acceptable salt or prodrug, which functions as a kinase inhibitor, in combination with radiation therapy. In this embodiment, the compound of the disclosure may be administered at the same time as the radiation therapy is administered or at a different time.

Yet another embodiment of the present disclosure is directed to a composition effective for post-surgical treatment of cancer, comprising a compound of Formula I, II or III, or its pharmaceutically acceptable salt or prodrug, which functions as a kinase inhibitor. The disclosure also relates to a method of treating cancer by surgically removing the tumor and then treating the mammal with one of the pharmaceutical compositions described herein.

Pharmaceutical compositions within the scope of this disclosure include all compositions wherein the compounds of the present disclosure are contained in an amount that is effective to achieve its intended purpose. While individual needs vary, determination of optimal ranges of effective amounts of each component is within the skill of the art. Typically, the compounds or the pharmaceutically acceptable salt thereof may be administered to mammals, orally at a dose of from about 0.0025 to 50 mg/kg of body weight, per day. Preferably, from approximately 0.01 to approximately 10 mg/kg of body weight is orally administered. If a known anticancer agent is also administered, it is administered in an amount that is effective to achieve its intended purpose. The optimal amounts of such known anticancer agents effective for cancer are well known to those skilled in the art.

The unit oral dose may comprise from approximately 0.01 to approximately 50 mg, preferably approximately 0.1 to approximately 10 mg of the compound of the disclosure. The unit dose may be administered one or more times daily, as one or more tablets, each containing from approximately 0.1 to approximately 50 mg, conveniently approximately 0.25 to 10 mg of the compound or its solvates.

In a topical formulation, the compound may be present at a concentration of approximately 0.01 to 100 mg per gram of carrier.

In addition to administering the compound as a raw chemical, the compounds of the disclosure may be administered as part of a suitable pharmaceutical preparation containing pharmaceutically acceptable carriers comprising excipients and auxiliaries, which facilitate processing of the compounds into preparations that may be used pharmaceutically. Preferably, the preparations, particularly those preparations which may be administered orally and that may be used for the preferred type of administration, such as tablets, dragees, and capsules, as well as suitable solutions for administration by injection or orally, contain from approximately 0.01 to 99 percent, preferably from approximately 0.25 to 75 percent of active compound(s), together with the excipient.

Also included within the scope of the present disclosure are the non-toxic pharmaceutically acceptable salts of the compounds of the present disclosure. Acid addition salts are formed by mixing a solution of the compounds of the present disclosure with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Base addition salts are formed by mixing a solution of the compounds of the present disclosure with a solution of a pharmaceutically acceptable non-toxic base, such as sodium hydroxide, potassium hydroxide, choline hydroxide, sodium carbonate, tris(hydroxymethyl)aminomethane (TRIS), N-methyl-glucamine and the like.

The pharmaceutical compositions of the disclosure may be administered to any mammal, so long as they may experience the therapeutic effects of the compounds of the disclosure. Foremost among such mammals are humans and veterinary animals, although the disclosure is not intended to be so limited.

The pharmaceutical compositions of the present disclosure may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present disclosure are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, including, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethyl-cellulose phthalate, are used. Dye stuffs or pigments may be added to the tablets or dragee coatings, e.g., for identification or in order to characterize combinations of active compound doses.

Other pharmaceutical preparations, which may be used orally, include push-fit capsules made of gelatin, as well as soft, sealed capsules made of gelatin and a plasticizer, such as glycerol or sorbitol. The push-fit capsules may contain the active compounds in the form of granules, which may be mixed with fillers, such as lactose; binders, such as starches; and/or lubricants, such as talc or magnesium stearate and stabilizers. In soft capsules, the active compounds are preferably dissolved or suspended in suitable liquids, such as fatty oils, or liquid paraffin. In addition, stabilizers may be added.

Suitable formulations for parenteral administration include aqueous solutions of the active compounds, e.g., aqueous solutions and alkaline solutions of water-soluble salts. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400, or cremophor, or cyclodextrins. Aqueous injection suspensions may contain substances which increase the viscosity of the suspension, e.g., sodium carboxymethyl cellulose, sorbitol, and/or dextran. Optionally, the suspension may also contain stabilizers.

In accordance with one aspect of the present disclosure, compounds of the disclosure are employed in topical and parenteral formulations and are used for the treatment of skin cancer.

The topical compositions of this disclosure are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The following examples are illustrative, but not limiting, of the method and compositions of the present disclosure. Other suitable modifications and adaptations of the variety of conditions and parameters normally encountered in clinical therapy and which are obvious to those skilled in the art are within the spirit and scope of the disclosure.

EXAMPLES

General Remarks

All reagents were of commercial quality. Solvents were dried and purified by standard methods. Mass spectrum analyses were recorded on a Platform II (Agilent 6110) quadrupole mass spectrometer fitted with an electrospray rinterface. $^1$H NMR spectra was recorded at 400 MHz, on a Brucker Ascend 400 apparatus. Chemical shifts were recorded as parts per million (ppm) downfield from TMS (0.00 ppm), and J coupling constants were reported in hertz (Hz). In addition to the intermediate synthesis described in detail in the examples, the synthesis of a portion of the intermediate is also given below, in addition to the methods mentioned below, other intermediate substituted aryl groups may also be synthesized by known methods by those skilled in the art.

Intermediates: Synthesis of Substituted Aryl Groups 1) 4-(4-((dimethylamino)cyclohexyl)phenyl)trifluoromethane sulfonate a) 4-((dimethylamino)cyclohex-1-en-1-yl)trifluoromethane sulphonate: 4-dimethylaminocyclohexanone (500 mg, 3.54 mmol) was dissolved in anhydrous THF (10 mL), and N-phenylbis(trifluoromethanesulfonyl)imine (1.39 g, 3.9 mmol) was added. The atmosphere in the reaction system was replaced with nitrogen three times. After the temperature of the reaction system was lowered to −78° C., lithium dimethylsilylamide (4.3 mL, 4.25 mmol) was added dropwise slowly. After the addition was completed, the temperature was raised to rt and the mixture was stirred overnight. EA (20 mL) and water (5 mL) were added to the reaction solution for extraction and separation. The aqueous phase was extracted with EA (10 mL×2). The organic phases were combined, washed with a saturated saline solution (15 mL), dried with anhydrous sodium sulfate, filtered and concentrated at reduced pressure to obtain a crude product. Isolation and purification by column chromatography (silica gel, DCM:MeOH=10:1 as an eluant) were performed to obtain the targeted compound (630 mg, 65% yield, pale yellow oily substance). LC-MS (ESI): m/z (M+1) 274.07.

b) N,N-dimethyl-4'-methoxy-2,3,4,5-tetrahydro-[1,1'-biphenyl]-4-amine: 4-((dimethylamino)cyclohexyl-1-en-1-yl) trifluoromethane sulfonate (625 mg, 2.3 mmol), 4-methoxyphenylboronic acid (524 mg, 3.45 mmol), potassium acetate (677 mg, 6.9 mmol) and [1,1'-bis(diphenylphosphino)ferrocene]-palladium(II) dichloride dichloromethane complex (188 mg, 0.23 mmol) were dissolved in a mixed solvent of dioxane (4 mL) and water (1 mL) at room temperature. The atmosphere in the reaction system was replaced with nitrogen three times. The reaction mixture was stirred at 10° C. for 1 h, and then cooled to rt. After filtration, concentration at reduced pressure was performed to obtain a crude product. Isolation and purification by column chromatography (silica gel, DCM:MeOH=10:1 as an eluant) were performed to obtain the targeted compound (230 mg, 43.47% yield, colorless oily substance). LC-MS (ESI): m/z (M+1) 232.17.

c) N,N-dimethyl-4-(4-methoxyphenyl)cyclohexan-1-amine: N,N-dimethyl-4'-methoxy-2,3,4,5-tetrahydro-[1,1'-biphenyl]-4-amine (230 mg, 0.99 mmol) was dissolved in ethanol (10 mL) at room temperature, and Pd/C (23 mg, w/w=10%) was added. The atmosphere in the reaction system was replaced with hydrogen three times. The reaction mixture was stirred at room temperature in hydrogen atmosphere overnight. After filtration, concentration at reduced pressure was performed to obtain a crude product. Isolation and purification by column chromatography (silica gel, DCM:MeOH=10:1 as an eluant) were performed to produce the targeted compound (212 mg, 91.38% yield, brown solid). LC-MS (ESI): m/z (M+1) 232.17.

d) 4-(4-(dimethylamino)cyclohexyl)phenol: N,N-dimethyl-4-(4-methoxyphenyl)cyclohexan-1-amine (212 mg, 0.92 mmol) was dissolved in anhydrous DCM (10 mL) at room temperature; and boron tribromide (115 μL, 2.76 mmol) was added dropwise while an ice-water bath was used. After the addition was completed, the temperature was raised to rt at which the reaction mixture was stirred for 1 h. Water (5 mL) was added to quench the reaction. DCM (20 mL) was added for extraction and separation. The aqueous phase was extracted with DCM (10 mL×2). The organic phases were combined, washed with a saturated saline solution (15 mL), dried with anhydrous sodium sulfate, and concentrated at reduced pressure to obtain a crude product. Isolation and purification by column chromatography (silica gel, DCM:MeOH=10:1 as an eluant) were performed to produce the targeted compound (130 mg, 65.24% yield, pale yellow liquid). LC-MS (ESI): m/z (M+1) 220.17.

e) 4-(4-((dimethylamino)cyclohexyl)phenyl)trifluoromethane sulfonate: 4-(4-(dimethylamino)cyclohexyl)phenol (130 mg, 0.6 mmol) was dissolved in DCM (4 mL) at room temperature, and N-phenylbis(trifluoromethylsulfonyl)imine (322 mg, 0.9 mmol), 4-dimethylaminopyridine (7 mg, 0.06 mmol) and triethylamine (126 μL, 1.16 mmol) were added. The reaction mixture was stirred at room temperature for 3 h. Concentration at reduced pressure was performed to obtain a crude product. Isolation and purification by column chromatography (silica gel, DCM:MeOH=10:1 as an eluant) were performed to produce the targeted compound (170 mg, 81.62% yield, pale yellow liquid). LC-MS (ESI): m/z (M+1) 352.11.

2) N,N-dimethyl-1-(4-bromo-2-fluorophenyl)piperidin-4-amine 4-bromo-2-fluorophenyl iodide (700 mg, 2.33 mmol), N,N-dimethylaminopiperidine (359 mg, 2.80 mmol), tris (dibenzylideneacetone)dipalladium (213 mg, 0.23 mmol), 4,5-bis(diphenylphosphino)-9,9-dimethylxanthene (270 mg, 0.47 mmol) and cesium carbonate (1.89 g. 5.83 mmol) were added to dioxane (15 mL) at room temperature. After the atmosphere in the reaction system was replaced with nitrogen three times, the reaction mixture was stirred overnight at 100° C. The reaction solution was cooled to rt filtered, and concentrated at reduced pressure to remove the organic solvent, thereby producing a crude product. Isolation and purification by column chromatography (silica gel, DCM:MeOH=15:1 as an eluant) were performed to produce the targeted compound (350 mg, 49% yield, yellow liquid). LC-MS (ESI): m/z (M+1) 301.32.

Other N,N-dimethyl-1-(4-bromo-substituted phenyl)piperidin-4-ylamines could be prepared in a way similar to synthesis of Intermediate 2), with N,N-dimethylaminopiperidine and corresponding 4-bromo-substituted phenyl iodides as starting materials.

3) N,N-dimethyl-1-(1-(4-bromophenyl)piperidin-4-yl)methylamine a) Tert-butyl 4-(hydroxymethyl)piperidine-1-carboxylate: 1-(tert-butoxy carbonyl) piperidine-4-carboxylate (5.0 g, 22 mmol) was dissolved in anhydrous THF (80 mL). After the temperature was lowered to 0° C., a solution of borane in THF (1M, 33 mL, 33 mmol) was added under the protection of nitrogen. After the addition was completed, the reaction mixture was stirred at 0° C. for 2 hours. A hydrochloric acid solution was added dropwise slowly (1M, 33 mL, 33 mmol). After the reaction mixture was stirred at 0° C. for 30 min, DCM (100 mL) was added to separate out the organic phase, and the aqueous phase was extracted with DCM (50 mL×2). The organic phases were combined, washed with a saturated saline solution, dried with anhydrous sodium sulfate, filtered, and concentrated at reduced pressure to obtain the targeted compound (3.8 g, 80% yield, colorless oil). LC-MS (ESI): m/z (M+1) 216.16.

b) Tert-butyl 4-((benzoyloxy)methyl)piperidine-1-carboxylate: Tert-butyl 4-(hydroxymethyl)piperidine-1-carboxylate (3.8 g, 17.7 mmol) was dissolved in DCM (80 mL) at room temperature, and triethylamine (3.5 g, 35.2 mmol) and 4-dimethylaminopyridine (108 mg, 0.88 mmol) were added in sequence. After the reaction mixture was cooled to 0° C., benzoyl chloride (2.5 g, 17.7 mmol) was added dropwise to the reaction solution. After the addition was completed, the reaction mixture was stirred at room temperature for 3 h. Water was added (40 mL). The organic phase was separated out, and the aqueous phase was extracted with DCM (50 mL×2). The organic phases were combined, washed with a saturated saline solution, dried with anhydrous sodium sulfate, filtered, and concentrated at reduced pressure to produce the targeted compound (3.0 g, 77% yield, colorless oil). LC-MS (ESI): m/z (M+1) 320.13.

c) Methyl (piperidin-4-yl)benzoate: Tert-butyl 4-((benzoyloxy)methyl)piperidine-1-carboxylate (3.0 g, 9.3 mmol) was dissolved in a solution of HCl in dioxane (4 M, 30 mL). After the reaction solution was stirred at room temperature for 1 h, the organic solvent was removed at reduced pressure. DCM (50 mL) was added to the resulting crude product. At 0° C., pH was adjusted to 7-8 by adding a sodium hydroxide solution. The organic phase was separated out, and the aqueous phase was extracted with DCM (50 mL×2). The organic phases were combined, washed with saturated saline solution, dried with anhydrous sodium sulfate, filtered, and concentrated at reduced pressure to produce the targeted compound (1.5 g, 73% yield, colorless oily substance). LC-MS (ESI): m/z (M+1) 220.13.

d) Methyl (1-(4-bromophenyl)piperidin-4-yl)benzoate: To a solution of methyl (piperidin-4-yl)benzoate (1.0 g, 4.6 mmol) in THF (30 mL) were added p-bromophenyl iodide (2.58 g, 9.1 mmol), 4,5-bis(diphenylphosphino)-9,9-dimethylxanthene (533 mg, 0.92 mmol) and tris(dibenzylidene)acetone dipalladium (148 mg, 0.46 mmol) in sequence. The atmosphere of the reaction system was replaced with nitrogen three times, and lithium bis(trimethyl)silylamide (1 M, 13.7 mL, 13.7 mmol) was added. After the reaction mixture was stirred at room temperature for 24 h, water (10 mL) was added to quench the reaction. DCM (50 mL) was used for extraction. The organic phase was separated out, and the aqueous phase was extracted with DCM (50 mL×2). The organic phases were combined, washed with a saturated saline solution, dried with anhydrous sodium sulfate, filtered, and concentrated at reduced pressure to produce the targeted compound (1.2 g, a crude product, pale yellow solid). This intermediate was not purified, and used directly for the next reaction step. LC-MS (ESI): m/z (M+1) 374.28.

e) (1-(4-bromophenyl)piperidin-4-yl)methanol: Methyl (1-(4-bromophenyl)piperidin-4-yl)benzoate (1.2 g crude product, 3.2 mmol) was added to a mixed solvent of EtOH (20 mL) and water (2 mL), and sodium hydroxide (256.0 mg, 6.4 mmol) was added. After the reaction mixture wa stirred at room temperature for 2 h, water (20 mL) and DCM (50 mL) were added to the reaction solution. The organic phase was separated out, and the aqueous phase was extracted with DCM (50 mL×2). The organic phases were combined, washed with a saturated saline solution, dried with anhydrous sodium sulfate, filtered, and concentrated at reduced pressure to obtain a crude product. Isolation and purification by column chromatography (PE:EA=1:1) were performed to produce the targeted compound (843 mg, 69% two-step yield, yellow solid). LC-MS (ESI): m/z (M+1) 270.17.

f) Methyl (1-(4-bromophenyl)piperidin-4-yl)methylbenzene sulfonate: (1-(4-bromophenyl)piperidin-4-yl)methanol (843 mg, 3.1 mmol) was added to DCM (20 mL), and 4-dimethylaminopyridine (38 mg, 0.3 mmol) and triethylamine (633 mg, 6.3 mmol) were added in sequence. At 0° C., p-toluenesulfonyl chloride (718 mg, 3.8 mmol) was added dropwise slowly. After the addition was completed, the reaction mixture was stirred at room temperature for 2 h. Water (20 mL) and DCM (50 mL) were added to the reaction solution. The organic phase was separated out, and the aqueous phase was extracted with DCM (50 mL×2). The organic phases were combined, washed with a saturated saline solution, dried with anhydrous sodium sulfate, filtered, and concentrated at reduced pressure to produce the targeted compound (681 mg, 52% yield, yellow solid). LC-MS (ESI): m/z (M+1) 424.35.

g) N,N-dimethyl-1-(1-(4-bromophenyl)piperidin-4-yl)methylamine: Methyl (1-(4-bromophenyl)piperidin-4-yl)methylbenzene sulfonate (681 mg, 1.6 mmol) was dissolved in THF (20 mL), and dimethylamine hydrochloride (656 mg, 8.0 mmol) and potassium carbonate (1.1 g, 8.0 mmol) were added in sequence. Under the protection of nitrogen, the reaction mixture was stirred at 50° C. for 24 h, and then the reaction solution was cooled to rt. Water (20 mL) and DCM (50 mL) were added, and the organic phase was separated out. The aqueous phase was extracted with DCM (50 mL×2). The organic phases were combined, washed with a saturated saline solution, dried with anhydrous sodium sulfate, filtered, and concentrated at reduced pressure to produce a crude product. Isolation and purification by column chromatography (DCM:MeOH=5:1) were performed to produce the targeted compound (240 mg, 52% yield, yellow solid). LC-MS (ESI): m/z (M+1) 297.35.

Intermediate N,N-dimethyl-1-(1-(4-bromophenyl)piperidin-4-yl)ethylamine could be prepared similar to the synthesis process in 3), with 1-(tert-butoxycarbonyl)piperidine-4-acetic acid, benzoyl chloride, p-bromophenyl iodide, p-methylbenzene sulfonyl chloride and dimethylamine hydrochloride as the starting materials.

Example 1

N,N-dimethyl-3-((5-(1-(tetrahydro-2H-pyran-4-yl)pyrido[2,3-e][1,2,4]triazolo[4,3-a]pyrazin-8-yl)pyridin-2-yl)oxy)propan-1-amine a) 2-hydroxy-7-bromopyrido[2,3-b]pyrazine: 2,3-diamino-5-bromopyridine (5.0 g, 26.6 mmol) and ethyl glyoxylate (50% toluene solution, 8.0 g, 39.9 mmol) were mixed in dioxane (100 mL). After the mixture was stirred at 120° C. for 1 h, the reaction solution was cooled to rt, and diethyl ether (500 mL) was added to dilute the reaction solution which was suction filtered to produce the targeted compound (4.5 g, 75% yield, yellow solid). LC-MS (ESI): m/z (M+1) 226.35.

b) 2-chloro-7-bromopyrido[2,3-b]pyrazine: 2-hydroxy-7-bromopyrido[2,3-b]pyrazine (500 mg, 2.2 mmol) was dissolved in phosphorus oxychloride (7 mL). After the mixture was stirred at 90° C. for 3 h, the reaction solution was cooled to rt, and then added dropwise to ice water slowly. The precipitated solid was filtered, and dried to produce the targeted compound (510 mg, 95% yield, yellow solid). LC-MS (ESI): m/z (M+1) 244.11.

c) 2-hydrazino-7-bromopyrido[2,3-b]pyrazine: 2-chloro-7-bromopyrido[2,3-b]pyrazine (500 mg, 2.05 mmol) was dissolved in ethanol (5 mL), and hydrazine hydrate (1.2 mL) was added. After the mixture was stirred at 80° C. for 1.5 h, the reaction solution was cooled to rt, and suction filtered. The filter cake was washed with a small amount of ethanol. After the solid was suction dried, the targeted compound was obtained (450 mg, 92% yield, pale yellow solid). LC-MS (ESI): m/z (M/M+2) 240.30/242.30.

d) 8-bromo-1-(tetrahydro-2H-pyran-4-yl)pyrido[2,3-e][1,2,4]triazolo[4,3-a]pyrazine: 2-hydrazino-7-bromopyrido[2,3-b]pyrazine (200 mg, 0.83 mmol) and tetrahydropyran-4-carbaldehyde (95 mg, 0.83 mmol) were mixed in methanol (4 mL). After the reaction solution was stirred at room temperature for 1 h, the solvent was removed at reduced pressure. The resulting crude product was dissolved in DCM (4 mL), and (diacetoxyiodo)benzene (400 mg, 1.24 mmol) was added. After the reaction solution was stirred at room temperature for 10 min, the reaction was quenched with a saturated aqueous solution of sodium bicarbonate (10 mL). EA (10 mL×3) was used for extraction and liquid separation. The organic phase was washed with a saturated saline solution, dried with anhydrous sodium sulfate, filtered, and concentrated at reduced pressure to produce a crude product. Isolation and purification by column chromatography (silica gel, DCM:MeOH=10:1 as an eluant) were performed to obtain the targeted compound (200 mg, 72% yield, pale yellow solid). LC-MS (ESI): m/z (M+1) 334.43.

e) N,N-dimethyl-3-((5-(1-(tetrahydro-2H-pyran-4-yl)pyrido[2,3-e][1,2,4]triazolo[4,3-a]pyrazin-8-yl)pyridin-2-yl)oxy)propan-1-amine: 8-bromo-1-(tetrahydro-2H-pyran-4-yl)pyrido [2,3-e][1,2,4]triazolo[4,3-a]pyrazine (30 mg, 0.09 mmol), (6-(3-(dimethylamino)propyl)pyridin-3-yl)boric acid (61 mg, 0.45 mmol), cesium carbonate (88 mg, 0.27 mmol) and [1,1'-bis(diphenylphosphino)ferrocene]-palladium(II) dichloride dichloromethane complex (8 mg, 0.009 mmol) were mixed in dioxane (2.5 mL) and water (0.5 mL). After the mixture was stirred at 100° C. for 1 h under the protection of nitrogen, the reaction solution was cooled to rt, and then subjected to extraction and liquid separation with EA and water. The organic phase was washed with a saturated saline solution, dried with anhydrous sodium sulfate, filtered, and concentrated at reduced pressure to obtain a crude product. Isolation and purification by preparative liquid chromatography (C18 column, 0-100% acetonitrile/water as a mobile phase) were performed to obtain the targeted compound (15 mg, 38% yield, white solid). LC-MS (ESI): m/z (M+1) 434.50. $^1$H NMR (400 MHz, DMSO-$d_6$): δ 9.55 (s, 1H), 9.25 (d, J=1.9 Hz, 1H), 8.75 (d, J=2.5 Hz, 1H), 8.69 (d, J=2.0 Hz, 1H), 8.29 (dd, J=8.7, 2.6 Hz, 1H), 7.06 (d, J=8.7 Hz, 1H), 4.45-4.37 (m, 2H), 4.33-4.25 (m, 1H), 4.06-3.94 (m, 2H), 3.77-3.68 (m, 2H), 2.46-2.41 (m, 2H), 2.21 (s, 6H), 2.18-1.82 (m, 6H).

Example 2

N,N-dimethyl-3-(4-(1-(tetrahydro-2H-pyran-4-yl)pyrido[2,3-e][1,2,4]triazolo[4,3-a]pyrazin-8-yl)phenoxy)propan-1-amine The above title compound was prepared using a synthesis process similar to that described with reference to Example 1 e, the starting materials being 8-bromo-1-(tetrahydro-2H-pyran-4-yl)pyrido[2,3-e][1,2,4]triazolo[4,3-a]pyrazine (Example 1 d) and N,N-dimethyl-3-(4-(4,4,5,5-tetramethyl-1,3,2-dioxaborolan-2-yl)phenoxy)propan-1-amine. LC-MS (ESI): m/z (M+1) 433.39. $^1$H NMR (400 MHz, DMSO-$d_6$): δ 9.53 (s, 1H), 9.22 (d, J=2.0 Hz, 1H), 8.63 (d, J=2.0 Hz, 1H), 7.88 (d, J=8.8 Hz, 2H), 7.18 (d, J=8.8 Hz, 2H), 4.27-4.21 (m, 1H), 4.11 (t, J=6.4 Hz, 2H), 4.06-4.00 (m, 2H), 3.71 (t, J=10.2 Hz, 2H), 2.39 (t, J=7.1 Hz, 2H), 2.23-2.09 (m, 8H), 2.07-1.99 (m, 2H), 1.93-1.86 (m, 2H).

Example 3

N,N-dimethyl-3-((5-(1-(tetrahydro-2H-pyran-4-yl)-[1,2,4]triazolo[4,3-a]quinoxalin-8-yl)pyridin-2-yl)oxy)propan-1-amine a) 2-hydroxy-7-bromoquinoxaline: 2-hydroxyquinoxaline (5 g, 34.2 mmol) was dissolved in acetic acid (50 mL), and liquid bromine (8.2 g, 51.2 mmol) was added dropwise slowly. After reaction under agitation at room temperature for 6 h, the reaction solution was suction filtered. The filter cake was washed with a small amount of diethyl ether. After the solid was suction dried, the targeted compound was obtained (6.1 g, 79% yield, yellow solid). LC-MS (ESI): m/z (M+1) 225.11.

b) 2-chloro-7-bromoquinoxaline: 2-hydroxy-7-bromoquinoxaline (3 g, 13.3 mmol) was dissolved in phosphorus oxychloride (25 mL), and DMF (3 drops) was added as a catalyst. After reaction under agitation at 120° C. for 3 h, the reaction solution was cooled to rt, and concentrated at reduced pressure. The resulting crude product was diluted with EA (50 mL), and added dropwise slowly to a saturated aqueous solution of sodium bicarbonate (200 mL). Liquid separation and extraction were performed. The organic phase was washed with a saturated saline solution, dried with anhydrous sodium sulfate, filtered, and concentrated at reduced pressure to obtain a crude product. Isolation and purification by column chromatography (silica gel, PE:EA=2:1 as an eluant) were performed to obtain the targeted compound (1.3 g, 40% yield, yellow solid). LC-MS (ESI): m/z (M+1) 243.20.

c) 2-hydrazino-7-bromoquinoxaline: 2-chloro-7-bromoquinoxaline (1.3 g, 5.3 mmol) was dissolved in ethanol (15 mL), and hydrazine hydrate (2.0 mL) was added. After the mixture was stirred at 80° C. for 1 h, the reaction solution was cooled to rt, and suction filtered. The filter cake was washed with a small amount of ethanol. After the solid was suction dried, the targeted compound was obtained (1.2 g, 95% yield, white solid). LC-MS (ESI): m/z (M+1) 239.10.

d) 8-bromo-1-(tetrahydro-2H-pyran-4-yl)-[1,2,4]triazolo[4,3-a]quinoxaline: 2-hydrazino-7-bromoquinoxaline (200 mg, 0.83 mmol) and tetrahydropyran-4-carbaldehyde (95 mg, 0.83 mmol) were mixed in methanol (4 mL). The reaction solution was stirred at room temperature for 1 h, and then the solvent was removed at reduced pressure. The resulting crude product was dissolved in DCM (10 mL), and iodosobenzene diacetate (400 mg, 1.24 mmol) was added. After the reaction solution was stirred at room temperature for 10 min, the reaction was quenched with a saturated aqueous solution of sodium bicarbonate (10 mL). EA (10 mL×3) was used for extraction and liquid separation. The organic phase was washed with a saturated saline solution, dried with anhydrous sodium sulfate, filtered, and concentrated at reduced pressure to obtain a crude product. Isolation and purification by column chromatography (silica gel, DCM:MeOH=20:1 as an eluant) was performed to obtain the targeted compound (250 mg, 90% yield, yellow solid). LC-MS (ESI): m/z (M+1) 333.20.

e) N,N-dimethyl-3-((5-(1-(tetrahydro-2H-pyran-4-yl)-[1,2,4]triazolo[4,3-a]quinoxalin-8-yl)pyridin-2-yl)oxy)propan-1-amine: 8-bromo-1-(tetrahydro-2H-pyran-4-yl)-[1,2,4]triazolo[4,3-a]quinoxaline (25 mg, 0.075 mmol), (6-(3-(dimethylamino)propyl)pyridin-3-yl)boronic acid (50 mg, 0.22 mmol), cesium carbonate (75 mg, 0.23 mmol) and [1,1'-bis(diphenylphosphino)ferrocene]-palladium(II) dichloride dichloromethane complex (7 mg, 0.0075 mmol) were mixed in dioxane (2.5 mL) and water (0.5 mL). After reaction under agitation at 100° C. for 1 h under the protection of nitrogen, the reaction solution was cooled to rt, and then subjected to extraction and liquid separation with EA (5 mL) and water (5 mL). The organic phase was washed with a saturated saline solution, dried with anhydrous sodium sulfate, filtered, and concentrated at reduced pressure to obtain a crude product. Isolation and purification by preparative liquid chromatography (C18 column, 0-100% acetonitrile/water as a mobile phase) were performed to obtain the targeted compound (13 mg, 40% yield, white solid). LC-MS (ESI): m/z (M+1) 433.55. $^1$H NMR (400 MHz, DMSO-d$_6$): δ 9.33 (s, 1H), 8.66 (d, J=2.5 Hz, 1H), 8.33 (s, 1H), 8.20 (s, 1H), 8.18 (s, 1H), 8.04 (d, J=8.5 Hz, 1H), 7.02 (d, J=8.6 Hz, 1H), 4.38 (t, J=6.6 Hz, 2H), 4.29-4.20 (m, 1H), 4.06-3.99 (m, 2H), 3.75-3.67 (m, 2H), 2.42-2.35 (m, 2H), 2.26-2.14 (m, 8H), 2.09-1.99 (m, 2H), 1.95-1.85 (m, 2H).

Example 4

N,N-dimethyl-3-(4-(1-(tetrahydro-2H-pyran-4-yl)-[1,2,4]triazolo[4,3-a]quinoxalin-8-yl)phenoxy)propan-1-amine The above title compound was prepared using a synthesis process similar to that described with reference to Example 3 e, the starting materials being N,N-dimethyl-3-(4-(4,4,5,5-tetramethyl-1,3,2-dioxaborolan-2-yl)phenoxy)propan-1-amine and 8-bromo-1-(tetrahydro-2H-pyran-4-yl)-[1,2,4]triazolo[4,3-a]quinoxaline (Example 3 d). LC-MS (ESI): m/z (M+1) 432.65. $^1$H NMR (400 MHz, DMSO-d$_6$): δ 9.30 (s, 1H), 8.30 (d, J=1.6 Hz, 1H), 8.16 (d, J=8.4 Hz, 1H), 8.01 (dd, J=8.5, 1.7 Hz, 1H), 7.79 (d, J=8.8 Hz, 2H), 7.14 (d, J=8.8 Hz, 2H), 4.21-4.15 (m, 1H), 4.13-4.03 (m, 4H), 3.73-3.65 (m, 2H), 2.49-2.46 (m, 2H), 2.24 (s, 6H), 2.22-2.16 (m, 2H), 2.10-1.99 (m, 2H), 1.96-1.89 (m, 2H).

Example 5

N,N-dimethyl-3-((6-(1-(tetrahydro-2H-pyran-4-yl)-[1,2,4]triazolo[4,3-a]quinoxalin-8-yl)pyridin-3-yl)oxy)propan-1-amine a) 1-(tetrahydro-2H-pyran-4-yl)-8-(4,4,5,5-tetramethyl-1,3,2-dioxaborolan-2-yl)[1,2,4]triazolo[4,3-a]quinoxaline: 8-bromo-1-(tetrahydro-2H-pyran-4-yl)-[1,2,4]triazolo[4,3-a]quinoxaline (310 mg, 0.93 mmol), bis(pinacolato)diboron (353 mg, 1.39 mmol), potassium acetate (275 mg, 2.81 mmol) and [1,1'-bis(diphenylphosphino)ferrocene]-palladium(II) dichloride (76 mg, 0.093 mmol) were added to dioxane (15 mL). After reaction under agitation at 90° C. for 16 h under the protection of nitrogen, the reaction mixture was cooled to rt, and filtered. The filtrate was concentrated at reduced pressure to obtain a crude product. Isolation and purification by column chromatography (silica gel, DCM:MeOH=10:1 as an eluant) was performed to obtain the targeted compound (300 mg, 85% yield, yellow solid). LC-MS (ESI): m/z (M+1) 381.30.

b) N,N-dimethyl-3-((6-(1-(tetrahydro-2H-pyran-4-yl)-[1,2,4]triazolo[4,3-a]quinoxalin-8-yl)pyridin-3-yl)oxy)propan-1-amine: N,N-dimethyl-3-((6-bromopyrid-3-yl)oxy)propan-1-amine (50 mg, 0.19 mmol), 1-(tetrahydro-2H-pyran-4-yl)-8-(4,4,5,5-tetramethyl-1,3,2-dioxaborolan-2-yl)-[1,2,4]triazolo[4,3-a]quinoxaline (73 mg, 0.19 mmol), cesium carbonate (125 mg, 0.38 mmol) and [1,1'-bis(diphenylphosphino)ferrocene]-palladium(II) dichloride (15 mg, 0.02 mmol) were added to a mixed solvent of dioxane (2.5 mL) and water (0.5 mL). After reaction under agitation at 90° C. for 2 h under the protection of nitrogen, the reaction mixture was cooled to rt, suction filtered, and concentrated at reduced pressure to obtain a crude product. Isolation and purification by preparative liquid chromatography (C18 column, 0-100% acetonitrile/water as a mobile phase) were performed to obtain the targeted compound (8 mg, 23% yield, white solid). LC-MS (ESI): m/z (M+1) 433.35. $^1$H NMR (400 MHz, CDCl$_3$): δ 9.25 (s, 1H), 9.07 (d, J=1.2 Hz, 1H), 8.46 (d, J=2.7 Hz, 1H), 8.19 (d, J=8.5 Hz, 1H), 8.12 (dd, J=8.4 Hz, 1.5 Hz, 1H), 7.84 (d, J=8.7 Hz, 1H), 7.36 (dd, J=8.8 Hz, 2.9 Hz, 1H), 4.29-4.21 (m, 2H), 4.18 (t, J=6.3 Hz, 2H), 3.99-3.92 (m, 1H), 3.86-3.78 (m, 2H), 2.58 (t, J=7.1 Hz, 2H), 2.43-2.23 (m, 10H), 2.10-2.05 (m, 2H).

Examples 6-10 and 12-19 were carried out using a synthesis process similar to that described with reference to Example 5, the starting materials being 1-(tetrahydro-2H-pyran-4-yl)-(4,4,5,5-tetramethyl-1,3,2-dioxaborolan-2-yl)[1,2,4]triazolo[4,3-a]quinoxaline and corresponding substituted aryl or heteroaryl groups. The compound of Example 11 was prepared by reacting the compound of Example 10 with paraformaldehyde in formic acid under heating.

Examples 20-22 were carried out using a synthesis process similar to that described with reference to Example 3, the starting materials being N,N-dimethyl-3-(4-(4,4,5,5-tetramethyl-1,3,2-dioxaborolan-2-yl)phenoxy)propan-1-amine and corresponding 8-bromo-1-substituted-[1,2,4]triazolo[4,3-a]quinoxalines.

The following compounds can also be prepared by those skilled in the art according to known methods.

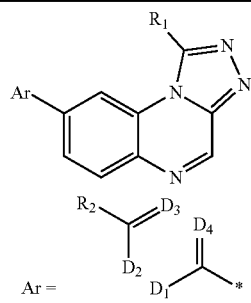

| Example | Ar | R₁ | LC-MS (ESI) | ¹H NMR, 400 MHz |
|---|---|---|---|---|
| 6 | (dimethylamino)propoxy-pyrimidin-5-yl | tetrahydropyran-4-yl | (M + 1) 434.70 | DMSO-d₆: δ 9.36 (s, 1H), 9.11 (s, 2H), 8.40 (d, J = 1.4 Hz, 1H), 8.22 (d, J = 9.0 Hz, 1H), 8.11 (dd, J = 8.4, 1.6 Hz, 1H), 4.45 (t, J = 6.6 Hz, 2H), 4.33-4.26 (m, 1H), 4.05-3.98 (m, 2H), 3.76-3.70 (m, 2H), 2.42 (t, J = 7.1 Hz, 2H), 2.30-2.09 (m, 8H), 2.09-1.99 (m, 2H), 1.98-1.89 (m, 2H) |
| 7 | (dimethylamino)propoxy-pyrimidin-2-yl | tetrahydropyran-4-yl | (M + 1) 434.56 | DMSO-d₆: δ 9.37 (s, 1H), 9.22 (d, J = 0.9 Hz, 1H), 8.77 (s, 2H), 8.59 (dd, J = 8.5, 1.3 Hz, 1H), 8.22 (d, J = 8.5 Hz, 1H), 4.28 (t, J = 6.4 Hz, 2H) 4.15-4.07 (m, 2H), 4.02-3.95 (m, 1H), 3.73 (t, J = 10.9 Hz, 2H), 2.41 (t, J = 7.0 Hz, 2H), 2.28-2.12 (m, 8H), 2.12-2.01 (m, 2H), 1.98-1.88 (m, 2H) |
| 8 | (dimethylamino)propoxy-pyrazin-2-yl | tetrahydropyran-4-yl | (M + 1) 434.55 | DMSO-d₆: δ 9.35 (s, 1H), 9.02 (s, 1H), 8.87 (s, 1H), 8.50 (s, 1H), 8.39 (d, J = 7.4 Hz, 1H), 8.21 (d, J = 8.5 Hz, 1H), 4.43 (t, J = 6.6 Hz, 2H), 4.12-4.03 (m, 3H), 3.71 (t, J = 10.7 Hz, 2H), 2.43 (t, J = 7.0 Hz, 2H), 2.23-2.14 (m, 8H), 2.10-2.01 (m, 2H), 1.98-1.90 (m, 2H) |
| 9 | (dimethylamino)ethoxy-phenyl | tetrahydropyran-4-yl | (M + 1) 418.76 | DMSO-d₆: δ 9.31 (s, 1H), 8.30 (d, J = 1.2 Hz, 1H), 8.16 (d, J = 8.4 Hz, 1H), 8.02 (dd, J = 8.5, 1.5 Hz, 1H), 7.80 (d, J = 8.7 Hz, 2H), 7.16 (d, J = 8.7 Hz, 2H), 4.26-4.11 (m, 3H), 4.11-3.99 (m, 2H), 3.74-3.66 (m, 2H), 2.68 (t, J = 5.8 Hz, 2H), 2.25 (s, 6H), 2.22-2.14 (m, 2H), 2.12-1.99 (m, 2H) |
| 10 | (dimethylamino)propyl-NH-phenyl | tetrahydropyran-4-yl | (M + 1) 431.47 | CDCl₃: δ 9.25 (s, 1H), 8.24 (s, 1H), 8.10 (d, J = 8.5 Hz, 1H), 7.95 (dd, J = 8.6, 1.5 Hz, 1H), 7.64 (d, J = 8.7 Hz, 1H), 6.77 (d, J = 8.7 Hz, 1H), 6.15 (brs, 1H), 4.19-4.12 (m, 1H), 4.10-4.01 (m, 2H), 3.69 (t, J = 10.5 Hz, 2H), 3.23-3.09 (m, 4H), 2.78 (s, 6H), 2.23-2.14 (m, 2H), 2.11-2.00 (m, 2H), 1.97-1.87 (m, 2H). |
| 11 | (dimethylamino)propyl-N(Me)-phenyl | tetrahydropyran-4-yl | (M + 1) 445.30 | DMSO-d₆: δ 9.24 (s, 1H), 8.28 (d, J = 1.5 Hz, 1H), 8.10 (d, J = 8.5 Hz, 1H), 7.98 (dd, J = 8.5, 1.6 Hz, 1H), 7.70 (d, J = 8.9 Hz, 2H), 6.89 (d, J = 8.9 Hz, 2H), 4.20-4.14 (m, 1H), 4.09-4.03 (m, 2H), 3.74-3.67 (m, 2H), 3.44 (t, J = 7.2 Hz, 2H), 2.98 (s, 3H), 2.26 (t, J = 6.9 Hz, 2H), 2.22-2.12 (m, 8H), 2.09-2.01 (m, 2H), 1.72-1.64 (m, 2H) |

-continued
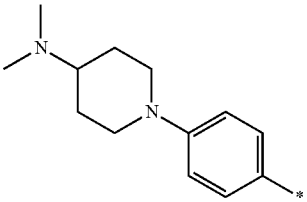 [SMILES: *c1ccc(N2CCC(N(C)C)CC2)cc1]
| Example | Ar | R₁ | LC-MS (ESI) | ¹H NMR, 400 MHz |
|---|---|---|---|---|
| 12 | 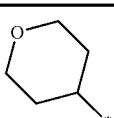 | 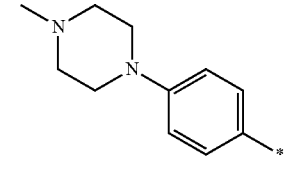 [SMILES: *c1ccc(N2CCN(C)CC2)cc1] | (M + 1) 457.57 | DMSO-d₆: δ 9.28 (s, 1H), 8.30 (s, 1H), 8.15 (d, J = 4.8 Hz, 1H), 8.00 (dd, J = 8.7 Hz, 1.2 Hz, 1H), 7.73 (d, J = 8.8 Hz, 2H), 7.15 (d, J = 8.8 Hz, 2H), 4.21-4.14 (m, 1H), 4.12-4.02 (m, 2H), 4.00-3.89 (m, 2H), 3.70 (t, J = 10.6 Hz, 2H), 2.9-2.7 (m, 3H), 2.48 (s, 6H), 2.26-2.14 (m, 2H), 2.13-1.91 (m, 4H), 1.67-1.53 (m, 2H) |
| 13 | 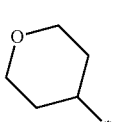 | 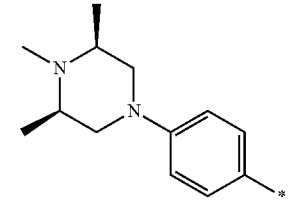 [SMILES: *c1ccc(N2C[C@@H](C)N(C)[C@@H](C)C2)cc1] | (M + 1) 429.46 | DMSO-d₆: δ 9.27 (s, 1H), 8.32-8.28 (m, 1H), 8.13 (d, J = 8.5 Hz, 1H), 8.01 (dd, J = 8.4 Hz, 1.6 Hz, 1H), 7.72 (d, J = 8.8 Hz, 2H), 7.13 (d, J = 8.8 Hz 2H) 4.21-4.15 (m, 1H), 4.09-4.03 (m, 2H), 3.70 (t, J = 9.6 Hz, 2H), 3.27 (t, J = 5.0 Hz, 4H), 2.48-2.44 (m, 4H), 2.24 (s, 3H), 2.22-2.16 (m, 2H), 2.09-2.01 (m, 2H) |
| 14 | 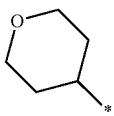 [SMILES: *C1CCOCC1] | 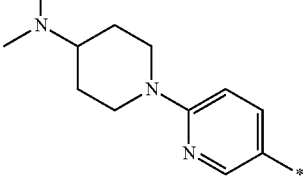 | (M + 1) 457.42 | CDCl₃: δ 9.23 (s, 1H), 8.21 (s, 1H), 8.17 (d, J = 8.4 Hz, 1H), 7.87 (dd, J = 8.4, 1.5 Hz, 1H), 7.59 (d, J = 8.7 Hz, 2H), 7.07 (d, J = 8.7 Hz, 2H), 4.28-4.20 (m, 2H), 3.87-3.80 (m, 1H), 3.77-3.69 (m, 2H), 3.68-3.61 (m, 2H), 3.05-2.75 (m, 4H), 2.54 (s, 3H), 2.42-2.27 (m, 4H), 1.37 (d, J = 3.8 Hz, 6H) |
| 15 | 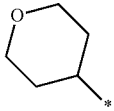 [SMILES: *C1CCOCC1] | 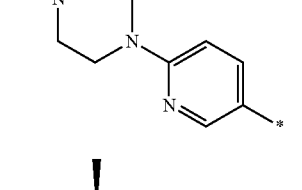 | (M + 1) 458.38 | CDCl₃: δ 9.23 (s, 1H), 8.52-8.49 (m, 1H), 8.21-8.16 (m, 2H), 7.83-7.75 (m, 2H), 6.83 (d, J = 8.8 Hz, 1H), 4.59-4.48 (m, 2H), 4.26-4.21 (m, 2H), 3.86-3.80 (m, 1H), 3.78-3.71 (m, 2H), 3.02-2.93 (m, 2H), 2.81-2.73 (m, 1H), 2.49 (s, 6H), 2.39-2.27 (m, 4H), 2.12-2.08 (m, 2H), 1.70-1.61 (m, 2H) |
| 16 | 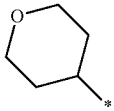 [SMILES: *C1CCOCC1] | 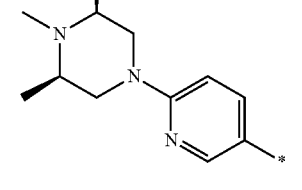 | M.W. 429.53 | — |
| 17 | 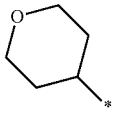 |  | M.W. 457.58 | — |

-continued

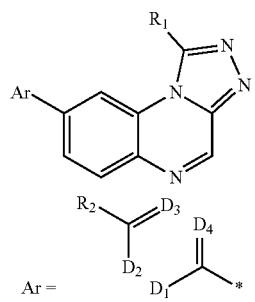

Ar =

| Example | Ar | R₁ | LC-MS (ESI) | ¹H NMR, 400 MHz |
|---|---|---|---|---|
| 18 | dimethylamino-cyclohexyl-phenyl | | (M + 1) 456.44 | DMSO-$d_6$: δ 9.32 (s, 1H), 8.37 (d, J = 1.2 Hz, 1H), 8.19 (d, J = 8.4 Hz, 1H), 8.05 (dd, J = 1.6 Hz, 1H), 7.77 (d, J = 8.2 Hz, 2H), 7.45 (d, J = 8.2 Hz, 2H), 4.23-4.17 (m, 1H), 4.10-4.02 (m, 2H), 3.76-3.67 (m, 2H), 2.75-2.68 (m, 1H), 2.24-2.13 (m, 7H), 2.11-1.81 (m, 8H), 1.61-1.48 (m, 4H) |
| 19 | dimethylamino-cyclohexyl-pyridyl | tetrahydropyran-4-yl | M.W. 456.59 | — |
| 20 | dimethylamino-propoxy-phenyl | piperidin-1-yl | (M + 1) 431.40 | DMSO-$d_6$: δ 9.16 (s, 1H), 8.67 (d, J = 1.8 Hz, 1H), 8.08 (d, J = 8.4 Hz, 1H), 7.93 (dd, J = 8.5, 1.9 Hz, 1H), 7.73 (d, J = 8.7 Hz, 2H), 7.14 (d, J = 8.8 Hz, 2H), 4.09 (t, J = 6.4 Hz, 2H), 3.56-3.45 (m, 2H), 3.09-2.97 (m, 2H), 2.40 (t, J = 7.1 Hz, 2H), 2.17 (s, 6H), 1.93-1.82 (m, 5H), 1.79-1.69 (m, 2H), 1.52-1.44 (m, 1H) |
| 21 | dimethylamino-propoxy-phenyl | morpholin-4-yl | (M + 1) 433.26 | DMSO-$d_6$: δ 9.19 (s, 1H), 8.72 (d, J = 1.9 Hz, 1H), 8.10 (d, J = 8.4 Hz, 1H), 7.95 (dd, J = 8.5, 1.9 Hz, 1H), 7.74 (d, J = 8.8 Hz, 2H), 7.15 (d, J = 8.8 Hz, 2H), 4.10 (t, J = 6.4 Hz, 2H), 4.06-3.92 (m, 2H), 3.89-3.75 (m, 2H), 3.44-3.35 (m, 4H), 2.41 (t, J = 7.1 Hz, 2H), 2.18 (s, 6H), 1.93-1.85 (m, 2H) |
| 22 | dimethylamino-propoxy-phenyl | 4-methylpiperazin-1-yl | (M + 1) 446.39 | DMSO-$d_6$: δ 9.18 (s, 1H), 8.72 (d, J = 1.7 Hz, 1H), 8.09 (d, J = 8.4 Hz, 1H), 7.94 (dd, J = 8.5, 1.9 Hz, 1H), 7.75 (d, J = 8.8 Hz, 2H), 7.14 (d, J = 8.8 Hz, 2H), 4.10 (t, J = 6.3 Hz, 2H), 3.49-3.40 (m, 2H), 3.25-3.15 (m, 2H), 2.99-2.84 (m, 2H), 2.56-2.52 (m, 2H), 2.36-2.22 (m, 11H), 1.97-1.90 (m, 2H) |

Example 23

N,N-dimethyl-3-(4-(1-((3S,5R)-3,4,5-trimethylpiperazin-1-yl)-[1,2,4]triazolo[4,3-a]quinoxalin-8-yl)phenoxy)propan-1-amine a) Tert-butyl (2R,6S)-4-(chloroformyl)-2,6-dimethylpiperazine-1-carbonate: Triphosgene (1.3 g, 4.4 mmol) was dissolved in anhydrous DCM (20 mL), and pyridine (1.03 g, 13.0 mmol) was added. After the reaction mixture was cooled to 0° C., a solution of tert-butyl (2R,6S)-2,6-dimethylpiperazine-1-carbonate (1.4 g, 6.5 mmol) in DCM (5 mL) was added dropwise to the reaction system slowly. After the addition was completed, the temperature of the reaction solution was raised to rt at which agitation was maintained for 6 h. Diluted hydrochloric acid (1 M, 50 mL) was added to the reaction solution, and the resulting mixture was subjected to extraction with DCM (30 mL×2). The combined organic phase was dried with anhydrous sodium sulfate, and concentrated at reduced pressure to remove the organic solvent to obtain a product (1.41 g, 100% yield, yellow liquid). This product was not purified, and used directly for the next reaction step.

b) Tert-butyl (2R,6S)-4-(2-(7-bromoquinoxalin-2-yl)hydrazino-1-formyl)-2,6-dimethyl piperazine-1-carbonate: 7-bromo-2-hydrazinoquinoxaline (700 mg, 2.93 mmol) was dissolved in anhydrous DCM (10 mL) at room temperature, and N,N-di-isopropylethylamine (1.6 mL, 8.8 mmol) was added. Tert-butyl (2R,6S)-4-(chloroformyl)-2,6-dimethylpiperazine-1-carbonate (1.23 g, 4.4 mmol) was added to the reaction system. After the reaction mixture was stirred at room temperature for 3 days, a saturated aqueous solution of sodium bicarbonate (20 mL) was added. After liquid separation, the aqueous phase was extracted with DCM (50 mL). The organic phases were combined, washed with a saturated saline solution, dried with anhydrous sodium sulfate, filtered, and concentrated at reduced pressure to remove the organic solvent to obtain a crude compound. Isolation and purification by column chromatography (silica gel, PE:EA=5:1 as an eluant) were performed to obtain the targeted compound (480 mg, 35% yield, white solid). LC-MS (ESI): m/z (M+1) 479.17.

c) 8-bromo-1-((2R,6S)-3,5-dimethylpiperazin-1-yl)-[1,2,4]triazolo[4,3-a]quinoxaline: Tert-butyl (2R,6S)-4-(2-(7-bromoquinoxalin-2-yl)hydrazino-1-formyl)-2,6-dimethylpiperazine-1-carbonate (480 mg, 1.0 mmol) was dissolved in phosphorus oxychloride (5 mL) at room temperature. After reaction under agitation at 100° C. for 1 h, the reaction mixture was concentrated at reduced pressure to remove phosphorus oxychloride. A saturated solution of sodium bicarbonate (10 mL) was added to quench the reaction, and EA (20 mL) was used for extraction. The organic phase was washed with a saturated saline solution, dried with anhydrous sodium sulfate and filtered. The organic solvent was removed at reduced pressure to obtain a crude compound. Isolation and purification by column chromatography (silica gel, PE:EA=5:1 as an eluant) were performed to obtain the targeted compound (228 mg, 63% yield, white solid). LC-MS (ESI): m/z (M+1) 361.11.

d) 8-bromo-1-((2R,6S)-3,4,5-trimethylpiperazin-1-yl)-[1,2,4]triazolo[4,3-a]quinoxaline: 8-bromo-1-((2R,6S)-3,5-dimethylpiperazin-1-yl)-[1,2,4]triazolo[4,3-a]quinoxaline (228 g, 0.63 mmol) was dissolved in methanol (2 mL) at room temperature, followed by addition of formic acid and 40% formalin in sequence. After reaction under agitation at 70° C. for 40 h, the reaction mixture was concentrated at reduced pressure to remove the solvent. A saturated solution of sodium carbonate (10 mL) was added to quench the reaction, and EA (20 mL) was used for extraction. The organic phase was washed with a saturated saline solution, dried with anhydrous sodium sulfate and filtered. The organic solvent was removed at reduced pressure to obtain a crude compound. Isolation and purification by column chromatography (silica gel, PE:EA=5:1 as an eluant) were performed to obtain the targeted compound (162 mg, 68% yield, white solid). LC-MS (ESI): m/z (M+1) 375.14.

e) N,N-dimethyl-3-(4-(1-((2R,6S)-3,4,5-trimethylpiperazin-1-yl)-[1,2,4]triazolo[4,3-a]quinoxalin-8-yl)phenoxy)propan-1-amine: 8-bromo-1-((2R,6S)-3,4,5-trimethylpiperazin-1-yl)-[1,2,4]triazolo[4,3-a]quinoxaline (100 mg, 0.27 mmol), 3-(N,N-dimethylamino)propoxyphenylboronic acid pinacol ester (165 mg, 0.54 mmol), [1,1'-bis(diphenylphosphino)ferrocene]-palladium(II) dichloride (22 mg, 0.027 mmol) and cesium carbonate (176 mg, 0.54 mmol) were added to a mixed solvent of dioxane (2 mL) and water (0.5 mL) at room temperature, and the reaction atmosphere was replaced with nitrogen three times. The reaction mixture was allowed to undergo microwave reaction at 100° C. for 1 h, and then cooled to rt. After filtration, the organic solvent was removed at reduced pressure to obtain a crude product. Isolation and purification by preparative liquid chromatography (C18 column, 0-100% acetonitrile/water as a mobile phase) were performed to obtain the targeted compound (20 mg, 15% yield, yellow solid). LC-MS (ESI): m/z (M+1) 474.12. $^1$H NMR (400 MHz, DMSO-$d_6$): δ 9.16 (s, 1H), 8.70 (m, 1H), 8.06 (d, J=8.4 Hz, 1H), 7.92 (d, J=8.4 Hz, 1H), 7.70 (d, J=8.4 Hz, 2H), 7.12 (d, J=8.7 Hz, 2H), 4.10 (t, J=6.3 Hz, 2H), 3.54-3.29 (m, 4H), 2.93-2.78 (m, 2H), 2.57-2.52 (m, 2H), 2.30-2.23 (m, 9H), 1.96-1.89 (m, 2H), 1.10 (s, 6H).

Examples 24-25 and 27-28 were carried out using a synthesis process similar to that described with reference to Example 3, the starting materials being (6-(3-(dimethylamino)propyl)pyrid-3-yl)boronic acid and corresponding 8-bromo-1-substituted-[1,2,4]triazolo[4,3-a]quinoxalines.

Example 26 was carried out using a synthesis process similar to that described with reference to Example 23, the starting materials being (6-(3-(dimethylamino)propyl)pyridin-3-yl)boronic acid and 8-bromo-1-((2R,6S)-3,4,5-trimethylpiperazin-1-yl)-[1,2,4]triazolo[4,3-a]quinoxaline.

In Example 29, N,N-dimethyl-3-(4-(1-(1-((2-(trimethylsilyl)ethoxy)methyl)-1H-imidazol-4-yl)-(1,2,4)triazolo[4,3-a]quinoxalin-8-yl)phenoxy)propan-1-amine was firstly prepared using a synthesis process similar to that described with reference to Example 3, and then this intermediate was subjected to deprotection reaction at room temperature in DCM under an acidic condition in the presence of hydrochloric acid/dioxane to obtain the targeted compound N,N-dimethyl-3-(4-(1-(1H-imidazol-4-yl)-[1,2,4]triazolo[4,3-a]quinoxalin-8-yl)phenoxy)propan-1-amine.

The following compounds can also be prepared by those skilled in the art according to known methods.

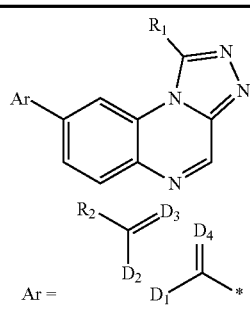

| Example | Ar | R₁ | LC-MS (ESI) | ¹H NMR, 400 MHz |
|---|---|---|---|---|
| 24 | dimethylamino-propoxy-pyridyl | morpholinyl | M.W. 433.52 | — |
| 25 | dimethylamino-propoxy-pyridyl | 4-methylpiperazinyl | M.W. 446.56 | — |
| 26 | dimethylamino-propoxy-pyridyl | (2S,5R)-1,2,5-trimethylpiperazinyl | (M + 1) 475.23 | DMSO-d₆: δ 9.20 (s, 1H), 8.77-8.63 (m, 1H), 8.58 (d, J = 2.1 Hz, 1H), 8.14-8.05 (m, 2H), 7.97 (dd, J = 8.4, 1.8 Hz, 1H), 7.02 (d, J = 8.6 Hz, 1H), 4.37 (t, J = 6.6 Hz, 2H), 3.43-3.40 (m, 2H), 2.93-2.75 (m, 2H), 2.49-2.43 (m, 2H), 2.38 (t, J = 7.1 Hz, 2H), 2.26 (s, 3H), 2.16 (s, 6H), 1.93-1.86 (m, 2H), 1.15-0.99 (m, 6H). |
| 27 | dimethylamino-propoxy-phenyl | morpholinomethyl | (M + 1) 447.26 | CDCl₃: δ 9.24 (s, 1H), 8.83 (d, J = 1.8 Hz, 1H), 8.18 (d, J = 8.4 Hz, 1H), 7.88 (dd, J = 8.4, 1.8 Hz, 1H), 7.65 (d, J = 8.8 Hz, 2H), 7.04 (d, J = 8.8 Hz, 2H), 4.31 (s, 2H), 4.11 (t, J = 6.4 Hz, 2H), 3.73 (t, J = 4.2 Hz, 4H), 2.69 (t, J = 4.4 Hz, 4H), 2.58 (t, J = 7.1 Hz, 2H), 2.35 (s, 6H), 2.09-2.02 (m, 2H) |
| 28 | dimethylamino-propoxy-phenyl | imidazol-1-yl | M.W. 413.49 | — |
| 29 | dimethylamino-propoxy-phenyl | imidazol-4-yl | (M + 1) 414.35 | DMSO-d₆: δ 12.94 (brs, 1H), 9.34 (s, 1H), 9.24 (s, 1H), 8.21 (s, 1H), 8.11 (d, J = 8.5 Hz, 1H), 8.05-7.91 (m, 2H), 7.68 (d, J = 8.5 Hz, 2H), 7.08 (d, J = 8.5 Hz, 2H), 4.07 (t, J = 6.2 Hz, 2H), 2.40 (t, J = 7.1 Hz, 2H), 2.18 (s, 6H), 1.94-1.84 (m, 2H) |

Example 30

N,N-dimethyl-3-(4-(1-(tetrahydro-2H-pyran-4-yl)pyrido[3,4-e][1,2,4]triazolo[4,3-a]pyrazin-8-yl)phenoxy)propan-1-amine The above title compound was prepared using a synthesis process similar to that described with reference to Example 1, the starting materials being 3,4-diamino-6-chloropyridine, ethyl gly oxalate, hydrazine hydrate, tetrahydropyran-4-carbaldehyde and 3-(N,N-dimethylamino)propoxyphenylboronic acid pinacol ester. LC-MS (ESI): m/z (M+H)$^+$ 433.07. $^1$H NMR (400 MHz, DMSO-d$_6$): δ 9.36 (s, 1H), 9.34 (s, 1H), 8.33 (s, 1H), 8.16 (d, J=8.4 Hz, 2H), 7.14 (d, J=8.4 Hz, 2H), 4.32-4.23 (m, 1H), 4.18-4.08 (m, 2H), 4.08-3.97 (m, 2H), 3.77 (t, J=10.6 Hz, 2H), 2.38 (t, J=6.8 Hz, 2H), 2.23-2.13 (m, 7H), 2.11-1.95 (m, 3H), 1.94-1.84 (m, 2H).

Example 31

N,N-dimethyl-3-(4-(9-(tetrahydro-2H-pyran-4-yl)pyrido[3,2-e][1,2,4]triazolo[4,3-a]pyrazin-2-yl)phenoxy)propan-1-amine a) 3-hydrazino-6-chloropyrido[2,3-b]pyrazine: 6-chloropyrido[2,3-b]pyrazin-3(4H)-one (480 mg, 2.65 mmol) was dissolved in N,N-dimethyl formamide (10 mL) at room temperature, and benzotriazol-1-yl-oxytripyrrolidinophosphonium hexafluorophosphate (PyBOP, 1.51 g, 2.91 mmol) and N,N-di-isopropyl ethylamine (DIPEA, 0.67 mL, 3.98 mmol) were added in sequence. After reaction under agitation at room temperature for 30 min, the reaction mixture was cooled to 0° C., and hydrazine hydrate (0.17 mL, 2.91 mmol) was added. The reaction mixture was continued to stirred at 0° C. for 30 min. A saturated aqueous solution of sodium bicarbonate (10 mL) was added to precipitate a solid which was suction filtered. The filter cake was washed with water (5 mL), and dried to obtain the targeted compound (480 mg, 92% yield, yellow solid). LC-MS (ESI): m/z (M+1) 196.18.

b) 2-chloro-9-(tetrahydro-2H-pyran-4-yl)pyrido[3,2-e][1,2,4]triazolo[4,3-a]pyrazine: 3-hydrazino-6-chloropyrido[2,3-b]pyrazine (146 mg, 0.75 mmol) and tetrahydropyran-4-carbaldehyde (103 mg, 0.9 mmol) were mixed in methanol (4 mL). After the reaction solution was stirred at room temperature for 1 h, the solvent was removed at reduced pressure, and a crude product 6-chloro-3-(2-((tetrahydro-2H-pyran-4-yl)methylene)hydrazino)pyrido[2,3-b]pyrazine was obtained. This intermediate crude product was dissolved in DCM (4 mL), and (diacetoxyiodo)benzene (483 mg, 1.5 mmol) was added. After the reaction solution was stirred at room temperature for 10 min, the reaction was quenched with a saturated aqueous solution of sodium bicarbonate (10 mL). DCM (10 mL×3) was used for extraction and liquid separation. The organic phase was washed with a saturated saline solution, dried with anhydrous sodium sulfate, filtered, and concentrated at reduced pressure to obtain a crude product. Isolation and purification by column chromatography (silica gel, DCM:MeOH=10:1 as an eluant) was performed to obtain the targeted compound (104 mg, 48% yield, pale yellow solid). LC-MS (ESI): m/z (M+1) 290.17.

c) N,N-dimethyl-3-(4-(9-(tetrahydro-2H-pyran-4-yl)pyrido[3,2-e][1,2,4]triazolo[4,3-a]pyrazin-2-yl)phenoxy)propan-1-amine: 2-chloro-9-(tetrahydro-2H-pyran-4-yl)pyrido[3,2-e][1,2,4]triazolo[4,3-a]pyrazine (28 mg, 0.11 mmol), 3-(N,N-dimethylamino)propoxyphenylboronic acid pinacol ester (46 mg, 0.15 mmol), cesium carbonate (65 mg, 0.20 mmol) and tetra(triphenylphosphine)palladium (12 mg, 0.01 mmol) were added to a mixed solvent of dioxane (1.0 mL) and water (0.2 mL). After the mixture was stirred at 100° C. for 1 h under the protection of nitrogen, the reaction mixture was cooled to rt, suction filtered, and concentrated at reduced pressure to obtain a crude product. Isolation and purification by preparative liquid chromatography (C18 column, 0-100% acetonitrile/water as a mobile phase) were performed to obtain the targeted compound (5 mg, 12% yield, white solid). LC-MS (ESI): m/z (M+1) 433.60. $^1$H NMR (400 MHz, DMSO-d$_6$): δ 9.33 (s, 1H), 8.54 (d, J=8.5 Hz, 1H), 8.32 (d, J=8.5 Hz, 1H), 8.22 (d, J=8.8 Hz, 2H), 7.19 (d, J=8.8 Hz, 2H), 4.53-4.47 (m, 1H), 4.16-4.05 (m, 4H), 3.68 (t, J=10.8 Hz, 2H), 2.46-2.42 (m, 2H), 2.29-2.13 (m, 8H), 2.09-2.01 (m, 2H), 1.95-1.88 (m, 2H).

Example 32

N,N-dimethyl-3-(4-(1-(tetrahydro-2H-pyran-4-yl)imidazo[1,2-a]quinoxalin-8-yl)phenoxy)propan-1-amine a) 7-bromoquinoxaline-2-amine: 7-bromo-2-chloroquinoxaline (1.0 g, 4.13 mmol) and ammonia (7 mL) were added to 1,4-dioxane (7 mL). After reaction under agitation at 70° C. for 5 h, the reaction mixture was cooled to rt. Water (10 mL) was added, and EA (30 mL×2) was used for extraction. The organic phases were combined, washed with a saturated saline solution (50 mL), dried with anhydrous sodium sulfate, filtered, and concentrated at reduced pressure to obtain a crude compound. Isolation and purification by column chromatography (silica gel, PE:EA=3:1 as an eluant) were performed to obtain the targeted compound (500 mg, 54.2% yield, yellow solid). LC-MS (ESI): m/z (M+1) 223.99.

b) 8-bromo-(tetrahydro-2H-pyran-4-yl)imidazo[1,2-a]quinoxaline: 7-bromoquinoxaline-2-amine (500 mg, 2.24 mmol) and 2-bromo-1-(tetrahydro-2H-pyran-4-yl)ethan-1-one (462 mg, 2.24 mmol) were added to N-methylpyrrolidone (1 mL). After reaction under agitation at 150° C. for 1 h under the protection of nitrogen, the reaction mixture was cooled to rt. Water (10 mL) was added, and EA (20 mL×2) was used for extraction. The organic phases were combined, washed with a saturated saline solution (20 mL×2), dried with anhydrous sodium sulfate, filtered, and concentrated at reduced pressure to obtain a crude compound. Isolation and purification by column chromatography (silica gel, DCM:MeOH=30:1 as an eluant) was performed to obtain the targeted compound (120 mg, 16.2% yield, yellow solid). LC-MS (ESI): m/z (M+1) 332.14.

c) N,N-dimethyl-3-(4-(1-(tetrahydro-2H-pyran-4-yl)imidazo[1,2-a]quinoxalin-8-yl)phenoxy)propan-1-amine: This compound was prepared using a synthesis process similar to that described with reference to Example 1 e, the starting materials being 8-bromo-(tetrahydro-2H-pyran-4-yl)imidazo[1,2-a]quinoxaline and 3-(N,N-dimethylamino) propoxyphenylboronic acid pinacol ester. LC-MS (ESI): m/z (M+1) 431.07. $^1$H NMR (400 MHz, CDCl$_3$) δ 9.26 (s, 1H), 8.24-8.17 (m, 2H), 7.92 (dd, J=8.8, 2.1 Hz, 1H), 7.71 (d, J=8.7 Hz, 2H), 7.03 (d, J=8.7 Hz, 2H), 6.53 (s, 1H), 4.15-4.08 (m, 4H), 3.54 (td, J=12.0, 2.1 Hz, 2H), 3.20-3.13 (m, 1H), 2.63 (t, J=6.0 Hz, 2H), 2.38 (s, 6H), 2.12-2.05 (m, 4H), 2.00-1.93 (m, 2H).

The following compounds 33-38 were prepared using a process similar to that in Example 32 and corresponding starting materials.

Example 33

N,N-dimethyl-3-((5-(1-(tetrahydro-2H-pyran-4-yl) imidazo[1,5-c]quinazolin-9-yl)pyridin-2-yl)oxy) propan-1-amine

M.W. 431.54

Example 34

N,N-dimethyl-3-(4-(1-(tetrahydro-2H-pyran-4-yl) imidazo[1,5-c]quinazolin-9-yl)phenoxy)propan-1-amine

M.W. 430.55

Example 35

N,N-dimethyl-3-((5-(1-morpholinoimidazo[1,5-c] quinazolin-9-yl)pyridin-2-yl)oxy)propan-1-amine

M.W. 432.53

Example 36

N,N-dimethyl-3-(4-(1-morpholinoimidazo[1,5-c] quinazolin-9-yl)phenoxy)propan-1-amine

M.W. 431.54

Example 37

N,N-dimethyl-3-(4-(1-(tetrahydro-2H-pyran-4-yl) imidazo[1,5-a]quinoxalin-8-yl)phenoxy)propan-1-amine (M.W. 430.55)

Example 38

N,N-dimethyl-3-(4-(1-(tetrahydro-2H-pyran-4-yl) pyrrolo[1,2-a]quinoxalin-8-yl)phenoxy)propan-1-amine (M.W. 429.56)

The compound of Example 39 was prepared using a synthesis process similar to that described with reference to Example 1 e, the starting materials being 1-(tetrahydro-2H-pyran-4-yl)-8-bromo-[1,2,4]triazolo[4,3-a]quinoxaline and phenylboronic acid.

The compound of Example 40 was prepared by reaction of the compound of Example 10 with sodium hydride and iodomethane in N,N-dimethyl formamide at room temperature.

The compounds of Examples 41-43 were obtained by firstly preparing corresponding tert-butoxycarbonyl-protected intermediates using a synthesis process similar to that described with reference to Example 5 b, followed by deprotection under an acidic condition (e.g. in a solution of hydrochloric acid in dioxane).

The compounds of Examples 44-54 were prepared using a synthesis process similar to that described with reference to Example 5 b, the starting materials being 1-(tetrahydro-2H-pyran-4-yl)-(4,4,5,5-tetramethyl-1,3,2-dioxaborolan-2-yl)[1,2,4]triazolo[4,3-a]quinoxaline and corresponding N,N-dimethyl-1-(4-bromo-substituted phenyl)piperidin-4-amine or N,N-dimethyl-1-(6-bromopyrid-3-yl)piperidin-4-amine or N,N-dimethyl-1-(1-(4-bromophenyl)piperidin-4-yl)alkylamine.

The compounds of Examples 55-63 were prepared using a synthesis process similar to that described with reference to Example 23, the starting materials being 8-bromo-1-((2R,6S)-3,4,5-trimethylpiperazin-1-yl)-[1,2,4]triazolo[4,3-a] quinoxaline and corresponding N,N-dimethyl-3-(4-(4,4,5,5-tetramethyl-1,3,2-dioxaborolan-2-yl)-2-substituted phenoxy)propan-1-amine or N,N-dimethyl-1-(4-(4,4,5,5-tetramethyl-1,3,2-dioxaborolan-2-yl)-substituted phenyl)piperidin-4-amine.

The compound of Example 64 was prepared using a synthesis process similar to that described with reference to Example 3, the starting materials being 2-hydrazino-7-bromoquinoxaline, 4-(dimethylamino)piperid-1-ylcarbonyl chloride and N,N-dimethyl-1-(4-(4,4,5,5-tetramethyl-1,3,2-dioxaborolan-2-yl)phenyl)piperidin-4-amine.

The compound of Example 65 was prepared using a synthesis process similar to that described with reference to Example 31, the starting materials being 2-hydroxy-7-bromoquinoxaline, benzotriazol-1-yl-oxytripyrrolidinophosphonium hexafluorophosphate, hydrazine hydrate, morpholin-2-acetaldehyde and N,N-dimethyl-1-(4-(4,4,5,5-tetramethyl-1,3,2-dioxaborolan-2-yl)phenyl)piperidin-4-amine.

In Example 66, a synthesis process similar to that described with reference to Example 3 e was firstly used to prepare an intermediate tert-butyl methyl(1-(4-(1-(morpholinomethyl)-[1,2,4]triazolo[4,3-a]quinoxalin-8-yl)phenyl)piperidin-4-yl)aminoformate (the starting materials being 4-((8-bromo-[1,2,4]triazolo[4,3-a]quinoxalin-1-yl)methyl)morpholine which is an intermediate in Example 65, and 4-(4-(N-tert-butoxycarbonylmethylamino)piperidyl) phenylboronic acid pinacol ester), and then this intermediate was deprotected under an acidic condition to obtain the targeted compound N-methyl-1-(4-(1-(morpholinomethyl)-[1,2,4]triazolo[4,3-a]quinoxalin-8-yl)phenyl)piperidin-4-amine.

The following compounds can also be prepared by those skilled in the art according to known methods.

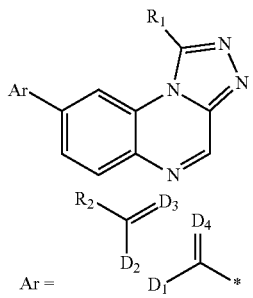

| Example | Ar | R₁ | LC-MS (ESI) | ¹H NMR, 400 MHz |
|---|---|---|---|---|
| 39 | phenyl | tetrahydropyran-4-yl | (M + 1) 331.62 | CDCl₃: δ 9.26 (s, 1H), 8.27-8.22 (m, 2H), 7.91 (dd, J = 8.4, 1.5 Hz, 1H), 7.66 (d, J = 7.3 Hz, 2H), 7.57 (t, J = 7.5 Hz, 2H), 7.50 (t, J = 7.3 Hz, 1H), 4.29-4.20 (m, 2H), 3.89-3.78 (m, 1H), 3.77-3.67 (m, 2H), 2.45-2.25 (m, 4H) |
| 40 | 4-(3-(trimethylammonio)propylamino)phenyl | tetrahydropyran-4-yl | M 445.39 | DMSO-d₆: δ 9.25 (s, 1H), 8.56-8.48 (m, 1H), 8.11 (d, J = 8.4 Hz, 1H), 7.95 (d, J = 7.7 Hz, 1H), 7.65 (d, J = 8.4 Hz, 2H), 6.79 (d, J = 8.3 Hz, 2H), 6.25 (brs, 1H), 4.19-4.12 (, 1H), 4.10-4.02 (m, 2H), 3.69 (t, J = 10.8 Hz, 2H), 3.47-3.42 (m, 2H), 3.23-3.17 (m, 2H), 3.09 (s, 9H), 2.23-2.14 (, 2H), 2.12-1.96 (m, 4H) |
| 41 | 4-(4-aminopiperidin-1-yl)phenyl | tetrahydropyran-4-yl | (M + 1) 429.38 | DMSO-d₆: δ 9.27 (s, 1H), 8.32-8.27 (m, 1H), 8.13 (d, J = 8.5 Hz, 1H), 8.02-7.97 (m, 1H), 7.72 (d, J = 8.8 Hz, 2H), 7.14 (d, J = 8.8 Hz, 2H), 4.21-4.15 (m, 1H), 4.10-4.03 (m, 2H), 3.90-3.83 (m, 2H), 3.70 (t, J = 10.7 Hz, 2H), 3.05-3.01 (m, 1H), 2.91-2.83 (m, 2H), 2.22-2.16 (m, 2H), 2.09-2.01 (m, 2H), 1.92-1.85 (m, 2H), 1.52-1.43 (m, 2H) |
| 42 | 4-(4-(methylamino)piperidin-1-yl)phenyl | tetrahydropyran-4-yl | (M + 1) 443.40 | CDCl₃: δ 9.21 (s, 1H), 8.31 (brs, 1H), 8.22-8.13 (m, 2H), 7.84 (dd, J = 8.5 1.7 Hz, 1H), 7.57 (d, J = 8.8 Hz, 2H), 7.06 (d, J = 8.8 Hz, 2H), 4.28-4.21 (m, 2H), 3.95-3.88 (m, 2H), 3.85-3.80 (m, 1H), 3.73 (t, J = 10.2 Hz, 2H), 3.11-3.06 (m, 1H), 2.90 (t, J = 11.7 Hz, 2H), 2.70 (s, 3H), 2.41-2.28 (m, 6H), 2.03-1.99 (m, 2H) |
| 43 | 4-(4-(ethylamino)piperidin-1-yl)phenyl | tetrahydropyran-4-yl | (M + 1) 457.89 | DMSO-d₆: δ 9.27 (s, 1H), 8.36 (brs, 1H), 8.33-8.26 (m, 1H), 8.13 (d, J = 8.4 Hz, 1H), 8.00 (d, J = 8.3 Hz, 1H), 7.71 (d, J = 8.5 Hz, 2H), 7.13 (d, J = 8.5 Hz, 2H), 4.21-4.14 (m, 1H), 4.11-4.01 (m, 2H), 3.90-3.79 (m, 2H), 3.74-3.65 (m, 2H), 2.91-2.81 (m, 2H), 2.79-2.64 (m, 3H), 2.25-2.14 (m, 2H), 2.11-2.00 (m, 2H), 1.99-1.87 (m, 2H), 1.46-1.32 (m, 2H), 1.07 (t, J = 7.0 Hz, 3H) |
| 44 | 4-(4-(dimethylamino)piperidin-1-yl)-2-fluorophenyl | tetrahydropyran-4-yl | (M + 1) 475.31 | DMSO-d₆: δ 9.31 (s, 1H), 8.31 (s, 1H), 8.16 (d, J = 8.4 Hz, 1H), 8.04 (d, J = 8.4 Hz, 1H), 7.67 (d, J = 14.5 Hz, 1H), 7.60 (d, J = 8.3 Hz, 1H), 7.23 (t, J = 8.9 Hz, 1H), 4.31-4.16 (m, 1H), 4.05 (d, J = 11.4 Hz, 2H), 3.71 (t, J = 10.6 Hz, 2H), 3.52 (d, J = 11.8 Hz, 2H), 2.76 (t, J = 11.5 Hz, 2H), 2.23 (s, 6H), 2.30-2.13 (m, , 2H), 2.16-1.96 (m, 2H), 1.88 (d, J = 11.7 Hz, 2H), 1.66-1.40 (m, 2H), 1.33-1.11 (m, 1H) |

-continued

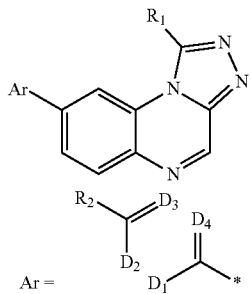

| Example | Ar | R₁ | LC-MS (ESI) | ¹H NMR, 400 MHz |
|---|---|---|---|---|
| 45 | (2-Cl-4-(4-dimethylamino-piperidin-1-yl)phenyl) | tetrahydropyran-4-yl | (M + 1) 491.13 | DMSO-d₆: δ 9.32 (s, 1H), 8.33 (s, 1H), 8.17 (d, J = 8.0 Hz, 1H), 8.05 (dd, J = 8.5, 1.6 Hz, 1H), 7.88 (d, J = 2.2 Hz, 1H), 7.78 (dd, J = 8.4, 2.2 Hz, 1H), 7.34 (d, J = 8.4 Hz, 1H), 4.30-4.18 (m, 1H), 4.13-4.01 (m, 2H), 3.71 (dd, J = 11.3, 9.7 Hz, 2H), 3.44 (d, J = 12.0 Hz, 2H), 2.73 (t, J = 11.1 Hz, 2H), 2.45-2.36 (m, 1H), 2.31 (s, 6H), 2.24-2.13 (m, 2H), 2.13-1.97 (m, 2H), 1.97-1.86 (m, 2H), 1.71-1.48 (m, 2H) |
| 46 | (2-methyl-4-(4-dimethylamino-piperidin-1-yl)phenyl) | tetrahydropyran-4-yl | (M + 1) 471.16 | DMSO-d₆: δ 9.30 (s, 1H), 8.32 (s, 1H), 8.15 (d, J = 8.4 Hz, 1H), 8.01 (d, J = 8.4 Hz, 1H), 7.63 (s, 2H), 7.19 (d, J = 9.0 Hz, 1H), 4.28-4.13 (m, 1H), 4.07 (d, J = 11.1 Hz, 2H), 3.71 (t, J = 10.6 Hz, 2H), 3.20 (d, J = 11.9 Hz, 2H), 2.67 (t, J = 11.1 Hz, 2H), 2.37-2.29 (m, 10H), 2.25-2.12 (m, 2H), 2.13-1.99 (m, 2H), 1.95-1.84 (m, 2H), 1.70-1.52 (m, 2H) |
| 47 | (2-CF₃-4-(4-dimethylamino-piperidin-1-yl)phenyl) | tetrahydropyran-4-yl | (M + 1) 525.33 | DMSO-d₆: δ 9.35 (s, 1H), 8.39 (d, J = 1.4 Hz, 1H), 8.21 (d, J = 8.4 Hz, 1H), 8.13-8.09 (m, 2H), 8.02 (d, J = 2.1 Hz, 1H), 7.70 (d, J = 8.5 Hz, 1H), 4.32-4.17 (m, 1H), 4.12-3.97 (m, 2H), 3.69 (td, J = 11.4, 9.8 Hz, 2H), 3.14-3.11 (m, 2H), 2.85 (t, J = 10.9 Hz, 2H), 2.48-2.36 (m, 1H), 2.32 (s, 6H), 2.27-2.14 (m, 2H), 2.15-1.97 (m, 2H), 1.98-1.82 (m, 2H), 1.69-1.45 (m, 2H) |
| 48 | (3-F-4-(4-dimethylamino-piperidin-1-yl)phenyl) | tetrahydropyran-4-yl | (M + 1) 475.36 | DMSO-d₆: δ 9.33 (s, 1H), 8.29 (d, J = 1.6 Hz, 1H), 8.17 (d, J = 8.4 Hz, 1H), 7.78 (dd, J = 8.4, 1.6 Hz, 1H), 7.41 (d, J = 8.7 Hz, 1H), 7.15 (d, J = 2.5 Hz, 1H), 7.08 (dd, J = 8.8, 2.5 Hz, 1H), 4.04-4.00 (m, 2H), 3.92-3.85 (m, 2H), 3.65-3.58 (m, 2H), 2.82 (t, J = 11.3 Hz, 2H), 2.40-2.33 (m, 1H), 2.25 (s, 6H), 2.19-2.13 (m, 2H), 2.07-1.96 (m, 3H), 1.90-1.84 (m, 2H), 1.51-1.43 (m, 2H) |
| 49 | (3-Cl-4-(4-dimethylamino-piperidin-1-yl)phenyl) | tetrahydropyran-4-yl | (M + 1) 491.28 | DMSO-d₆: δ 9.33 (s, 1H), 8.29 (d, J = 1.6 Hz, 1H), 8.17 (d, J = 8.3 Hz, 1H), 7.78 (dd, J = 8.4, 1.7 Hz, 1H), 7.41 (d, J = 8.7 Hz, 1H), 7.15 (d, J = 2.5 Hz, 1H), 7.09 (dd, J = 8.8, 2.5 Hz, 1H), 4.04-4.00 (m, 2H), 3.92-3.86 (m, 2H), 3.65-3.58 (m, 2H), 2.82 (t, J = 11.3 Hz, 2H), 2.40-2.33 (m, 1H), 2.26 (s, 6H), 2.19-2.13 (m, 2H), 2.07-1.97 (m, 3H), 1.89-1.84 (m, 2H), 1.51-1.44 (m, 2H) |

-continued

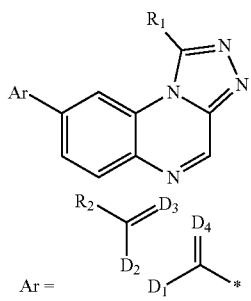

| Example | Ar | R₁ | LC-MS (ESI) | ¹H NMR, 400 MHz |
|---|---|---|---|---|
| 50 | (4-dimethylamino-piperidinyl)-3-methylphenyl | tetrahydropyran-4-yl | (M + 1) 471.32 | DMSO-$d_6$: δ 9.31 (s, 1H), 8.13 (d, J = 8.3 Hz, 1H), 8.09 (d, J = 1.5 Hz, 1H), 7.71 (dd, J = 8.4, 1.6 Hz, 1H), 7.23 (d, J = 8.3 Hz, 1H), 6.96-6.90 (m, 2H), 4.04-3.98 (m, 2H), 3.88-3.81 (m, 2H), 3.64-3.56 (m, 2H), 2.74 (t, J = 11.3 Hz, 2H), 2.38-2.31 (m, 4H), 2.25 (s, 6H), 2.17-2.11 (m, 2H), 2.08-1.95 (m, 3H), 1.90-1.84 (m, 2H), 1.54-1.43 (m, 2H) |
| 51 | (4-dimethylamino-piperidinyl)-3-trifluoromethylphenyl | tetrahydropyran-4-yl | (M + 1) 525.16 | DMSO-$d_6$: δ 9.30 (s, 1H), 8.38 (s, 1H), 8.15 (d, J = 8.5 Hz, 1H), 7.89 (d, J = 8.6 Hz, 1H), 7.58 (t, J = 9.3 Hz, 1H), 6.98-6.90 (m, 2H), 4.07-4.03 (m, 2H), 3.94-3.87 (m, 2H), 3.65 (t, J = 10.6 Hz, 2H), 2.83 (t, J = 11.3 Hz, 2H), 2.34-2.28 (m, 1H), 2.24-2.12 (m, 8H), 2.10-1.92 (m, 3H), 1.88-1.81 (m, 2H), 1.49-1.40 (m, 2H) |
| 52 | (4-dimethylamino-piperidinyl)pyridin-2-yl | tetrahydropyran-4-yl | (M + 1) 458.09 | DMSO-$d_6$: δ 9.29 (s, 1H), 8.96 (s, 1H), 8.52 (s, 1H), 8.35-8.30 (m, 1H), 8.13 (d, J = 8.4 Hz, 1H), 8.01 (d, J = 8.8 Hz, 1H), 7.48 (dd, J = 8.8, 2.6 Hz, 1H), 4.15-4.01 (m, 3H), 3.99-3.89 (m, 2H), 3.74 (t, J = 11.0 Hz, 2H), 2.85 (t, J = 11.6 Hz, 2H), 2.35-2.16 (m, 8H), 2.11-1.95 (m, 3H), 1.91-1.80 (m, 2H), 1.54-1.44 (m, 2H) |
| 53 | 4-[4-((dimethylamino)methyl)piperidin-1-yl]phenyl | tetrahydropyran-4-yl | (M + 1) 471.10 | CDCl₃: δ 9.19 (s, 1H), 8.20 (d, J = 1.6 Hz, 1H), 8.15 (d, J = 8.5 Hz, 1H), 7.86 (dd, J = 8.5, 1.7 Hz, 1H), 7.56 (d, J = 8.7 Hz, 2H), 6.69 (d, J = 8.8 Hz, 2H), 4.27-4.23 (m, 2H), 3.87-3.82 (m, 1H), 3.77-3.71 (m, 2H), 3.61-3.57 (m, 1H), 3.52-3.48 (m, 1H), 3.42-3.38 (m, 1H), 3.06 (t, J = 8.8 Hz, 1H), 2.87-2.81 (m, 2H), 2.64 (s, 6H), 2.41-2.29 (m, 6H), 1.98-1.94 (m, 2H), 1.79-1.75 (m, 1H) |
| 54 | 4-[4-(2-(dimethylamino)ethyl)piperidin-1-yl]phenyl | tetrahydropyran-4-yl | (M + 1) 485.17 | CDCl₃: δ 9.21 (s, 1H), 8.21 (d, J = 1.7 Hz, 1H), 8.17 (d, J = 8.5 Hz, 1H), 7.87 (dd, J = 8.5, 1.8 Hz, 1H), 7.57 (d, J = 8.8 Hz, 2H), 7.07 (d, J = 8.9 Hz, 2H), 4.27-4.23 (m, 2H), 3.86-3.81 (m, 3H), 3.76-3.71 (m, 2H), 2.88-2.81 (m, 2H), 2.58-2.52 (m, 2H), 2.41 (s, 6H), 2.38-2.33 (m, 2H), 2.32-2.28 (m, 2H), 1.85 (m, 2H), 1.62-1.57 (m, 4H), 1.43-1.41 (m, 1H) |

-continued

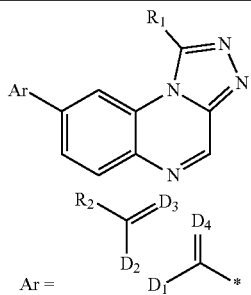

| Example | Ar | R₁ | LC-MS (ESI) | ¹H NMR, 400 MHz |
|---|---|---|---|---|
| 55 | 4-(3-(dimethylamino)propoxy)-3-fluorophenyl | (2S,5R)-2,5-dimethyl-4-methylpiperazinyl | (M + 1) 492.31 | DMSO-$d_6$: δ 9.19 (s, 1H), 8.77-8.67 (m, 1H), 8.09 (d, J = 8.4 Hz, 1H), 7.98 (dd, J = 8.4, 1.8 Hz, 1H), 7.64 (d, J = 12.7 Hz, 1H), 7.57 (d, J = 8.3 Hz, 1H), 7.40-7.35 (m, 1H), 4.18 (t, J = 6.4 Hz, 2H), 3.46-3.40 (m, 2H), 3.36-3.33 (m, 2H), 2.92-2.79 (m, 2H), 2.41 (t, J = 7.0 Hz, 2H), 2.28 (s, 3H), 2.18 (s, 6H), 1.95-1.88 (m, 2H), 1.17-1.02 (m, 6H) |
| 56 | 4-(3-(dimethylamino)propoxy)-3-chlorophenyl | (2S,5R)-2,5-dimethyl-4-methylpiperazinyl | M.W. 508.07 | — |
| 57 | 4-(3-(dimethylamino)propoxy)-3-(trifluoromethyl)phenyl | (2S,5R)-2,5-dimethyl-4-methylpiperazinyl | (M + 1) 542.33 | DMSO-$d_6$: δ 9.20 (s, 1H), 8.76 (s, 1H), 8.12 (d, J = 8.4 Hz, 1H), 8.08-7.99 (m, 2H), 7.96 (d, J = 1.9 Hz, 1H), 7.46 (d, J = 8.8 Hz, 1H), 4.24 (t, J = 6.1 Hz, 2H), 3.48-3.35 (m, 4H), 2.85 (t, J = 10.1 Hz, 2H), 2.41 (t, J = 7.0 Hz, 2H), 2.26 (s, 3H), 2.17 (s, 6H), 1.94-1.88 (m, 2H), 1.08 (d, J = 5.5 Hz, 6H) |
| 58 | 4-(4-(dimethylamino)piperidin-1-yl)phenyl | (2S,5R)-2,5-dimethyl-4-methylpiperazinyl | (M + 1) 499.37 | DMSO-$d_6$: δ 9.14 (s, 1H), 8.74 (s, 1H), 8.06 (d, J = 8.4 Hz, 1H), 7.93 (dd, J = 8.5, 1.9 Hz, 1H), 7.66 (d, J = 8.8 Hz, 2H), 7.12 (d, J = 8.9 Hz, 2H), 3.93-3.84 (m, 2H), 3.46-3.40 (m, 2H), 2.92-2.73 (m, 4H), 2.43-2.38 (m, 1H), 2.35-2.20 (m, 9H), 2.04-1.94 (m, 6.9 Hz, 2H), 1.92-1.85 (m, 2H), 1.55-1.47 (m, 2H), 1.10 (s, 6H) |
| 59 | 4-(4-(dimethylamino)piperidin-1-yl)-3-fluorophenyl | (2S,5R)-2,5-dimethyl-4-methylpiperazinyl | (M + 1) 517.33 | DMSO-$d_6$: δ 9.18 (s, 1H), 8.78-8.67 (m, 1H), 8.08 (d, J = 8.4 Hz, 1H), 7.97 (dd, J = 8.5, 1.7 Hz, 1H), 7.59-7.50 (m, 2H), 7.23-7.18 (m, 1H), 3.54-3.48 (m, 2H), 3.45-3.39 (m, 2H), 2.94-2.81 (m, 2H), 2.76 (t, J = 11.2 Hz, 2H), 2.57-2.52 (m, 1H), 2.33-2.17 (m, 10H), 2.02-1.96 (m, 1H), 1.91-1.84 (m, 2H), 1.61-1.51 (m, 2H), 1.16-1.01 (m, 6H) |
| 60 | 4-(4-(dimethylamino)piperidin-1-yl)-3-chlorophenyl | (2S,5R)-2,5-dimethyl-4-methylpiperazinyl | (M + 1) 533.30 | DMSO-$d_6$: δ 9.19 (s, 1H), 8.76-8.66 (m, 1H), 8.09 (d, J = 8.3 Hz, 1H), 7.97 (d, J = 8.6 Hz, 1H), 7.79 (s, 1H), 7.72 (d, J = 8.4 Hz, 1H), 7.31 (d, J = 8.4 Hz, 1H), 3.45-3.41 (m, 4H), 2.92-2.81 (m, 2H), 2.76-2.69 (m, 2H), 2.58-2.52 (m, 2H), 2.34-2.26 (m, 4H), 2.24 (s, 6H), 1.93-1.86 (m, 2H), 1.64-1.54 (n, 2H), 1.18-1.04 (m, 6H) |

-continued

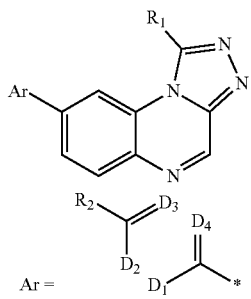

| Example | Ar | R₁ | LC-MS (ESI) | ¹H NMR, 400 MHz |
|---|---|---|---|---|
| 61 | (dimethylamino-piperidinyl-phenyl with CF₃) | (dimethyl piperazine) | (M + 1) 567.31 | DMSO-d₆: δ 9.22 (s, 1H), 8.82-8.73 (m, 1H), 8.14 (d, J = 8.5 Hz, 1H), 8.06-8.02 (m, 2H), 8.00-7.98 (m, 1H), 7.67 (d, J = 8.3 Hz, 1H), 3.44-3.39 (m, 2H), 3.15-3.10 (m, 2H), 2.87-2.80 (m, 4H), 2.33-2.25 (m, 12H), 1.91-1.87 (m, 2H), 1.60-1.54 (m, 2H), 1.08 (d, J = 5.3 Hz, 6H) |
| 62 | (dimethylamino-piperidinyl-phenyl with F and CF₃) | (dimethyl piperazine) | M.W. 584.67 | — |
| 63 | (dimethylamino-piperidinyl-phenyl with Cl and CF₃) | (dimethyl piperazine) | M.W. 601.12 | — |
| 64 | (dimethylamino-piperidinyl-phenyl) | (dimethylamino-piperidinyl) | (M + 1) 499.43 | DMSO-d₆: δ 9.16 (s, 1H), 8.66 (s, 1H), 8.07 (d, J = 8.5 Hz, 1H), 7.94 (d, J = 7.5 Hz, 1H), 7.70 (d, J = 8.8 Hz, 2H), 7.14 (d, J = 8.8 Hz, 2H), 4.04-3.91 (m, 2H), 3.70-3.58 (m, 2H), 3.30 (s, 6H), 3.12-2.88 (m, 4H), 2.81 (t, J = 11.8 Hz, 2H), 2.56 (s, 6H), 2.23-2.10 (m, 2H), 2.07-1.95 (m, 2H), 1.93-1.74 (m, 2H), 1.72-1.53 (m, 2H) |
| 65 | (dimethylamino-piperidinyl-phenyl) | (morpholinoethyl) | (M + 1) 472.40 | DMSO-d₆: δ 9.29 (s, 1H), 8.89 (d, J = 1.6 Hz, 1H), 8.11 (d, J = 8.5 Hz, 1H), 8.01 (dd, J = 8.5, 1.7 Hz, 1H), 7.74 (d, J = 8.8 Hz, 2H), 7.10 (d, J = 8.8 Hz, 2H), 4.37 (s, 2H), 3.89-3.82 (m, 2H), 3.61-3.53 (m, 4H), 2.78 (t, J = 11.3 Hz, 2H), 2.61-2.55 (m, 4H), 2.30-2.25 (m, 1H), 2.19 (s, 6H), 1.89-1.82 (m, 2H), 1.52-1.43 (m, 2H) |

-continued

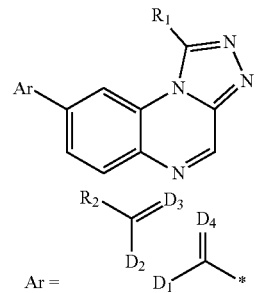

| Example | Ar | R₁ | LC-MS (ESI) | ¹H NMR, 400 MHz |
|---|---|---|---|---|
| 66 | (piperidinyl-phenyl with N-methyl) | (morpholinylmethyl) | (M + 1) 458.41 | DMSO-d₆: δ 9.30 (s, 1H), 8.90 (s, 1H), 8.12 (d, J = 8.4 Hz, 1H), 8.01 (dd, J = 8.5, 1.6 Hz, 1H), 7.76 (d, J = 8.7 Hz, 2H), 7.12 (d, J = 8.8 Hz, 2H), 4.37 (s, 2H), 3.96-3.85 (m, 2H), 3.65-3.51 (m, 4H), 3.03-2.96 (m, 1H), 2.84 (t, J = 11.6 Hz, 2H), 2.64-2.54 (m, 4H), 2.51 (s, 3H), 2.06-1.99 (m, 2H), 1.58-1.48 (m, 2H) |

The compounds of Examples 67-69 and 71 were prepared using a synthesis process similar to that described with reference to Example 31, the starting materials being 7-chloropyrido[3,4-b]pyrazin-2(1H)-one, benzotriazol-1-yl-oxytripyrrolidinophosphonium hexafluorophosphate, hydrazine hydrate, tetrahydropyran-4-carbaldehyde and corresponding pinacol phenylboronates.

In Example 70, a synthesis process similar to that described with reference to Example 3 e was firstly used to prepare an intermediate tert-butyl methyl(1-(4-(1-(tetrahydropyran-4-yl)pyrido[3,4-e][1,2,4]triazolo[4,3-a]pyrazin-8-yl)phenyl)piperidin-4-yl)aminoformate (the starting materials being 8-chloro-1-(tetrahydropyran-4-yl)pyrido[3,4-e][1,2,4]triazolo[4,3-a]pyrazine which is an intermediate in Examples 67-69, and 4-(4-(N-tert-butoxycarbonylmethyl-amino)piperidyl)phenylboronic acid pinacol ester), and then this intermediate was deprotected under an acidic condition to obtain the targeted compound N-methyl-1-(4-(1-(tetrahydropyran-4-yl)pyrido[3,4-e][1,2,4]triazolo[4,3-a]pyrazin-8-yl)phenyl)piperidin-4-amine.

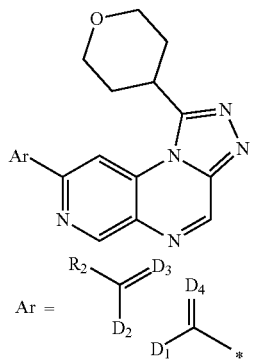

| Example | Ar | LC-MS (ESI) | ¹H NMR, 400 MHz |
|---|---|---|---|
| 67 | (phenyl) | (M + 1) 332.03 | DMSO-d₆: δ 9.41 (d, J = 5.4 Hz, 2H), 8.43 (s, 1H), 8.23-8.20 (m, 2H), 7.64-7.60 (m, 2H), 7.58-7.53 (m, 1H), 4.33-4.26 (m, 1H), 4.07-4.02 (m, 2H), 3.81-3.74 (m, 2H), 2.22-2.16 (m, 2H), 2.07-2.00 (m, 2H) |
| 68 | (4-(dimethylaminomethyl)phenyl) | (M + 1) 389.09 | DMSO-d₆: δ 9.41 (s, 1H), 9.39 (s, 1H), 8.43 (s, 1H), 8.18 (d, J = 8.3 Hz, 2H), 7.54 (d, J = 8.2 Hz, 2H), 4.32-4.25 (m, 1H), 4.07-4.01 (m, 2H), 3.82-3.73 (m, 2H), 3.54 (s, 2H), 2.26-2.14 (m, 8H), 2.09-1.99 (m, 2H) |

-continued

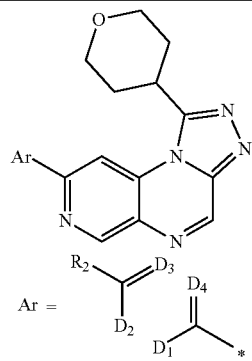

| Example | Ar | LC-MS (ESI) | ¹H NMR, 400 MHz |
|---|---|---|---|
| 69 | | (M + 1) 433.07 | DMSO-$d_6$: δ 9.36 (s, 1H), 9.34 (s, 1H), 8.33 (s, 1H), 8.16 (d, J = 8.4 Hz, 2H), 7.14 (d, J = 8.4 Hz, 2H), 4.32-4.23 (m, 1H), 4.18-4.08 (m, 2H), 4.08-3.97 (m, 2H), 3.77 (t, J = 10.6 Hz, 2H), 2.38 (t, J = 6.8 Hz, 2H), 2.23-2.13 (m, 7H), 2.11-1.95 (m, 3H), 1.94-1.84 (m, 2H) |
| 70 | | (M + 1) 444.10 | DMSO-$d_6$: δ 9.33 (s, 1H), 9.30 (s, 1H), 8.28 (s, 1H), 8.09 (d, J = 8.6 Hz, 2H), 7.15 (d, J = 8.8 Hz, 2H), 4.29-4.21 (m, 1H), 4.11-3.96 (m, 4H), 3.76 (t, J = 10.6 Hz, 2H), 3.19-3.12 (m, 1H), 2.88 (t, J = 12.3 Hz, 2H), 2.56-2.53 (m, 4H), 2.22-2.14 (m, 2H), 2.12-2.00 (m, 4H), 1.64-1.53 (m, 2H). |
| 71 | | (M + 1) 458.11 | DMSO-$d_6$: δ 9.33 (s, 1H), 9.30 (s, 1H), 8.28 (s, 1H), 8.10 (d, J = 8.9 Hz, 2H), 7.16 (d, J = 8.9 Hz, 2H), 4.29-4.23 (m, 1H), 4.08-4.01 (m, 4H), 3.76 (t, J = 10.4 Hz, 2H), 2.84 (t, J = 11.7 Hz, 2H), 2.60 (s, 6H), 2.20-2.14 (m, 2H), 2.09-1.95 (m, 5H), 1.67-1.58 (m, 2H). |

The compounds of Examples 72, 76, 78-79 and 90-93 were prepared using a synthesis process similar to that described with reference to Example 31, the starting materials being 6-chloropyrido[2,3-b]pyrazin-3(4H)-one, benzotriazol-1-yl-oxytripyrrolidinophosphonium hexafluorophosphate, hydrazine hydrate, tetrahydropyran-4-carbaldehyde or morpholin-2-acetaldehyde or 4-(dimethylamino)piperidin-1-carbonyl chloride and corresponding pinacol boronates.

The compounds of Examples 73-75 and 77 were obtained by firstly preparing corresponding tert-butoxycarbonyl protected intermediates using a synthesis process similar to that described with reference to Example 31 c, followed by deprotection under an acidic condition (e.g. in a solution of hydrochloric acid in dioxane).

The compounds of Examples 80-89 were prepared using a synthesis process similar to that described with reference to Example 23 b-e, the starting materials being 6-chloro-3-hydrazinopyrido[2,3-b]pyrazine, tert-butyl (2R,6S)-4-(chloroformyl)-2,6-dimethylpiperazinyl-1-carbonate, formalin and corresponding pinacol phenylboronates.

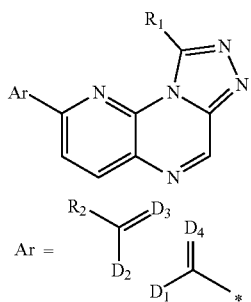

| Example | Ar | R₁ | LC-MS (ESI) | ¹H NMR, 400 MHz |
|---|---|---|---|---|
| 72 | 4-[4-(dimethylamino)piperidin-1-yl]phenyl | tetrahydropyran-4-yl | (M + 1) 458.34 | DMSO-d₆: δ 9.28 (s, 1H), 8.47 (d, J = 8.5 Hz, 1H), 8.26 (d, J = 8.8 Hz, 1H), 8.12 (d, J = 9.0 Hz, 2H), 7.15 (d, J = 9.1 Hz, 2H), 4.54-4.48 (m, 1H), 4.12-4.06 (m, 2H), 4.00-3.94 (m, 2H), 3.72-3.66 (m, 2H), 2.89-2.82 (m, 2H), 2.35-2.31 (m, 1H), 2.29-2.14 (m, 8H), 2.09-2.01 (m, 2H), 1.89-1.83 (m, 2H), 1.51-1.43 (m, 2H) |
| 73 | 4-(4-aminopiperidin-1-yl)phenyl | tetrahydropyran-4-yl | (M + 1) 430.18 | DMSO-d₆: δ 9.29 (s, 1H), 8.47 (d, J = 8.5 Hz, 1H), 8.26 (d, J = 8.6 Hz, 1H), 8.13 (d, J = 9.0 Hz, 2H), 7.16 (d, J = 9.1 Hz, 2H), 4.54-4.49 (m, 1H), 4.12-4.06 (m, 2H), 3.99-3.92 (m, 2H), 3.69 (t, J = 10.7 Hz, 2H), 3.08-3.04 (m, 1H), 2.96-2.90 (m, 2H), 2.25-2.20 (m, 2H), 2.09-2.01 (m, 2H), 1.92-1.86 (m, 2H), 1.49-1.42 (m, 2H) |
| 74 | 4-[4-(methylamino)piperidin-1-yl]phenyl | tetrahydropyran-4-yl | (M + 1) 444.60 | DMSO-d₆: δ 9.27 (s, 1H), 8.45 (d, J = 8.5 Hz, 1H), 8.24 (d, J = 8.6 Hz, 1H), 8.11 (d, J = 8.9 Hz, 2H), 7.13 (d, J = 9.0 Hz, 2H), 4.54-4.46 (m, 1H), 4.12-4.05 (m, 2H), 3.90-3.82 (m, 2H), 3.68 (t, J = 10.9 Hz, 2H), 3.52-3.40 (m, 2H), 2.93 (t, J = 10.8 Hz, 2H), 2.31 (s, 3H), 2.25-2.19 (m, 2H), 2.07-2.00 (m, 2H), 1.92-1.86 (m, 2H), 1.35-1.29 (m, 2H) |
| 75 | 4-[4-(ethylamino)piperidin-1-yl]phenyl | tetrahydropyran-4-yl | (M + 1) 458.38 | DMSO-d₆: δ 9.28 (s, 1H), 8.46 (d, J = 8.5 Hz, 1H), 8.25 (d, J = 8.6 Hz, 1H), 8.12 (d, J = 8.9 Hz, 2H), 7.15 (d, J = 9.0 Hz, 2H), 4.54-4.46 (m, 1H), 4.13-4.05 (m, 2H), 3.99-3.91 (m, 2H), 3.71-3.65 (m, 2H), 2.96-2.86 (m, 3H), 2.81-2.73 (m, 2H), 2.26-2.18 (m, 2H), 2.09-1.93 (m, 4H), 1.50-1.39 (m, 2H), 1.10 (t, J = 7.1 Hz, 3H) |
| 76 | 6-[4-(dimethylamino)piperidin-1-yl]pyridin-3-yl | tetrahydropyran-4-yl | (M + 1) 459.17 | CDCl₃: δ 9.22 (s, 1H), 8.96 (d, J = 2.3 Hz, 1H), 8.43 (d, J = 8.5 Hz, 1H), 8.23 (dd, J = 9.0, 2.5 Hz, 1H), 7.97 (d, J = 8.5 Hz, 1H), 6.82 (d, J = 9.1 Hz, 1H), 4.68-4.62 (m, 2H), 4.55-4.51 (m, 1H), 4.25-4.21 (m, 2H), 3.80-3.75 (m, 2H), 3.04-2.98 (m, 2H), 2.59 (s, 6H), 2.38-2.27 (m, 5H), 2.25-2.18 (m, 2H), 1.76-1.70 (m, 2H) |

-continued

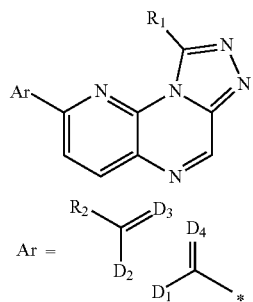

| Example | Ar | R₁ | LC-MS (ESI) | ¹H NMR, 400 MHz |
|---|---|---|---|---|
| 77 | (4-(methylamino)piperidin-1-yl)phenyl | 2-morpholinoethyl | (M + 1) 459.70 | DMSO-d₆: δ 9.31 (s, 1H), 8.47 (d, J = 8.6 Hz, 1H), 8.24 (d, J = 8.6 Hz, 1H), 8.13 (d, J = 8.6 Hz, 2H), 7.10 (d, J = 8.7 Hz, 2H), 4.73 (s, 2H), 3.89-3.81 (m, 2H), 3.60-3.53 (m, 4H), 2.92 (t, J = 11.4 Hz, 2H), 2.77-2.60 (m, 5H), 2.31 (s, 3H), 2.03-1.88 (m, 4H) |
| 78 | (4-(dimethylamino)piperidin-1-yl)phenyl | 2-morpholinoethyl | (M + 1) 473.41 | DMSO-d₆: δ 9.31 (s, 1H), 8.48 (d, J = 8.5 Hz, 1H), 8.25 (d, J = 8.6 Hz, 1H), 8.14 (d, J = 9.0 Hz, 2H), 7.11 (d, J = 9.1 Hz, 2H), 4.73 (s, 2H), 3.98-3.92 (m, 2H), 3.60-3.54 (m, 4H), 2.88-2.81 (m, 2H), 2.70-2.65 (m, 4H), 2.32-2.27 (m, 1H), 2.20 (s, 6H), 1.88-1.82 (m, 2H), 1.50-1.41 (m, 2H) |
| 79 | 4-(3-(dimethylamino)propoxy)phenyl | 2-morpholinoethyl | (M + 1) 448.33 | DMSO-d₆: δ 9.38 (s, 1H), 8.57 (d, J = 8.5 Hz, 1H), 8.33 (d, J = 8.5 Hz, 1H), 8.26 (d, J = 8.9 Hz, 2H), 7.16 (d, J = 8.9 Hz, 2H), 4.71 (s, 2H), 4.17 (t, J = 6.0 Hz, 2H), 3.56 (t, J = 4.4 Hz, 4H), 3.18-3.12 (m, 2H), 2.76 (s, 6H), 2.69-2.64 (m, 4H), 2.16-2.09 (m, 2H) |
| 80 | 4-(3-(dimethylamino)propoxy)phenyl | (3R,5S)-3,4,5-trimethylpiperazin-1-yl methyl | (M + 1) 475.28 | CDCl₃: δ 9.09 (s, 1H), 8.41 (d, J = 8.4 Hz, 1H), 8.05 (d, J = 8.8 Hz, 2H), 7.98 (d, J = 8.5 Hz, 1H), 7.12 (d, J = 8.8 Hz, 2H), 4.22 (t, J = 5.7 Hz, 2H), 4.19-4.13 (m, 2H), 3.83-3.73 (m, 2H), 3.60-3.52 (m, 2H), 3.28-3.23 (m, 2H), 2.85 (s, 6H), 2.73 (s, 3H), 2.42-2.36 (m, 2H), 1.41 (d, J = 6.3 Hz, 6H) |
| 81 | 4-(3-(dimethylamino)propoxy)-3-fluorophenyl | (3R,5S)-3,4,5-trimethylpiperazin-1-yl methyl | (M + 1) 493.34 | CDCl₃: δ 9.08 (s, 1H), 8.39 (d, J = 8.4 Hz, 1H), 8.00-7.91 (m, 2H), 7.85-7.80 (m, 1H), 7.16-7.10 (m, 1H), 4.25 (t, J = 6.1 Hz, 2H), 4.08-4.00 (m, 2H), 3.30-3.15 (m, 2H), 2.98-2.80 (m, 4H), 2.61 (s, 6H), 2.45 (s, 3H), 2.30-2.24 (m, 2H), 1.19 (d, J = 6.1 Hz, 6H) |

-continued

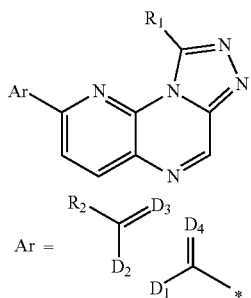

| Example | Ar | R₁ | LC-MS (ESI) | ¹H NMR, 400 MHz |
|---|---|---|---|---|
| 82 | [dimethylaminopropoxy-2-chlorophenyl] | [2,5-dimethylpiperazinyl] | (M + 1) 509.25 | CDCl₃: δ 9.08 (s, 1H), 8.39 (d, J = 8.4 Hz, 1H), 8.28 (d, J = 2.0 Hz, 1H), 7.97-7.93 (m, 2H), 7.10 (d, J = 8.6 Hz, 1H), 4.26 (t, J = 6.0 Hz, 2H), 4.07-4.03 (m, 2H), 3.27-3.20 (m, 2H), 3.08-3.03 (m, 2H), 2.97-2.90 (m, 2H), 2.68 (s, 6H), 2.49 (s, 3H), 2.33-2.29 (m, 2H), 1.20 (d, J = 6.1 Hz, 6H) |
| 83 | [dimethylaminopropoxy-2-trifluoromethylphenyl] | [2,5-dimethylpiperazinyl] | (M + 1) 543.30 | CDCl₃: δ 9.09 (s, 1H), 8.45-8.41 (m, 2H), 8.24-8.19 (m, 1H), 7.96 (d, J = 8.4 Hz, 1H), 7.19 (d, J = 8.7 Hz, 1H), 4.29 (t, J = 5.8 Hz, 2H), 4.06-3.99 (m, 2H), 3.28-3.20 (m, 2H), 3.04-2.98 (m, 2H), 2.91-2.83 (m, 2H), 2.66 (s, 6H), 2.45 (s, 3H), 2.31-2.28 (m, 2H), 1.16 (d, J = 6.3 Hz, 6H) |
| 84 | [4-(dimethylamino)piperidin-1-yl-phenyl] | [2,5-dimethylpiperazinyl] | (M + 1) 500.31 | CDCl₃: δ 9.05 (s, 1H), 8.35 (d, J = 8.4 Hz, 1H), 8.06 (d, J = 8.8 Hz, 2H), 7.95 (d, J = 8.5 Hz, 1H), 7.08 (d, J = 8.8 Hz, 2H), 4.15-4.02 (m, 4H), 3.62-3.33 (m, 4H), 3.19-3.13 (m, 1H), 2.97-2.90 (m, 2H), 2.72 (s, 6H), 2.60 (s, 3H), 2.23-2.17 (m, 2H), 1.90-1.84 (m, 2H), 1.35-1.26 (m, 6H) |
| 85 | [4-(dimethylamino)piperidin-1-yl-2-fluorophenyl] | [2,5-dimethylpiperazinyl] | (M + 1) 518.35 | CDCl₃: δ 9.07 (s, 1H), 8.38 (d, J = 8.4 Hz, 1H), 7.94 (d, J = 8.4 Hz, 1H), 7.92-7.86 (m, 1H), 7.81 (dd, J = 8.4, 1.8 Hz, 1H), 7.09-7.03 (m, 1H), 4.10-4.01 (m, 2H), 3.78-3.71 (m, 2H), 3.32-3.14 (m, 2H), 3.04-2.96 (m, 1H), 2.95-2.78 (m, 4H), 2.67 (s, 6H), 2.46 (s, 3H), 2.29-2.21 (m, 2H), 1.99-1.92 (m, 2H), 1.25-1.20 (m, 6H) |
| 86 | [4-(dimethylamino)piperidin-1-yl-2-chlorophenyl] | [2,5-dimethylpiperazinyl] | (M + 1) 534.30 | CDCl₃: δ 9.08 (s, 1H), 8.40 (d, J = 8.4 Hz, 1H), 8.25 (d, J = 2.0 Hz, 1H), 7.96 (d, J = 8.4 Hz, 1H), 7.93 (dd, J = 8.4, 2.1 Hz, 1H), 7.18 (d, J = 8.4 Hz, 1H), 4.10-4.03 (m, 2H), 3.70-3.64 (m, 2H), 3.35-3.23 (m, 2H), 3.15-3.10 (m, 1H), 3.02-2.92 (m, 2H), 2.86-2.80 (m, 2H), 2.72 (s, 6H), 2.50 (s, 3H), 2.29-2.24 (m, 2H), 2.02-1.95 (m, 2H), 1.22 (d, J = 5.8 Hz, 6H) |

-continued

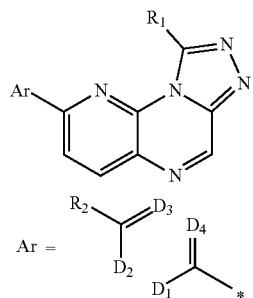

| Example | Ar | R₁ | LC-MS (ESI) | ¹H NMR, 400 MHz |
|---|---|---|---|---|
| 87 | (4-dimethylamino-piperidinyl)-3-CF₃-phenyl | (2S,5R)-2,5-dimethylpiperazinyl | (M + 1) 568.32 | DMSO-d₆: δ 9.18 (s, 1H), 8.53 (d, J = 2.1 Hz, 1H), 8.50 (d, J = 8.4 Hz, 1H), 8.42 (dd, J = 8.4, 1.9 Hz, 1H), 8.31 (d, J = 8.4 Hz, 1H), 7.65 (d, J = 8.5 Hz, 1H), 3.91-3.84 (m, 2H), 3.17-3.12 (m, 2H), 2.90-2.80 (m, 4H), 2.59-2.52 (m, 2H), 2.35-2.29 (m, 1H), 2.29-2.17 (m, 9H), 1.92-1.85 (m, 2H), 1.60-1.51 (m, 2H), 0.96 (d, J = 6.2 Hz, 6H) |
| 88 | (4-dimethylamino-piperidinyl)-2-F-6-CF₃-phenyl | (2S,5R)-2,5-dimethylpiperazinyl | M.W. 585.66 | — |
| 89 | (4-dimethylamino-piperidinyl)-2-Cl-6-CF₃-phenyl | (2S,5R)-2,5-dimethylpiperazinyl | M.W. 602.11 | — |
| 90 | 4-(4-dimethylamino-piperidinyl)-phenyl | 4-dimethylamino-piperidinyl | (M + 1) 500.40 | MeOD: δ 8.97 (s, 1H), 8.34 (d, J = 8.5 Hz, 1H), 8.11-7.99 (m, 3H), 7.11 (d, J = 9.0 Hz, 2H), 4.24-4.14 (m, 2H), 4.06-3.95 (m, 2H), 3.20-3.07 (m, 2H), 2.93-2.80 (m, 2H), 2.70-2.56 (m, 2H), 2.45 (s, 12H), 2.15-2.00 (m, 4H), 2.00-1.89 (m, 2H), 1.72-1.59 (m, 2H) |
| 91 | 4-(4-dimethylamino-piperidinyl)-3-F-phenyl | 4-dimethylamino-piperidinyl | M.W. 517.66 | — |

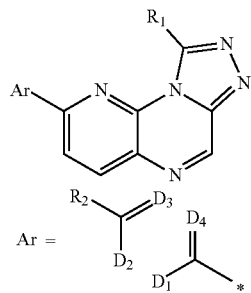

| Example | Ar | R₁ | LC-MS (ESI) | ¹H NMR, 400 MHz |
|---|---|---|---|---|
| 92 | (4-dimethylamino-piperidinyl on 2-chlorophenyl) | (N,N-dimethyl-piperidin-4-yl) | M.W. 534.11 | — |
| 93 | (4-dimethylamino-piperidinyl on 2-trifluoromethylphenyl) | (N,N-dimethyl-piperidin-4-yl) | M.W. 567.67 | — |

The compounds of Examples 94-97 were obtained by firstly preparing tert-butoxycarbonyl protected intermediates using a synthesis process similar to that described with reference to Example 23e, followed by deprotection under an acidic condition (e.g. in a solution of hydrochloric acid in dioxane), the starting materials being 8-bromo-1-((2R,6S)-3,4,5-trimethylpiperazin-1-yl)-[1,2,4]triazolo[4,3-a]quinoxaline (Example 23 d) and corresponding substituted phenylboronic acid pinacol esters.

The compound of Example 98 was prepared using a synthesis process similar to that described with reference to Example 23d-e, the starting materials being 8-bromo-1-((2R,6S)-3,5-dimethylpiperazin-1-yl)-[1,2,4]triazolo[4,3-a]quinoxaline (Example 23c), iodoethane and N,N-dimethyl-1-(4-(4,4,5,5-tetramethyl-1,3,2-dioxaborolan-2-yl)-2-(trifluoromethyl)phenyl)piperidin-4-amine.

The compounds of Examples 99-116 were prepared using a synthesis process similar to that described with reference to Example 3d-e, the starting materials being 2-hydrazino-7-bromoquinoxaline, corresponding heterocyclic carbonyl chloride and corresponding substituted phenylboronic acid pinacol esters.

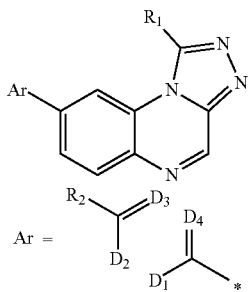

| Example | Ar | R₁ | LC-MS (ESI) | ¹H NMR, 400 MHz |
|---|---|---|---|---|
| 94 | (4-methylamino-piperidinyl on 2-fluorophenyl) | ((2S,6R)-2,6-dimethyl-4-methylpiperazinyl) | (M + 1) 503.29 | DMSO-d₆: δ 9.17 (s, 1H), 8.76-8.63 (m, 1H), 8.06 (d, J = 8.4 Hz, 1H), 7.96 (dd, J = 8.5, 1.8 Hz, 1H), 7.57-7.49 (m, 2H), 7.23-7.16 (m, 1H), 3.50-3.42 (m, 7H), 2.91-2.76 (m, 4H), 2.59-2.55 (m, 1H), 2.35 (s, 3H), 2.29 (s, 3H), 2.00-1.94 (m, 2H), 1.52-1.43 (m, 2H), 1.15-1.02 (m, 6H) |

-continued

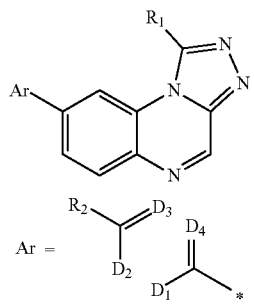

Ar =

| Example | Ar | R₁ | LC-MS (ESI) | ¹H NMR, 400 MHz |
|---|---|---|---|---|
| 95 | (N-methylpiperidin-4-yl)amino, 2-CF₃ phenyl | 2,5-dimethylpiperazine, N-methyl | (M + 1) 553.30 | DMSO-d₆: δ 9.22 (s, 1H), 8.83-8.73 (m, 1H), 8.14 (d, J = 8.4 Hz, 1H), 8.10-7.97 (m, 3H), 7.69 (d, J = 8.4 Hz, 1H), 3.46-3.38 (m, 2H), 3.15-3.08 (m, 2H), 2.91-2.72 (m, 5H), 2.49-2.39 (m, 6H), 2.26 (s, 3H), 2.07-2.00 (m, 2H), 1.62-1.53 (m, 2H), 1.13-1.01 (m, 6H) |
| 96 | (N-ethylpiperidin-4-yl)amino, 2-F phenyl | 2,5-dimethylpiperazine, N-methyl | (M + 1) 517.27 | DMSO-d₆: δ 9.17 (s, 1H), 8.79-8.64 (m, 1H), 8.07 (d, J = 8.2 Hz, 1H), 7.97 (d, J = 7.8 Hz, 1H), 7.60-7.50 (m, 2H), 7.25-7.15 (m, 1H), 3.51-3.41 (m, 7H), 2.93-2.75 (m, 4H), 2.73-2.63 (m, 3H), 2.29 (s, 3H), 2.01-1.93 (m, 2H), 1.55-1.43 (m, 2H), 1.18-0.93 (m, 9H) |
| 97 | (N-ethylpiperidin-4-yl)amino, 2-CF₃ phenyl | 2,5-dimethylpiperazine, N-methyl | (M + 1) 567.32 | DMSO-d₆: δ 9.22 (s, 1H), 8.85-8.74 (m, 1H), 8.14 (d, J = 8.4 Hz, 1H), 8.10-8.02 (m, 2H), 8.00 (s, 1H), 7.69 (d, J = 8.4 Hz, 1H), 3.45-3.39 (m, 2H), 3.14-3.08 (m, 2H), 2.92-2.75 (m, 7H), 2.49-2.41 (m, 3H), 2.26 (s, 3H), 2.05-1.98 (m, 2H), 1.64-1.50 (m, 2H), 1.16-0.98 (m, 9H) |
| 98 | N,N-dimethylpiperidin-4-ylamino, 2-CF₃ phenyl | 2,5-dimethylpiperazine, N-ethyl | M.W. 580.70 | — |
| 99 | N,N-dimethylpiperidin-4-ylamino, 2-CF₃ phenyl | 2,5-dimethylpiperazine, N-isopropyl | M.W. 594.73 | — |

-continued

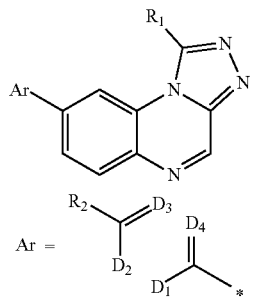

| Example | Ar | R₁ | LC-MS (ESI) | ¹H NMR, 400 MHz |
|---|---|---|---|---|
| 100 | (dimethylamino-propoxy, 2-fluoro phenyl) | (2,6-dimethyl morpholine) | (M + 1) 479.30 | DMSO-d₆: δ 9.18 (s, 1H), 8.73-8.55 (m, 1H), 8.07 (d, J = 8.4 Hz, 1H), 7.95 (dd, J = 8.5, 1.8 Hz, 1H), 7.62 d, J = 12.5 Hz 1H), 7.52 (d, J = 8.1 Hz, 1H), 7.38 (t, J = 8.7 Hz, 1H), 4.17 (t, J = 6.4 Hz, 2H), 4.02-3.90 (m, 2H), 3.50-3.43 (m, 2H), 2.83-2.69 (m, 2H), 2.40 (t, J = 7.0 Hz, 2H), 2.18 (s, 6H), 1.95-1.87 (m, 2H), 1.27-1.08 (m, 6H) |
| 101 | (dimethylamino-propoxy, 2-chloro phenyl) | (2,6-dimethyl morpholine) | (M + 1) 495.28 | DMSO-d₆: δ 9.19 (s, 1H), 8.66-8.57 (m, 1H), 8.08 (d, J = 8.4 Hz, 1H), 7.96 (dd, J = 8.4, 1.6 Hz, 1H), 7.79 (s, 1H), 7.68 (d, J = 8.3 Hz, 1H), 7.36 (d, J = 8.6 Hz, 1H), 4.19 (t, J = 6.3 Hz, 2H), 4.00-3.92 (m, 2H), 3.50-3.46 (m, 2H), 2.84-2.70 (m, 2H), 2.45 (t, J = 7.0 Hz, 2H), 2.19 (s, 6H), 1.96-1.90 (m, 2H), 1.25-1.16 (m, 6H) |
| 102 | (dimethylamino-propoxy, 2-trifluoromethyl phenyl) | (2,6-dimethyl morpholine) | (M + 1) 528.87 | DMSO-d₆: δ 9.20 (s, 1H), 8.80-8.59 (m, 1H), 8.11 (d, J = 8.4 Hz, 1H), 8.05-7.98 (m, 2H), 7.94 (s, 1H), 7.48 (d, J = 8.7 Hz, 1H), 4.25 (t, J = 6.0 Hz, 2H), 3.98-3.89 (m, 2H), 3.51-3.42 (m, 2H), 2.88-2.62 (m, 2H), 2.50-2.43 (m, 2H), 2.23 (s, 6H), 1.97-1.90 (m, 2H), 1.21-1.09 (m, 6H) |
| 103 | (4-(dimethylamino)piperidinyl phenyl) | (2,6-dimethyl morpholine) | (M + 1) 486.33 | DMSO-d₆: δ 9.16 (s, 1H), 8.76-8.65 (m, 1H), 8.07 (d, J = 8.5 Hz, 1H), 7.94 (d, J = 8.4 Hz, 1H), 7.65 (d, J = 8.4 Hz, 2H), 7.14 (d, J = 8.8 Hz, 2H), 3.98-3.91 (m, 2H), 3.50-3.45 (m, 2H), 3.30-3.25 (m, 4H), 2.83-2.76 (m, 2H), 2.51 (s, 6H), 2.40-2.38 (m, 1H), 2.00-1.91 (m, 2H), 1.61-1.47 (m, 2H), 1.24-1.06 (m, 6H) |
| 104 | (4-(dimethylamino)piperidinyl, 2-fluoro phenyl) | (2,6-dimethyl morpholine) | (M + 1) 504.28 | CDCl₃: δ 9.11 (s, 1H), 8.76-8.62 (m, 1H), 8.12 (d, J = 8.4 Hz, 1H), 7.79 (dd, J = 8.5, 1.9 Hz, 1H), 7.40-7.30 (m, 2H), 7.11-7.06 (m, 1H), 4.14-3.96 (m, 2H), 3.70-3.63 (m, 2H), 3.48-3.38 (m, 2H), 3.11-2.97 (m, 2H), 2.82 (t, J = 11.3 Hz, 2H), 2.56-2.37 (m, 7H), 2.08-2.01 (m, 2H), 1.86-1.77 (m, 2H), 1.37-1.27 (m, 6H) |

-continued

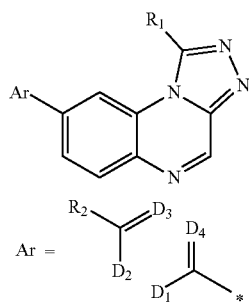

| Example | Ar | R₁ | LC-MS (ESI) | ¹H NMR, 400 MHz |
|---|---|---|---|---|
| 105 | dimethylamino-piperidine on 2-Cl phenyl | 2,6-dimethylmorpholine | (M + 1) 520.27 | DMSO-d₆: δ 9.21 (s, 1H), 8.71-8.59 (m, 1H), 8.10 (d, J = 8.4 Hz, 1H), 7.98 (d, J = 8.3 Hz, 1H), 7.77 (s, 1H), 7.69 (d, J = 7.8 Hz, 1H), 7.34 (d, J = 8.4 Hz, 1H), 4.03-3.92 (m, 2H), 3.50-3.42 (m, 4H), 2.85-2.64 (m, 4H), 2.34-2.20 (m, 7H), 1.94-1.84 (m, 2H), 1.65-1.54 (m, 2H), 1.29-1.14 (m, 6H) |
| 106 | dimethylamino-piperidine on 2-CF₃ phenyl | 2,6-dimethylmorpholine | M.W. 553.63 | — |
| 107 | methylamino-piperidine on 2-CF₃ phenyl | 2,6-dimethylmorpholine | M.W. 539.61 | — |
| 108 | ethylamino-piperidine on 2-CF₃ phenyl | 2,6-dimethylmorpholine | M.W. 553.63 | — |
| 109 | 3-(dimethylamino)propoxy on 2-CF₃ phenyl | 2,6-dimethyltetrahydropyran | M.W. 527.59 | — |

-continued

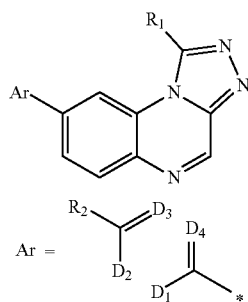

| Example | Ar | R₁ | LC-MS (ESI) | ¹H NMR, 400 MHz |
|---|---|---|---|---|
| 110 | 4-(dimethylamino)piperidin-1-yl on 2-CF₃ phenyl | 2,6-dimethyltetrahydropyran-4-yl | M.W. 552.65 | — |
| 111 | 3-(dimethylamino)propoxy on 2-CF₃ phenyl | piperidin-1-yl | (M + 1) 498.80 | DMSO-d₆: δ 9.19 (s, 1H), 8.72 (s, 1H), 8.12-7.97 (m, 4H), 7.48 (d, J = 8.7 Hz, 1H), 4.24 (t, J = 6.0 Hz, 2H), 3.55-3.45 (m, 2H), 3.08-2.96 (m, 2H), 2.44 (t, J = 6.9 Hz, 2H), 2.19 (s, 6H), 1.95-1.81 (m, 5H), 1.77-1.66 (m, 2H), 1.55-1.43 (m, 1H) |
| 112 | 4-(dimethylamino)piperidin-1-yl on 2-F phenyl | piperidin-1-yl | (M + 1) 474.29 | DMSO-d₆: δ 9.16 (s, 1H), 8.65 (s, 1H), 8.07 (d, J = 7.8 Hz, 1H), 7.95 (d, J = 8.2 Hz, 1H), 7.60-7.51 (m, 2H), 7.25-7.18 (m, 1H), 3.56-3.47 (m, 4H), 3.09-2.99 (m, 2H), 2.80-2.71 (m, 2H), 2.33-2.22 (m, 7H), 1.94-1.82 (m, 5H), 1.80-1.70 (m, 2H), 1.63-1.49 (m, 3H) |
| 113 | 4-(dimethylamino)piperidin-1-yl on 2-Cl phenyl | piperidin-1-yl | (M + 1) 490.28 | DMSO-d₆: δ 9.18 (s, 1H), 8.66 (d, J = 1.8 Hz, 1H), 8.08 (d, J = 8.4 Hz, 1H), 7.96 (dd, J = 8.5, 1.9 Hz, 1H), 7.82 (d, J = 2.2 Hz, 1H), 7.71 (dd, J = 8.4, 2.2 Hz, 1H), 7.32 (d, J = 8.4 Hz, 1H), 3.54-3.47 (m, 2H), 3.44-3.40 (m, 2H), 3.09-2.99 (m, 2H), 2.75-2.68 (m, 2H), 2.32-2.26 (m, 1H), 2.24 (s, 6H), 1.94-1.83 (m, 5H), 1.80-1.71 (m, 2H), 1.65-1.51 (m, 3H) |

-continued

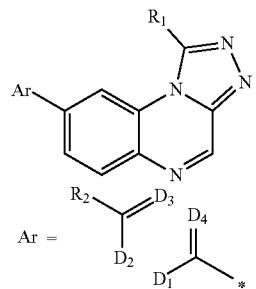

| Example | Ar | R₁ | LC-MS (ESI) | ¹H NMR, 400 MHz |
|---------|-----|-----|-------------|------------------|
| 114 | 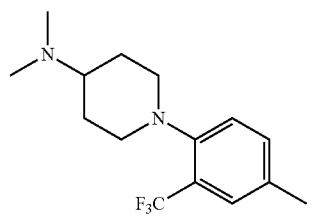 [SMILES: *c1ccc(N2CCC(N(C)C)CC2)c(C(F)(F)F)c1] | 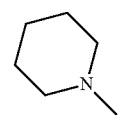 | M.W. 523.61 | — |
| 115 | 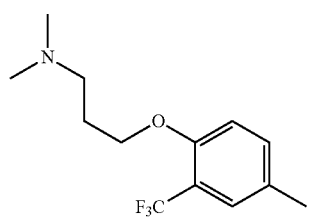 | 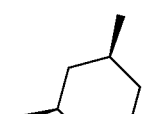 | M.W. 526.61 | — |
| 116 | 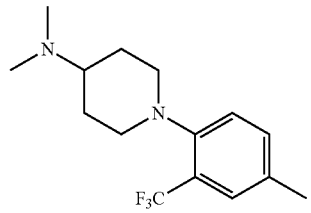 [SMILES: *c1ccc(N2CCC(N(C)C)CC2)c(C(F)(F)F)c1] | 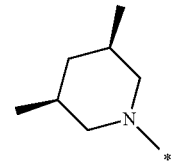 | M.W. 551.66 | — |

The compounds of Examples 117-120 were prepared from 2-chloro-9-((3S,5R)-3,4,5-trimethylpiperazin-1-yl) pyrido[3,2-e][1,2,4]triazolo[4,3-a]pyrazine (the intermediate of Example 80) and the corresponding pinacol phenylboronate using a procedure similar to those described for the synthesis of compound of Example 23e.

The compound of Example 121 was prepared from 2-chloro-9-((3S,5R)-3,5-dimethylpiperazin-1-yl)pyrido[3,2-e][1,2,4]triazolo[4,3-a]pyrazine (the intermediate of Example 80), and iodoethane and N,N-dimethyl-1-(4-(4,4,5,5-tetramethyl-1,3,2-dioxaborolan-2-yl)-2-(trifluoromethyl)phenyl)piperidin-4-amine using a procedure similar to those described for the syntheses of compounds of Examples 23d-e.

The compound of Example 122 was prepared using a synthesis process similar to that described with reference to Example 31 c-d, the starting materials being 3-hydrazino-6-chloropyrido[2,3-b]pyrazine, (3S,5R)-4-isopropyl-3,5-dimethylpiperazin-1-ylcarbonyl chloride and N,N-dimethyl-1-(4-(4,4,5,5-tetramethyl-1,3,2-dioxaborolan-2-yl)-2-(trifluoromethyl)phenyl)piperidin-4-amine.

The compounds of Examples 123-145 were prepared using a synthesis process similar to that described with reference to Example 31 b-e, the starting materials being 3-hydrazino-6-chloropyrido[2,3-b]pyrazine (Example 31a), tetrahydropyran-4-carbaldehyde or corresponding substituted heterocyclic carbonyl chlorides and corresponding phenylboronic acid pinacol esters.

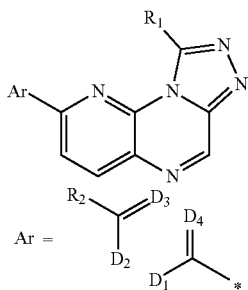

| Example | Ar | R₁ | LC-MS (ESI) | ¹H NMR, 400 MHz |
|---|---|---|---|---|
| 117 | (4-methylamino-piperidinyl)-2-fluorophenyl | (2S,5R)-dimethylpiperazinyl | (M + 1) 504.29 | DMSO-d₆: δ 9.16 (s, 1H), 8.44 (d, J = 8.4 Hz, 1H), 8.28-8.25 (m, 1H), 8.09-8.03 (m, 1H), 8.03-7.98 (m, 1H), 7.23-7.17 (m, 1H), 3.92-3.86 (m, 2H), 3.60-3.55 (m, 2H), 2.94-2.81 (m, 5H), 2.61-2.55 (m, 2H), 2.49 (s, 3H), 2.27 (s, 3H), 2.10-2.03 (m, 2H), 1.66-1.56 (m, 2H), 1.03 (d, J = 6.1 Hz, 6H) |
| 118 | (4-methylamino-piperidinyl)-2-trifluoromethylphenyl | (2S,5R)-dimethylpiperazinyl | (M + 1) 554.29 | DMSO-d₆: δ 9.19 (s, 1H), 8.59-8.47 (m, 2H), 8.43 (d, J = 8.6 Hz, 1H), 8.32 (d, J = 8.3 Hz, 1H), 7.67 (d, J = 8.3 Hz, 1H), 3.94-3.82 (m, 2H), 3.19-3.08 (m, 2H), 2.96-2.77 (m, 4H), 2.77-2.55 (m, 3H), 2.43 (s, 3H), 2.23 (s, 3H), 2.08-1.93 (m, 2H), 1.61-1.46 (m, 2H), 0.96 (d, J = 6.1 Hz, 6H) |
| 119 | (4-ethylamino-piperidinyl)-2-fluorophenyl | (2S,5R)-dimethylpiperazinyl | (M + 1) 518.38 | DMSO-d₆: δ 9.15 (s, 1H), 8.44 (d, J = 8.4 Hz, 1H), 8.25 (d, J = 8.5 Hz, 1H), 8.09-7.98 (m, 2H), 7.22-7.16 (m, 1H), 3.93-3.86 (m, 2H), 3.61-3.54 (m, 2H), 3.01-2.95 (m, 1H), 2.93-2.78 (m, 6H), 2.62-2.56 (m, 2H), 2.27 (s, 3H), 2.10-2.01 (m, 2H), 1.66-1.56 (m, 2H), 1.15 (t, J = 7.1 Hz, 3H), 1.03 (d, J = 6.1 Hz, 6H) |
| 120 | (4-ethylamino-piperidinyl)-2-trifluoromethylphenyl | (2S,5R)-dimethylpiperazinyl | M.W. 567.67 | — |
| 121 | (4-dimethylamino-piperidinyl)-2-trifluoromethylphenyl | (2S,5R)-dimethyl-N-ethylpiperazinyl | M.W. 581.69 | — |
| 122 | (4-dimethylamino-piperidinyl)-2-trifluoromethylphenyl | (2S,5R)-dimethyl-N-isopropylpiperazinyl | M.W. 595.72 | — |

-continued

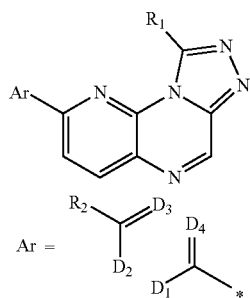

| Example | Ar | R₁ | LC-MS (ESI) | ¹H NMR, 400 MHz |
|---|---|---|---|---|
| 123 | (dimethylaminopropoxy-trifluoromethylphenyl) | (2,6-dimethylmorpholinyl) | (M + 1) 530.32 | DMSO-d₆: δ 9.19 (s, 1H), 8.56-8.40 (m, 3H), 8.34 (d, J = 8.4 Hz, 1H), 7.51 (d, J = 8.5 Hz, 1H), 4.27 (t, J = 6.1 Hz, 2H), 4.10-3.83 (m, 4H), 2.87-2.71 (m, 2H), 2.40 (t, J = 6.9 Hz, 2H), 2.15 (s, 6H), 2.00-1.81 (m, 2H), 1.00 (d, J = 8.0 Hz, 6H) |
| 124 | (4-(dimethylamino)piperidinyl-phenyl) | (2,6-dimethylmorpholinyl) | (M + 1) 487.35 | DMSO-d₆: δ 9.11 (s, 1H), 8.38 (d, J = 8.5 Hz, 1H), 8.16 (d, J = 8.5 Hz, 1H), 8.08 (d, J = 8.9 Hz, 2H), 7.12 (d, J = 8.8 Hz, 2H), 4.13-3.90 (m, 5H), 2.95-2.69 (m, 5H), 2.40-2.28 (m, 1H), 2.22 (s, 6H), 1.94-1.77 (m, 2H), 1.57-1.39 (m, 2H) |
| 125 | (4-(dimethylamino)piperidinyl-fluorophenyl) | (2,6-dimethylmorpholinyl) | (M + 1) 505.33 | DMSO-d₆: δ 9.17 (s, 1H), 8.45 (d, J = 8.5 Hz, 1H), 8.25 (d, J = 7.5 Hz, 1H), 7.98-7.95 (m, 2H), 7.22 (t, J = 8.0 Hz, 1H), 4.13-3.90 (m, 4H), 3.70-3.54 (m, 2H), 2.92-2.70 (m, 4H), 2.41-2.00 (m, 7H), 1.95-1.78 (m, 2H), 1.65-1.41 (m, 2H), 1.14 (d, J = 5.9 Hz, 6H) |
| 126 | (4-(dimethylamino)piperidinyl-chlorophenyl) | (2,6-dimethylmorpholinyl) | M.W. 521.07 | — |
| 127 | (4-(dimethylamino)piperidinyl-trifluoromethylphenyl) | (2,6-dimethylmorpholinyl) | M.W. 554.62 | — |

-continued

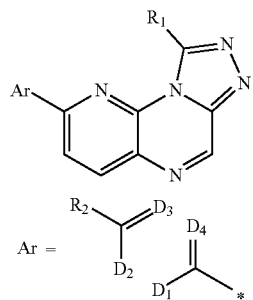

| Example | Ar | R₁ | LC-MS (ESI) | ¹H NMR, 400 MHz |
|---|---|---|---|---|
| 128 | [4-(methylamino)piperidin-1-yl]-2-(trifluoromethyl)phenyl | (2R,6S)-2,6-dimethylmorpholin-4-yl | M.W. 540.60 | — |
| 129 | [4-(ethylamino)piperidin-1-yl]-2-(trifluoromethyl)phenyl | (2R,6S)-2,6-dimethylmorpholin-4-yl | M.W. 554.62 | — |
| 130 | 4-[3-(dimethylamino)propoxy]-3-(trifluoromethyl)phenyl | 2,6-dimethyltetrahydro-2H-pyran-4-yl | M.W. 528.58 | — |
| 131 | [4-(dimethylamino)piperidin-1-yl]-2-(trifluoromethyl)phenyl | 2,6-dimethyltetrahydro-2H-pyran-4-yl | M.W. 553.63 | — |
| 132 | 4-[3-(dimethylamino)propoxy]-3-(trifluoromethyl)phenyl | piperidin-1-yl | M.W. 499.54 | — |

-continued

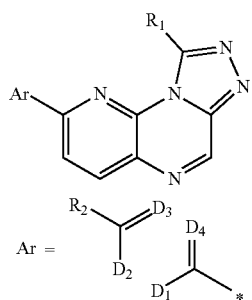

| Example | Ar | R₁ | LC-MS (ESI) | ¹H NMR, 400 MHz |
|---|---|---|---|---|
| 133 | (4-(4-dimethylamino-piperidin-1-yl)phenyl) | piperidine | (M + 1) 457.31 | DMSO-d₆: δ 9.09 (s, 1H), 8.36 (d, J = 8.4 Hz, 1H), 8.20-8.08 (m, 3H), 7.11 (d, J = 9.0 Hz, 2H), 3.99-3.90 (m, 2H), 3.59-3.47 (m, 4H), 2.83 (t, J = 11.2 Hz, 2H), 2.37-2.27 (m, 1H), 2.21 (s, 6H), 1.96-1.75 (m, 6H), 1.73-1.61 (m, 2H), 1.54-1.37 (m, 2H) |
| 134 | (4-(4-dimethylamino-piperidin-1-yl)-3-fluorophenyl) | piperidine | (M + 1) 475.30 | DMSO-d₆: δ 9.14 (s, 1H), 8.43 (d, J = 8.4 Hz, 1H), 8.22 (d, J = 8.0 Hz, 1H), 8.05-8.00 (m, 2H), 7.20 (t, J = 8.9 Hz, 1H), 3.70-3.46 (m, 6H), 2.79 (t, J = 11.1 Hz, 2H), 2.38-2.28 (m, 1H), 2.24 (s, 6H), 2.05-1.72 (m, 6H), 1.73-1.63 (m, 2H), 1.62-1.45 (m, 2H) |
| 135 | (4-(4-dimethylamino-piperidin-1-yl)-3-chlorophenyl) | piperidine | M.W. 491.04 | — |
| 136 | (4-(4-dimethylamino-piperidin-1-yl)-3-trifluoromethylphenyl) | piperidine | M.W. 524.60 | — |
| 137 | (4-(3-dimethylaminopropoxy)-3-trifluoromethylphenyl) | (3,5-dimethylpiperidine) | M.W. 527.60 | — |

-continued

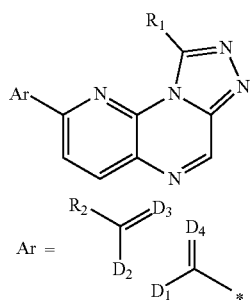

| Example | Ar | R₁ | LC-MS (ESI) | ¹H NMR, 400 MHz |
|---|---|---|---|---|
| 138 | (dimethylamino-piperidinyl-trifluoromethylphenyl) | (3,5-dimethylpiperidinyl) | M.W. 552.65 | — |
| 139 | (dimethylaminopropoxy-fluorophenyl) | (tetrahydropyranyl) | (M + 1) 451.27 | CDCl₃: δ 9.26 (s, 1H), 8.49 (d, J = 8.5 Hz, 1H), 8.03 (d, J = 8.5 Hz, 1H), 7.92 (dd, J = 12.3, 2.2 Hz, 1H), 7.87-7.84 (m, 1H), 7.19-7.15 (m, 1H), 4.54-4.50 (m, 1H), 4.33-4.29 (m, 2H), 4.27-4.22 (m, 2H), 3.81-3.75 (m, 2H), 3.14-3.07 (m, 2H), 2.73 (s, 6H), 2.42-2.29 (m, 6H) |
| 140 | (dimethylaminopropoxy-chlorophenyl) | (tetrahydropyranyl) | (M + 1) 467.20 | CDCl₃: δ 9.26 (s, 1H), 8.50 (d, J = 8.4 Hz, 1H), 8.26 (d, J = 1.9 Hz, 1H), 8.04 (d, J = 8.4 Hz, 1H), 7.99-7.96 (m, 1H), 7.16-7.12 (m, 1H), 4.56-4.52 (m, 1H), 4.40-4.33 (m, 2H), 4.27-4.22 (m, 2H), 3.85-3.79 (m, 2H), 3.38-3.32 (m, 2H), 2.91 (s, 6H), 2.59-2.52 (m, 2H), 2.32 (s, 4H) |
| 141 | (dimethylaminopropoxy-trifluoromethylphenyl) | (tetrahydropyranyl) | M.W. 500.53 | — |
| 142 | (dimethylamino-piperidinyl-fluorophenyl) | (tetrahydropyranyl) | (M + 1) 476.30 | CDCl₃: δ 9.24 (s, 1H), 8.47 (d, J = 8.5 Hz, 1H), 8.02 (d, J = 8.5 Hz, 1H), 7.90-7.81 (m, 2H), 7.11-7.05 (m, 1H), 4.57-4.50 (m, 1H), 4.28-4.20 (m, 2H), 3.85-3.72 (m, 4H), 3.02-2.95 (m, 1H), 2.93-2.85 (m, 2H), 2.66 (s, 6H), 2.38-2.27 (m, 4H), 2.26-2.20 (m, 2H), 1.97-1.91 (m, 2H) |

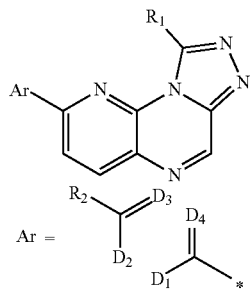

| Example | Ar | R₁ | LC-MS (ESI) | ¹H NMR, 400 MHz |
|---|---|---|---|---|
| 143 | (dimethylamino-piperidinyl)-chlorophenyl | tetrahydropyran-4-yl | M.W. 492.02 | — |
| 144 | (dimethylamino-piperidinyl)-trifluoromethylphenyl | tetrahydropyran-4-yl | M.W. 525.58 | — |
| 145 | (dimethylamino-piperidinyl)-fluorophenyl | tetrahydropyran-4-yl | M.W. 475.57 | — |

The compounds of Examples 146-151 were prepared from 8-bromo-1-((2R,6S)-3,4,5-trimethylpiperazin-1-yl)-[1,2,4]triazolo[4,3-a]quinoxaline (Example 23d) and the corresponding pinacol phenylboronate using a procedure similar to those described for the synthesis of compound of Example 23e.

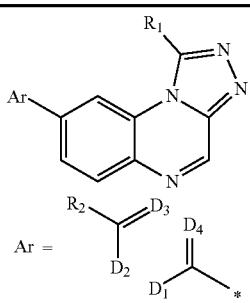

| Example | Ar | R1 | LC-MS (ESI) | ¹H NMR, 400 MHz |
|---|---|---|---|---|
| 146 | (dimethylaminopropoxy)-bromophenyl | (2R,6S)-trimethylpiperazinyl | M.W. 552.52 | — |

-continued

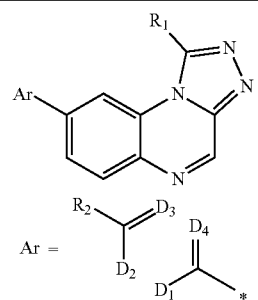

| Example | Ar | R1 | LC-MS (ESI) | ¹H NMR, 400 MHz |
|---|---|---|---|---|
| 147 | (dimethylaminopropoxy-fluorophenyl) | (dimethyl piperazinyl) | M.W. 491.62 | — |
| 148 | (dimethylaminopropoxy-fluoro-trifluoromethylphenyl) | (dimethyl piperazinyl) | M.W. 559.61 | — |
| 149 | (dimethylaminopropoxy-chloro-trifluoromethylphenyl) | (dimethyl piperazinyl) | M.W. 576.07 | — |
| 150 | (dimethylaminopropoxy-chloro-fluorophenyl) | (dimethyl piperazinyl) | M.W. 526.06 | — |
| 151 | (dimethylamino-piperidinyl-bromophenyl) | (dimethyl piperazinyl) | M.W. 577.58 | — |

Example 152

In Vitro Inhibition of ATM by N,N-dimethyl-3-(4-(1-(tetrahydro-2H-pyran-4-yl)-[1,2,4]triazolo[4,3-a]quinoxalin-8-yl)phenoxy)propan-1-amine and its Analogues was Determined by ATM Kinase Assay ATM enzyme (human) was added to the reaction solution containing 30 nM GST-cMyc-p53 and 10 μM Mg/ATP, and then 50 times the concentration of the tested compound (or reference compound AZD0156) dissolved in 100% DMSO was added to the final concentration of 10/1/0.1/0.01/0.001 μM. The reaction was initiated by the addition of a Mg/ATP mixture and incubation for 30 minutes at room temperature, the reaction was quenched by the addition of a stop solution containing EDTA. Finally, the detection buffer containing the d2-labeled anti-GST monoclonal antibody and the europium-labeled anti-phospho p53 (Ser15) antibody was added. The plate was then read in time resolved fluorescence mode and the homogeneous time resolved fluorescence (HTRF) signal was determined according to the equation: $HTRF = 10000 \times (Em_{665nm}/Em_{620nm})$. Each compound sample was repeated in duplicate. The experiment negative control was all components except of the ATM enzyme and the positive control contained all components. All reactions were quenched by adding EDTA. Table 1 summarizes the ATM kinase inhibition data of compounds (% inhibition rate).

TABLE 1

Inhibition of ATM kinase by N,N-dimethyl-3-(4-(1-(tetrahydro-2H-pyran-4-yl)-[1,2,4]triazolo[4,3-a]quinoxalin-8-yl)phenoxy)propan-1-amine and its analogues

| Example | | | | | | | | | |
|---|---|---|---|---|---|---|---|---|---|
| Example | 1 | | | 2 | | | 3 | | |
| C (μm) | 10 | | | 1 | | | 10 | | |
| Inh (%) | 90 | | | 57 | | | 100 | | |
| Example | 4 | | | 5 | | | 6 | | |
| C (μm) | 10 | | | 1 | 0.1 | 0.01 | 1 | | |
| Inh (%) | 100 | | | 96 | 47 | 7 | 57 | | |
| Example | 7 | | | 8 | | | 9 | | |
| C (μm) | 1 | | | 1 | | | 1 | | |
| Inh (%) | 40 | | | 38 | | | 72 | | |
| Example | 10 | | | 11 | | | 12 | | |
| C (μm) | 1 | | | 1 | | 1 | 0.1 | 0.01 | |
| Inh (%) | 85 | | | 64 | | 100 | 93 | 50 | |
| Example | 13 | | | 14 | | | 15 | | |
| C (μm) | 1 | 0.1 | 0.01 | 1 | 0.1 | 0.01 | 1 | 0.1 | 0.01 |
| Inh (%) | 93 | 49 | 8 | 96 | 52 | 20 | 98 | 80 | 33 |
| Example | 18 | | | 20 | | | 21 | | |
| C (μm) | 1 | | | 1 | 0.1 | 0.01 | 1 | | |
| Inh (%) | 34 | | | 100 | 99 | 79 | 100 | | |
| Example | 22 | | | 23 | | | 27 | | |
| C (μm) | 1 | | | 1 | 0.1 | 0.01 | 0.001 | 1 | 0.1 | 0.01 |
| Inh (%) | 100 | | | 100 | 99 | 81 | 60 | 99 | 84 | 43 |
| Example | 29 | | | 30 | | | 31 | | |
| C (μm) | 1 | 0.1 | 0.01 | 1 | | | 1 | 0.1 | 0.01 |
| Inh (%) | 97 | 81 | 34 | 14 | | | 100 | 92 | 51 |
| Example | 37 | | | 39 | | | 40 | | |
| C (μm) | 1 | | | 1 | | 1 | 0.1 | 0.01 | |
| Inh (%) | 18 | | | 62 | | 99 | 81 | 33 | |
| Example | 41 | | | 42 | | | 43 | | |
| C (μm) | 1 | 0.1 | 0.01 | 1 | 0.1 | 0.01 | 1 | 0.1 | 0.01 |
| Inh (%) | 99 | 81 | 33 | 99 | 90 | 68 | 100 | 89 | 47 |
| Example | 44 | | | 45 | | | 46 | | |
| C (μm) | 1 | 0.1 | 0.01 | 1 | 0.1 | 0.01 | 1 | | |
| Inh (%) | 100 | 94 | 67 | 100 | 94 | 67 | 100 | | |
| Example | 47 | | | 48 | | | 49 | | |
| C (μm) | 1 | 0.1 | 0.01 | 1 | 0.1 | 0.01 | 1 | | |
| Inh (%) | 100 | 96 | 72 | 100 | 93 | 62 | 100 | | |
| Example | 50 | | | 51 | | | 52 | | |
| C (μm) | 1 | | | 1 | | | 1 | | |
| Inh (%) | 80 | | | 74 | | | 98 | | |
| Example | 53 | | | 54 | | | 57 | | |
| C (μm) | 1 | | | 1 | | 1 | 0.1 | 0.01 | 0.001 |
| Inh (%) | 77 | | | 82 | | 100 | 100 | 98 | 60 |
| Example | 58 | | | 64 | | | 65 | | |
| C (μm) | 1 | 0.1 | 0.01 | 0.001 | 1 | | 1 | 0.1 | 0.01 |
| Inh (%) | 100 | 100 | 89 | 38 | 98 | | 100 | 80 | 37 |
| Example | 66 | | | 67 | | | 68 | | |
| C (μm) | 1 | | | 1 | | | 1 | | |
| Inh (%) | 100 | | | 19 | | | 0 | | |
| Example | 69 | | | 70 | | | 71 | | |
| C (μm) | 1 | | | 1 | | | 1 | | |
| Inh (%) | 14 | | | 4 | | | 19 | | |
| Example | 72 | | | 73 | | | 74 | | |
| C (μm) | 1 | 0.1 | 0.01 | 0.001 | 1 | | 1 | 0.1 | 0.01 |
| Inh (%) | 99 | 97 | 82 | 39 | 100 | | 100 | 96 | 66 |
| Example | 75 | | | 76 | | | 77 | | |
| C (μm) | 1 | | | 1 | | | 1 | | |
| Inh (%) | 100 | | | 100 | | | 97 | | |

TABLE 1-continued

Inhibition of ATM kinase by N,N-dimethyl-3-(4-(1-(tetrahydro-2H-pyran-4-yl)-[1,2,4]triazolo[4,3-a]quinoxalin-8-yl)phenoxy)propan-1-amine and its analogues

| Example | 78 | | | 79 | | | AZD0156 |
|---|---|---|---|---|---|---|---|
| C (μm) | 1 | 0.1 | 0.01 | 1 | 0.1 | 0.01 | 1 |
| Inh (%) | 98 | 94 | 67 | 94 | 62 | 21 | 100 |

The compounds were serially diluted to 10 concentrations with 100% DMSO at the ratio of 1:3 and 1:10 (the last concentration was negative control of DMSO), then added to the ATM buffer and diluted to a final concentration of 10, 3, 1, 0.3, 0.1, 0.1, 0.03, 0.01, 0.003, 0.001 and 0 μM, respectively. ATM kinase inhibition was detected by using the method described above. The curve equation for calculating $IC_{50}$ value is as follows:

$$Y(Inh\ \%) = \frac{100}{1 + 10^{(logIC_{50} - logC) \times D}}$$

wherein, C is the concentration of compound and D is the slope factor. Table 2 summarizes the $IC_{50}$ values of compounds inhibiting ATM kinase.

TABLE 2

Inhibitory effects of N,N-dimethyl-3-(4-(1-(tetrahydro-2H-pyran-4-yl)-[1,2,4]triazolo[4,3-a]quinoxalin-8-yl)phenoxy)propan-1-amine and its analogues on ATM kinase ($IC_{50}$ value)

| Example | 3 | 4 |
|---|---|---|
| $IC_{50}$ (nM) | 19 | 9 |

Therefore, N,N-dimethyl-3-(4-(1-(tetrahydro-2H-pyran-4-yl)-[1,2,4]triazolo[4,3-a]quinoxalin-8-yl)phenoxy)propan-1-amine (Example 4) and its analogues show a good inhibitory effect on ATM kinase by ATM kinase (human) assay. For example, the inhibitory effect of Example 57 at 1 nM on ATM kinase is more than 50%.

Example 153

Inhibitory effects of N,N-dimethyl-3-(4-(1-(tetrahydro-2H-pyran-4-yl)-[1,2,4]triazolo[4,3-a]quinoxalin-8-yl)phenoxy)propan-1-amine and its Analogues Combined with CPT-11 on the Growth of Human Colon Cancer Cell SW620 were Determined by MTT Assay The revived SW620 cells were cultured and passaged until they grew well and had a confluence about 90%. SW620 cells were digested by trypsinase, centrifuged at 800 rpm for 5 minutes, the supernatant was discarded, resuspended with fresh medium (RPMI 1640 medium+10% FBS) and counted. The cells were seeded into 96-well cell culture plate with appropriate cell density and incubated overnight in a 37° C. 5% $CO_2$ incubator. The stock solutions of the tested compound and the reference compound AZD0156 were serially diluted to 8 concentrations by DMSO at the ratios of 1:3 and 1:10, respectively, the first concentration was 10 μM or 1 μM, and the last concentration was negative control of DMSO (0 μM, the final concentration of DMSO was 1%). 5 μL of each concentration was added to 120 μL of medium (25 times diluted) and mixed by shaking. The overnight cells were taken and the culture medium was removed, 195 μL of fresh medium containing 205 nM CPT-11 was added to each well, and 5 μL of diluted medium containing the corresponding concentration of the tested sample was added respectively, and the culture plate was then placed in the 5% $CO_2$ cell culture incubator at 37° C. for 5 days. After removing the original solution, 100 pt of fresh serum-free DMEM medium containing MTT (0.5 mg/mL) was added to each well, the culture was continued. After 4 hours, the original solution was removed, 100 μL of DMSO was added into each well, the 96-well plates were shaken away from light for 10 minutes and placed in a multi-function reader to read the absorbance at the wavelength of 552/630/690 nm. GraphPad Prism 6.0 was used to analyze the data. The inhibitory activity of compounds on cell proliferation was plotted based on cell viability and compound concentration. The $IC_{50}$ value was fitted by a sigmoidal dose response curve equation Y=100/(1+10^(Log C–Log $IC_{50}$)), where C was the concentration of compound.

Table 3 summarizes the inhibitory effects of compounds combined with CPT-11 on the growth of human colon cancer cell SW620 ($IC_{50}$).

TABLE 3

Inhibitory effects of N,N-dimethyl-3-(4-(1-(tetrahydro-2H-pyran-4-yl)-[1,2,4]triazolo[4,3-a]quinoxalin-8-yl)phenoxy)propan-1-amine and its analogues combined with CPT-11 on the growth of human colon cancer cell SW620

| Example | 1 | 2 | 3 | 4 | 5 | 6 |
|---|---|---|---|---|---|---|
| $IC_{50}$ (nm) | >$10^5$ | >$10^5$ | 661.4 | 328.3 | >$10^5$ | >$10^5$ |
| Example | 7 | 8 | 9 | 10 | 11 | 12 |
| $IC_{50}$ (nm) | 3104 | 3299 | 1939 | 5212 | >$10^5$ | 173.4 |
| Example | 13 | 14 | 15 | 18 | 20 | 21 |
| $IC_{50}$ (nm) | >$10^5$ | >$10^5$ | 485.4 | >$10^5$ | 143.5 | 334.3 |
| Example | 22 | 23 | 26 | 27 | 29 | 30 |
| $IC_{50}$ (nm) | 412.8 | 65.14 | 56.97 | 469.6 | 1211 | >$10^4$ |
| Example | 31 | 37 | 39 | 40 | 41 | 42 |
| $IC_{50}$ (nm) | 262.2 | 4249 | >$10^5$ | >$10^5$ | 455.5 | 211.2 |
| Example | 43 | 44 | 45 | 46 | 47 | 48 |
| $IC_{50}$ (nm) | 357.2 | 152.0 | 170.3 | 611.8 | 127.7 | 184.4 |
| Example | 49 | 50 | 51 | 52 | 53 | 54 |
| $IC_{50}$ (nm) | 1032 | >$10^4$ | >$10^4$ | >$10^4$ | >$10^5$ | >$10^5$ |
| Example | 57 | 58 | 59 | 64 | 65 | 66 |
| $IC_{50}$ (nm) | 11.80 | 47.47 | 14.40 | >$10^4$ | 402.1 | 589.3 |
| Example | 67 | 68 | 69 | 70 | 71 | 72 |
| $IC_{50}$ (nm) | >$10^5$ | >$10^5$ | >$10^4$ | >$10^4$ | >$10^5$ | 62.85 |
| Example | 73 | 74 | 75 | 76 | 77 | 78 |
| $IC_{50}$ (nm) | 190.9 | 199.1 | 157.9 | 817.8 | 1014 | 664.2 |
| Example | 79 | 80 | 81 | 82 | 83 | 84 |
| $IC_{50}$ (nm) | 1983 | 163.5 | 138.0 | 189.3 | 147.9 | 70.47 |
| Example | 85 | 90 | 94 | 96 | 102 | 103 |
| $IC_{50}$ (nm) | 41.29 | 981.0 | 13.02 | 15.03 | 21.12 | 176.2 |
| Example | 104 | 111 | 112 | 117 | 119 | 139 |
| $IC_{50}$ (nm) | 28.24 | 16.18 | 21.89 | 47.48 | 43.07 | 262.1 |
| Example | 140 | AZD0156 | | | | |
| $IC_{50}$ (nm) | 213.4 | 10.04 | | | | |

Therefore, by MTT assay, N,N-dimethyl-3-(4-(1-((3S,5R)-3,4,5-trimethylpiperazin-1-yl)-[1,2,4]triazolo[4,3-a]quinoxalin-8-yl)phenoxy)propan-1-amine (Example 23) and its analogues inhibited the growth of SW620 cell. In several example, such as Example 57, the inhibitory effect on the growth of SW620 cells was comparable to AZD0156.

Example 154

Inhibitory Effects of N,N-dimethyl-3-(4-(1-(tetrahydro-2H-pyran-4-yl)-[1,2,4]triazolo[4,3-a]quinoxalin-8-yl)phenoxy)propan-1-amine and its Analogues on the Growth of Human Breast Cancer Cell MDA-MB-468 were Determined by MTT Assay The revived MDA-MB-468 cells were cultured and passaged until they grew well and had a confluence about 90%. MDA-MB-468 cells were digested by trypsinase, centrifuged at 800 rpm for 5 minutes, the supernatant was discarded, resuspended with fresh medium (RPMI 1640 medium+10% FBS) and counted. The cells were seeded into 96-well cell culture plate with appropriate cell density and incubated overnight in a 37° C. 5% $CO_2$ incubator. The stock solutions of the tested compound and the reference compound AZD0156 were serially diluted to 8 concentrations by DMSO at the ratios of 1:3 and 1:10, respectively: the first concentration was 100 μM or 1 μM, and the last concentration was negative control of DMSO (0 μM, the final concentration of DMSO was 1%). 5 μL of each concentration was added to 120 μL of medium (25 times diluted) and mixed by shaking. The overnight cells were taken and the culture medium was removed, 195 μL of fresh medium was added to each well, and 5 μL of diluted medium containing the corresponding concentration of the tested sample was added respectively, and the culture plate was then placed in the 5% $CO_2$ cell culture incubator at 37° C. for 7 days (On the fourth day, the medium containing drugs was removed and fresh medium containing drugs was added for continuous cultivation). After removing the original solution, 100 μL of fresh serum-free DMEM medium containing MTT (0.5 mg/mL) was added to each well, the culture was continued. After 4 hours, the original solution was removed, 100 μL of DMSO was added into each well, the 96-well plates were shaken away from light for 10 minutes and placed in a multi-function reader to read the absorbance at the wavelength of 552/630/690 nm. GraphPad Prism 6.0 was used to analyze the data. The inhibitory activity of compounds on cell proliferation was plotted based on cell viability and compound concentration. The $IC_{50}$ value was fitted by a sigmoidal dose response curve equation $Y=100/(1+10^{\wedge}(Log\ C - Log\ IC_{50}))$, where C was the concentration of compound.

Table 4 summarizes the inhibitory effects of compounds on the growth of human breast cancer cell MDA-MB-468 ($IC_{50}$).

TABLE 4

Inhibitory effects of N,N-dimethyl-3-(4-(1-(tetrahydro-2H-pyran-4-yl)-[1,2,4]triazolo[4,3-a]quinoxalin-8-yl)phenoxy)propan-1-amine and its analogues on the growth of human breast cancer cell MDA-MB-468

| Example | 3 | 4 | 5 | 11 | 12 | 18 |
|---|---|---|---|---|---|---|
| $IC_{50}$ (nm) | 1865 | 950.4 | >$10^5$ | >$10^5$ | 236.1 | >$10^5$ |
| Example | 20 | 21 | 22 | 23 | 27 | 29 |
| $IC_{50}$ (nm) | 122.2 | 372.1 | 422.4 | 54.12 | 452.1 | 860.2 |
| Example | 30 | 31 | 37 | 44 | 45 | 46 |
| $IC_{50}$ (nm) | >10 μM | 334.8 | 4709 | 183.3 | 106.2 | 929.6 |
| Example | 47 | 48 | 49 | 50 | 51 | 52 |
| $IC_{50}$ (nm) | 145.2 | 160.8 | 1578 | >$10^5$ | 3679 | 523.0 |
| Example | 53 | 54 | 57 | 58 | 59 | 64 |
| $IC_{50}$ (nm) | >$10^5$ | >$10^5$ | 14.96 | 68.81 | 6.61 | >$10^4$ |

TABLE 4-continued

Inhibitory effects of N,N-dimethyl-3-(4-(1-(tetrahydro-2H-pyran-4-yl)-[1,2,4]triazolo[4,3-a]quinoxalin-8-yl)phenoxy)propan-1-amine and its analogues on the growth of human breast cancer cell MDA-MB-468

| Example | 66 | 67 | 68 | 69 | 70 | 71 |
|---|---|---|---|---|---|---|
| $IC_{50}$ (nm) | 429.9 | >$10^5$ | >$10^5$ | >$10^4$ | >$10^5$ | >$10^5$ |
| Example | 72 | 73 | 74 | 75 | 76 | 77 |
| $IC_{50}$ (nm) | 103.5 | 209.6 | 304.7 | 167.6 | 262.3 | 937.4 |
| Example | 80 | 81 | 82 | 83 | 84 | 85 |
| $IC_{50}$ (nm) | 270.6 | 201.4 | 200.5 | 73.36 | 245.8 | 22.16 |
| Example | 90 | AZD0156 | | | | |
| $IC_{50}$ (nm) | >$10^4$ | 10.93 | | | | |

Therefore, by MTT assay, N,N-dimethyl-3-(4-(1-((3S,5R)-3,4,5-trimethylpiperazin-1-yl)-[1,2,4]triazolo[4,3-a]quinoxalin-8-yl)phenoxy)propan-1-amine (Example 23) and its analogues inhibited the growth of MDA-MB-468 cell. In several example, such as Example 57, the inhibitory effect on the growth of MDA-MB-468 cells was comparable to AZD0156.

Having now fully described this disclosure, it will be understood by those of ordinary skill in the art that the same can be performed within a wide and equivalent range of conditions, formulations and other parameters without affecting the scope of the disclosure or any embodiment thereof. All patents, patent applications and publications cited herein are fully incorporated by reference herein in their entirety.

What is claimed is:

1. A compound having the Formula I:

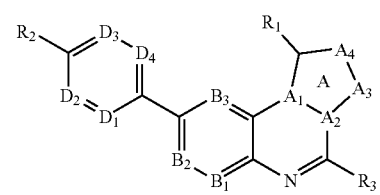

or a pharmaceutically acceptable salt or prodrug thereof, wherein:
$A_1$ is N;
$A_2$ is C;
$A_3$ and $A_4$ each are independently N, O, S, or CR';
A ring including $A_1$-$A_4$ is an optionally substituted 5-member heteroaryl containing 1-3 heteroatoms;
$B_1$ is CR", wherein R" is hydrogen, halo, optionally substituted amino, optionally substituted $C_{1-10}$ alkyl, alkenyl, alkynyl, nitro, cyano, acylamido, hydroxy, thiol, acyloxy, azido, carboxy, ethylenedioxo, hydroxyacylamido, or optionally substituted alkylthiol;
$B_2$ and $B_3$ each are independently CR", wherein R" is hydrogen, halo, optionally substituted amino, optionally substituted alkoxy, optionally substituted $C_{1-10}$ alkyl, alkenyl, alkynyl, nitro, cyano, acylamido, hydroxy, thiol, acyloxy, azido, carboxy, ethylenedioxo, hydroxyacylamido, or optionally substituted alkylthiol;
$D_1$-$D_4$ each are independently N or CR'";
$R_1$ is optionally substituted $C_{2-6}$ alkyl, optionally substituted alkoxy, optionally substituted amino, optionally substituted carbocyclic group, optionally substituted heterocyclic group, optionally substituted aryl or optionally substituted heteroaryl;

R$_2$ is hydrogen, substituted alkoxy, substituted amino, optionally substituted carbocyclic group, optionally substituted hetercyclic group, optionally substituted aryl or optionally substituted heteroaryl;

R', R''' and R$_3$ each are independently hydrogen, halo, optionally substituted amino, optionally substituted alkoxy, optionally substituted C$_{1-10}$ alkyl, alkenyl, alkynyl, nitro, cyano, acylamido, hydroxy, thiol, acyloxy, azido, carboxy, ethylenedioxo, hydroxyacylamido or optionally substituted alkylthiol.

2. The compound of claim 1, wherein the A ring including A$_1$-A$_4$, the 6-member ring including A$_1$-A$_2$, and the ring including B$_1$-B$_3$ are fused to form [1,2,4]triazolo[4,3-a]quinoxalinyl, imidazo[1,5-a]quinoxalinyl, imidazo[1,2-a]quinoxalinyl, or pyrrolo[1,2-a]quinoxalinyl; and/or R$_1$ is an optionally substituted C$_{2-6}$ alkyl group, heterocyclic group, aryl group or heteroaryl group, wherein the substituent on the alkyl group is selected from the group consisting of tetrahydrofuryl, tetrahydropyranyl, pyranyl, piperidyl, piperazinyl, pyrrolidinyl, imidazolidinyl, imidazolinyl, dihydroindolyl, dihydroisoindolyl, morpholinyl, pyrazolidinyl and pyrazolinyl; the substituents on the heterocyclic group, aryl group and heteroaryl group is selected from the group consisting of C$_{1-6}$ alkyl and —NR$_9$R$_{10}$ groups and the number of the substituents is 1 to 4, wherein R$_9$ and R$_{10}$ are independently selected from hydrogen or C$_{1-6}$ alkyl groups; and/or the ring comprising D$_1$-D$_4$ is optionally substituted pyridinyl, optionally substituted phenyl, optionally substituted pyrimidinyl, or optionally substituted pyrazinyl; and/or R$_2$ is selected from the group consisting of hydrogen, amino substituted with one or two C$_{1-6}$ alkyl, C$_{1-6}$ alkyl optionally substituted with —NR$_9$R$_{10}$, C$_{1-6}$ alkoxy optionally substituted with —NR$_9$R$_{10}$, C$_{1-6}$ alkyl-NH- optionally substituted with —NR$_9$R$_{10}$, piperazinyl optionally substituted with 1-3 C$_{1-4}$ alkyl groups, piperidyl optionally substituted with —NR$_9$R$_{10}$ or —NR$_9$R$_{10}$-substituted C$_{1-6}$ alkyl, and C$_{3-8}$ cycloalkyl optionally substituted with —NR$_9$R$_{10}$, wherein R$_9$ and R$_{10}$ are independently selected from hydrogen or C$_{1-6}$ alkyl groups; and/or R$_3$ is H.

3. The compound of claim 1, wherein the compound has Formula II:

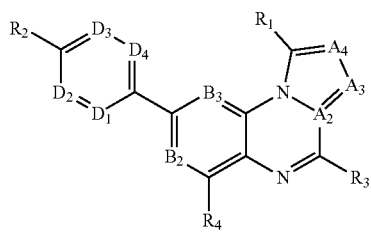

II or pharmaceutically acceptable salts or prodrugs thereof, wherein:

A$_2$-A$_4$, B$_2$-B$_3$, D$_1$-D$_4$ and R$_1$-R$_3$ are defined as in claim 1;

R$_4$ is independently H, halo, optionally substituted amino, optionally substituted C$_{1-10}$ alkyl, alkenyl, alkynyl, nitro, cyano, acylamido, hydroxy, thiol, acyloxy, azido, carboxy, ethylenedioxo, hydroxyacylamido or optionally substituted alkylthiol.

4. The compound of claim 3, wherein:

the ring including A$_2$-A$_4$, the 6-member ring including A$_2$, and the ring including B$_2$-B$_3$ are fused to form [1,2,4]triazolo[4,3-a]quinoxalinyl, imidazo[1,5-a]quinoxalinyl, imidazo[1,2-a]quinoxalinyl or pyrrolo[1,2-a]quinoxalinyl; and/or R$_1$ is selected from the group consisting of tetrahydropyranyl that is not substituted or optionally substituted with 1-4 C$_{1-6}$ alkyl groups, piperidyl that is not substituted or optionally substituted with —NR$_9$R$_{10}$ or 1-4 C$_{1-6}$ alkyl groups, morpholinyl that is not substituted or optionally substituted with 1-4 C$_{1-6}$ alkyl groups, imidazolyl, piperazinyl that is optionally substituted with 1-4 C$_{1-6}$ alkyl groups, C$_{1-6}$ alkyl that is optionally substituted with a heterocyclic group; wherein R$_9$ and R$_{10}$ are independently selected from hydrogen and C$_{1-6}$ alkyl groups; and/or the ring including D$_1$-D$_4$ is an optionally substituted pyridyl ring, an optionally substituted phenyl ring, an optionally substituted pyrimidinyl ring, or an optionally substituted pyrazinyl ring;

and/or

R$_2$ is selected from the group consisting of hydrogen, amino substituted with one or two C$_{1-6}$ alkyl, C$_{1-6}$ alkyl optionally substituted with R$_{10}$, C$_{1-6}$ alkoxy optionally substituted with —NR$_9$R$_{10}$, C$_{1-6}$ alkyl-NH— optionally substituted with —NR$_9$R$_{10}$, piperazinyl optionally substituted with 1-3 C$_{1-4}$ alkyl groups, piperidyl optionally substituted with —NR$_9$R$_{10}$, and C$_{3-8}$ cycloalkyl optionally substituted with —NR$_9$R$_{10}$, wherein R$_9$ and R$_{10}$ are independently selected from the group consisting of hydrogen and C$_{1-6}$ alkyl; and/or R$_3$ and R$_4$ are H.

5. The compound of claim 3, wherein the compound has Formula IIIa or IIIb:

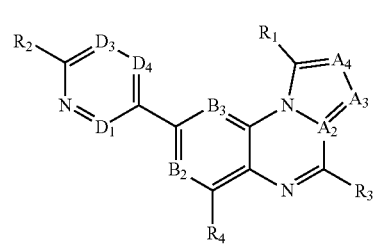

IIIa

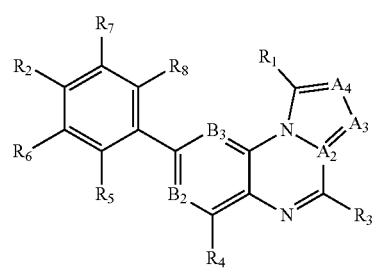

IIIb or pharmaceutically acceptable salts or prodrugs thereof, wherein:

in Formula IIIb, R$_5$-R$_6$ are independently H, halo, optionally substituted amino, optionally substituted alkoxy, optionally substituted C$_{1-10}$ alkyl, alkenyl, alkynyl, nitro, cyano, acylamido, hydroxy, thiol, acyloxy, azido, carboxy, ethylenedioxo, hydroxyacylamido, or optionally substituted alkylthiol.

6. The compound of claim 5, wherein in Formula IIIb, $A_2$ is C;
$A_3$ and $A_4$ are N; $B_2$ is CH; $B_3$ is CH; $R_6$ is haloalkyl or halo; $R_5$, $R_7$ and $R_8$ are H or halo; $R_1$ is optionally substituted heterocyclic group; $R_2$ is optionally substituted heterocyclic group, or $C_{1-10}$ alkoxy substituted by —$NR_9R_{10}$; wherein, $R_9$ and $R_{10}$ independently are H or C1-6 alkyl.

7. The compound of claim 6, wherein in Formula IIIb, $B_3$ is CH; $R_6$ is $CF_3$, F, Cl or Br; $R_5$, $R_7$ and $R_8$ are H or halo; and $R_2$ is optionally substituted heterocyclic group, or $C_{1-6}$ alkoxy substituted by —$NR_9R_{10}$.

8. The compound of claim 5, wherein:
the ring including $A_2$-$A_4$, the 6-member ring including $A_2$, and the ring including $B_2$-$B_3$ are fused to form [1,2,4]triazolo[4,3-a]quinoxalinyl, imidazo[1,5-a]quinoxalinyl, imidazo[1,2-a]quinoxalinyl or pyrrolo[1,2-a]quinoxalinyl; and/or
$R_1$ is selected from the group consisting of tetrahydropyranyl that is not substituted or optionally substituted with 1-4 $C_{1-6}$ alkyl groups, piperidyl that is not substituted or optionally substituted with —$NR_9R_{10}$ or 1-4 $C_{1-6}$ alkyl groups, morpholinyl that is not substituted or optionally substituted with 1-4 $C_{1-6}$ alkyl groups, imidazolyl, piperazinyl that is optionally substituted with 1-4 $C_{1-6}$ alkyl groups, and $C_{1-6}$ alkyl that is optionally substituted with a heterocyclic group; wherein $R_9$ and $R_{10}$ are independently selected from hydrogen and $C_{1-6}$ alkyl groups; and/or
the ring including $D_1$-$D_4$ is an optionally substituted pyridyl ring, an optionally substituted phenyl ring, an optionally substituted pyrimidinyl ring, or an optionally substituted pyrazinyl ring;
and/or
$R_2$ is selected from the group consisting of hydrogen, amino substituted with one or two $C_{1-6}$ alkyl, $C_{1-6}$ alkyl optionally substituted with —$NR_9R_{10}$, $C_{1-6}$ alkoxy optionally substituted with —$NR_9R_{10}$, $C_{1-6}$ alkyl-NH—optionally substituted with —$NR_9R_{10}$, $C_{1-6}$ alkyl-$NHR_9$—optionally substituted with —$NR_9R_{10}$, piperazinyl optionally substituted with 1-3 $C_{1-4}$ alkyl groups, piperidyl optionally substituted with —$NR_9R_{10}$, and $C_{3-8}$ cycloalkyl optionally substituted with —$NR_9R_{10}$, wherein $R_9$ and $R_{10}$ are independently selected from the group consisting of hydrogen and $C_{1-6}$ alkyl;
$R_3$ and $R_4$ are H; and/or
$R_5$ to $R_8$ are independently H, halo, $C_{1-4}$ alkyl, or halo $C_{1-4}$ alkyl.

9. The compound of claim 5, wherein
$R_1$ is selected from the group consisting of:

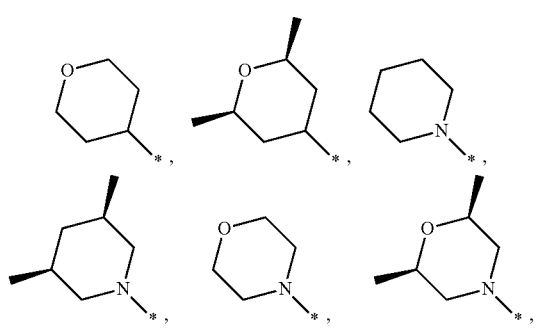

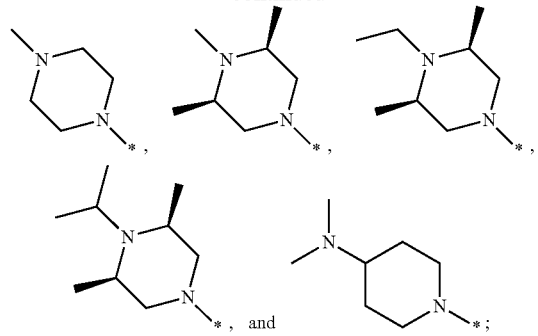

$R_2$ is selected from the group consisting of:

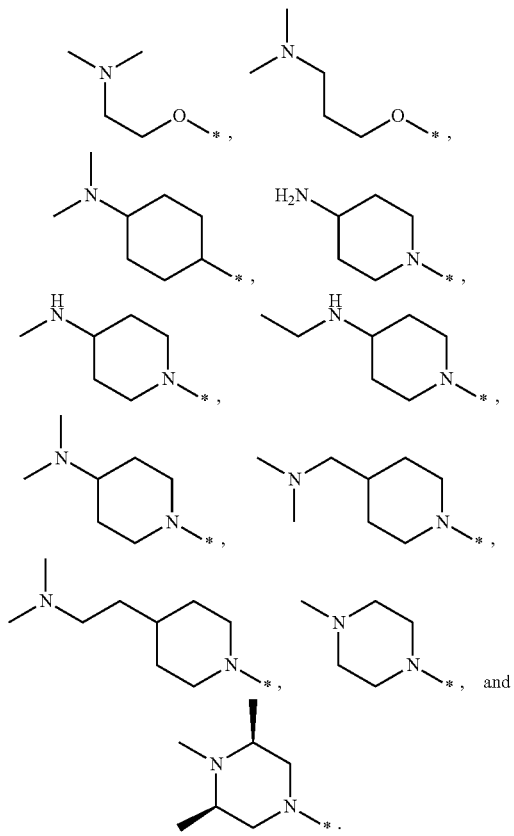

10. The compound of claim 1, wherein said compound is selected from the group consisting of:
N,N-dimethyl-3-((5-(1-(tetrahydro-2H-pyran-4-yl)-[1,2,4]triazolo[4,3-a]quinoxalin-8-yl)pyridin-2-yl)oxy)propan-1-amine;
N,N-dimethyl-3-(4-(1-(tetrahydro-2H-pyran-4-yl)-[1,2,4]triazolo[4,3-a]quinoxalin-8-yl)phenoxy)propan-1-amine;
N,N-dimethyl-3-((6-(1-(tetrahydro-2H-pyran-4-yl)-[1,2,4]triazolo[4,3-a]quinoxalin-8-yl)pyridin-3-yl)oxy)propan-1-amine;
N,N-dimethyl-3-((5-(1-(tetrahydro-2H-pyran-4-yl)-[1,2,4]triazolo[4,3-a]quinoxalin-8-yl)pyrimidin-2-yl)oxy)propan-1-amine;
N,N-dimethyl-3-((2-(1-(tetrahydro-2H-pyran-4-yl)-[1,2,4]triazolo[4,3-a]quinoxalin-8-yl)pyrimidin-5-yl)oxy)propan-1-amine;

N,N-dimethyl-3-((5-(1-(tetrahydro-2H-pyran-4-yl)-[1,2,4]triazolo[4,3-a]quinoxalin-8-yl)pyrazin-2-yl)oxy)propan-1-amine;
N,N-dimethyl-2-(4-(1-(tetrahydro-2H-pyran-4-yl)-[1,2,4]triazolo[4,3-a]quinoxalin-8-yl)phenoxy)ethan-1-amine;
N-(3-(dimethylamino)propyl)-4-(1-(tetrahydro-2H-pyran-4-yl)-[1,2,4]triazolo[4,3-a]quinoxalin-8-yl)aniline;
N-(3-(dimethylamino)propyl)-N-methyl-4-(1-(tetrahydro-2H-pyran-4-yl)-[1,2,4]triazolo[4,3-a]quinoxalin-8-yl)aniline;
N,N-dimethyl-1-(4-(1-(tetrahydro-2H-pyran-4-yl)-[1,2,4]triazolo[4,3-a]quinoxalin-8-yl)phenyl)piperidin-4-amine;
8-(4-(4-methylpiperazin-1-yl)phenyl)-1-(tetrahydro-2H-pyran-4-yl)-[1,2,4]triazolo[4,3-a]quinoxaline;
1-(tetrahydro-2H-pyran-4-yl)-8-(4-((3S,5R)-3,4,5-trimethylpiperazin-1-yl)phenyl)-[1,2,4]triazolo[4,3-a]quinoxaline;
N,N-dimethyl-1-(5-(1-(tetrahydro-2H-pyran-4-yl)-[1,2,4]triazolo[4,3-a]quinoxalin-8-yl)pyridin-2-yl)piperidin-4-amine;
8-(6-(4-methylpiperazin-1-yl)pyridin-3-yl)-1-(tetrahydro-2H-pyran-4-yl)[1,2,4]triazolo[4,3-a]quinoxaline;
1-(tetrahydro-2H-pyran-4-yl)-8-(6-((3S,5R)-3,4,5-trimethylpiperazin-1-yl)pyridin-3-yl)-[1,2,4]triazolo[4,3-a]quinoxaline;
N,N-dimethyl-4-(4-(1-(tetrahydro-2H-pyran-4-yl)-[1,2,4]triazolo[4,3-a]quinoxalin-8-yl)phenyl)cyclohexan-1-amine;
N,N-dimethyl-4-(5-(1-(tetrahydro-2H-pyran-4-yl)-[1,2,4]triazolo[4,3-a]quinoxalin-8-yl)pyridin-2-yl)cyclohexan-1-amine;
N,N-dimethyl-3-(4-(1-(piperidin-1-yl)-[1,2,4]triazolo[4,3-a]quinoxalin-8-yl)phenoxy)propan-1-amine;
N,N-dimethyl-3-(4-(1-morpholino-[1,2,4]triazolo[4,3-a]quinoxalin-8-yl)phenoxy)propan-1-amine;
N,N-dimethyl-3-(4-(1-(4-methylpiperazin-1-yl)-[1,2,4]triazolo[4,3-a]quinoxalin-8-yl)phenoxy)propan-1-amine;
N,N-dimethyl-3-(4-(1-((3S,5R)-3,4,5-trimethylpiperazin-1-yl)-[1,2,4]triazolo[4,3-a]quinoxalin-8-yl)phenoxy)propan-1-amine;
N,N-dimethyl-3-((5-(1-morpholino-[1,2,4]triazolo[4,3-a]quinoxalin-8-yl)pyridin-2-yl)oxy)propan-1-amine;
N,N-dimethyl-3-((5-(1-(4-methylpiperazin-1-yl)-[1,2,4]triazolo[4,3-a]quinoxalin-8-yl)pyridin-2-yl)oxy)propan-1-amine;
N,N-dimethyl-3-((5-(1-((3S,5R)-3,4,5-trimethylpiperazin-1-yl)-[1,2,4]triazolo[4,3-a]quinoxalin-8-yl)pyridin-2-yl)oxy)propan-1-amine;
N,N-dimethyl-3-(4-(1-(morpholinomethyl)-[1,2,4]triazolo[4,3-a]quinoxalin-8-yl)phenoxy)propan-1-amine;
3-(4-(1-(1H-imidazol-1-yl)-[1,2,4]triazolo[4,3-a]quinoxalin-8-yl)phenoxy)-N,N-dimethylpropan-1-amine;
3-(4-(1-(1H-imidazol-4-yl)-[1,2,4]triazolo[4,3-a]quinoxalin-8-yl)phenoxy)-N,N-dimethylpropan-1-amine;
N,N-dimethyl-3-(4-(1-(tetrahydro-2H-pyran-4-yl)imidazo[1,2-a]quinoxalin-8-yl)phenoxy)propan-1-amine;
N,N-dimethyl-3-(4-(1-(tetrahydro-2H-pyran-4-yl)imidazo[1,5-a]quinoxalin-8-yl)phenoxy)propan-1-amine;
N,N-dimethyl-3-(4-(1-(tetrahydro-2H-pyran-4-yl)H-pyrrolo[1,2-a]quinoxalin-8-yl)phenoxy)propan-1-amine;
8-phenyl-1-(tetrahydro-2H-pyran-4-yl)[1,2,4]triazolo[4,3-a]quinoxaline;
N,N,N-trimethyl-3-((4-(1-(tetrahydro-2H-pyran-4-yl)-[1,2,4]triazolo[4,3-a]quinoxalin-8-yl)phenyl)amino)propan-1-aminium;
1-(4-(1-(tetrahydro-2H-pyran-4-yl)-[1,2,4]triazolo[4,3-a]quinoxalin-8-yl)phenyl)piperidin-4-amine;
N-methyl-1-(4-(1-(tetrahydro-2H-pyran-4-yl)-[1,2,4]triazolo[4,3-a]quinoxalin-8-yl)phenyl)piperidin-4-amine;
N-ethyl-1-(4-(1-(tetrahydro-2H-pyran-4-yl)-[1,2,4]triazolo[4,3-a]quinoxalin-8-yl)phenyl)piperidin-4-amine;
1-(2-fluoro-4-(1-(tetrahydro-2H-pyran-4-yl)-[1,2,4]triazolo[4,3-a]quinoxalin-8-yl)phenyl)-N,N-dimethylpiperidin-4-amine;
1-(2-chloro-4-(1-(tetrahydro-2H-pyran-4-yl)-[1,2,4]triazolo[4,3-a]quinoxalin-8-yl)phenyl)-N,N-dimethylpiperidin-4-amine;
N,N-dimethyl-1-(2-methyl-4-(1-(tetrahydro-2H-pyran-4-yl)-[1,2,4]triazolo[4,3-a]quinoxalin-8-yl)phenyl)piperidin-4-amine;
N,N-dimethyl-1-(4-(1-(tetrahydro-2H-pyran-4-yl)-[1,2,4]triazolo[4,3-a]quinoxalin-8-yl)-2-(trifluoromethyl)phenyl)piperidin-4-amine;
1-(3-fluoro-4-(1-(tetrahydro-2H-pyran-4-yl)[1,2,4]triazolo[4,3-a]quinoxalin-8-yl)phenyl)-N,N-dimethylpiperidin-4-amine;
1-(3-chloro-4-(1-(tetrahydro-2H-pyran-4-yl)-[1,2,4]triazolo[4,3-a]quinoxalin-8-yl)phenyl)-N,N-dimethylpiperidin-4-amine;
N,N-dimethyl-1-(3-methyl-4-(1-(tetrahydro-2H-pyran-4-yl)-[1,2,4]triazolo[4,3-a]quinoxalin-8-yl)phenyl)piperidin-4-amine;
N,N-dimethyl-1-(4-(1-(tetrahydro-2H-pyran-4-yl)-[1,2,4]triazolo[4,3-a]quinoxalin-8-yl)-3-(trifluoromethyl)phenyl)piperidin-4-amine;
N,N-dimethyl-1-(6-(1-(tetrahydro-2H-pyran-4-yl)-[1,2,4]triazolo[4,3-a]quinoxalin-8-yl)pyridin-3-yl)piperidin-4-amine;
N,N-dimethyl-1-(1-(4-(1-(tetrahydro-2H-pyran-4-yl)-[1,2,4]triazolo[4,3-a]quinoxalin-8-yl)phenyl)piperidin-4-yl)methanamine;
N,N-dimethyl-2-(1-(4-(1-(tetrahydro-2H-pyran-4-yl)-[1,2,4]triazolo[4,3-a]quinoxalin-8-yl)phenyl)piperidin-4-yl)ethan-1-amine;
3-(2-fluoro-4-(1-((3S,5R)-3,4,5-trimethylpiperazin-1-yl)-[1,2,4]triazolo[4,3-a]quinoxalin-8-yl)phenoxy)-N,N-dimethylpropan-1-amine;
3-(2-chloro-4-(1-((3S,5R)-3,4,5-trimethylpiperazin-1-yl)-[1,2,4]triazolo[4,3-a]quinoxalin-8-yl)phenoxy)-N,N-dimethylpropan-1-amine;
N,N-dimethyl-3-(2-(trifluoromethyl)-4-(1-((3S,5R)-3,4,5-trimethylpiperazin-1-yl)-[1,2,4]triazolo[4,3-a]quinoxalin-8-yl)phenoxy)propan-1-amine;
N,N-dimethyl-1-(4-(1-((3S,5R)-3,4,5-trimethylpiperazin-1-yl)-[1,2,4]triazolo[4,3-a]quinoxalin-8-yl)phenyl)piperidin-4-amine;
1-(2-fluoro-4-(1-((3S,5R)-3,4,5-trimethylpiperazin-1-yl)-[1,2,4]triazolo[4,3-a]quinoxalin-8-yl)phenyl)-N,N-dimethylpiperidin-4-amine;
1-(2-chloro-4-(1-((3S,5R)-3,4,5-trimethylpiperazin-1-yl)-[1,2,4]triazolo[4,3-a]quinoxalin-8-yl)phenyl)-N,N-dimethylpiperidin-4-amine;
N,N-dimethyl-1-(2-(trifluoromethyl)-4-(1-((3S,5R)-3,4,5-trimethylpiperazin-1-yl)-[1,2,4]triazolo[4,3-a]quinoxalin-8-yl)phenyl)piperidin-4-amine;
1-(2-fluoro-6-(trifluoromethyl)-4-(1-((3S,5R)-3,4,5-trimethylpiperazin-1-yl)-[1,2,4]triazolo[4,3-a]quinoxalin-8-yl)phenyl)-N,N-dimethylpiperidin-4-amine;

1-(2-chloro-6-(trifluoromethyl)-4-(1-((3S,5R)-3,4,5-trimethylpiperazin-1-yl)-[1,2,4]triazolo[4,3-a]quinoxalin-8-yl)phenyl)-N,N-dimethylpiperidin-4-amine;
1-(4-(1-(4-(dimethylamino)piperidin-1-yl)-[1,2,4]triazolo[4,3-a]quinoxalin-8-yl)phenyl)-N,N-dimethylpiperidin-4-amine;
N,N-dimethyl-1-(4-(1-(morpholinomethyl)-[1,2,4]triazolo[4,3-a]quinoxalin-8-yl)phenyl)piperidin-4-amine;
N-methyl-1-(4-(1-(morpholinomethyl)-[1,2,4]triazolo[4,3-a]quinoxalin-8-yl)phenyl)piperidin-4-amine;
1-(2-fluoro-4-(1-((3S,5R)-3,4,5-trimethylpiperazin-1-yl)-[1,2,4]triazolo[4,3-a]quinoxalin-8-yl)phenyl)-N-methylpiperidin-4-amine;
N-methyl-1-(2-(trifluoromethyl)-4-(1-((3S,5R)-3,4,5-trimethylpiperazin-1-yl)-[1,2,4]triazolo[4,3-a]quinoxalin-8-yl)phenyl)piperidin-4-amine;
N-ethyl-1-(2-fluoro-4-(1-((3S,5R)-3,4,5-trimethylpiperazin-1-yl)-[1,2,4]triazolo[4,3-a]quinoxalin-8-yl)phenyl)piperidin-4-amine;
N-ethyl-1-(2-(trifluoromethyl)-4-(1-((3S,5R)-3,4,5-trimethylpiperazin-1-yl)-[1,2,4]triazolo[4,3-a]quinoxalin-8-yl)phenyl)piperidin-4-amine;
1-(4-(1-((3S,5R)-4-ethyl-3,5-dimethylpiperazin-1-yl)-[1,2,4]triazolo[4,3-a]quinoxalin-8-yl)-2-(trifluoromethyl)phenyl)-N,N-dimethylpiperidin-4-amine;
1-(4-(1-((3S,5R)-4-isopropyl-3,5-dimethylpiperazin-1-yl)-[1,2,4]triazolo[4,3-a]quinoxalin-8-yl)-2-(trifluoromethyl)phenyl)-N,N-dimethylpiperidin-4-amine;
3-(4-(1-((2S,6R)-2,6-dimethylmorpholino)-[1,2,4]triazolo[4,3-a]quinoxalin-8-yl)-2-fluorophenoxy)-N,N-dimethylpropan-1-amine;
3-(2-chloro-4-(1-((2S,6R)-2,6-dimethylmorpholino)-[1,2,4]triazolo[4,3-a]quinoxalin-8-yl)phenoxy)-N,N-dimethylpropan-1-amine;
3-(4-(1-((2S,6R)-2,6-dimethylmorpholino)-[1,2,4]triazolo[4,3-a]quinoxalin-8-yl)-2-(trifluoromethyl)phenoxy)-N, N-dimethylpropan-1-amine;
1-(4-(1-((2S,6R)-2,6-dimethylmorpholino)-[1,2,4]triazolo[4,3-a]quinoxalin-8-yl)phenyl)-N,N-dimethylpiperidin-4-amine;
1-(4-(1-((2S,6R)-2,6-dimethylmorpholino)-[1,2,4]triazolo[4,3-a]quinoxalin-8-yl)-2-fluorophenyl)-N,N-dimethylpiperidin-4-amine;
1-(2-chloro-4-(1-((2S,6R)-2,6-dimethylmorpholino)-[1,2,4]triazolo[4,3-a]quinoxalin-8-yl)phenyl)-N,N-dimethylpiperidin-4-amine;
1-(4-(1-((2S,6R)-2,6-dimethylmorpholino)-[1,2,4]triazolo[4,3-a]quinoxalin-8-yl)-2-(trifluoromethyl)phenyl)-N,N-dimethylpiperidin-4-amine;
1-(4-(1-((2S,6R)-2,6-dimethylmorpholino)-[1,2,4]triazolo[4,3-a]quinoxalin-8-yl)-2-(trifluoromethyl)phenyl)-N-methylpiperidin-4-amine;
1-(4-(1-((2S,6R)-2,6-dimethylmorpholino)-[1,2,4]triazolo[4,3-a]quinoxalin-8-yl)-2-(trifluoromethyl)phenyl)-N-ethylpiperidin-4-amine;
3-(4-(1-((2R,6S)-2,6-dimethyltetrahydro-2H-pyran-4-yl)-[1,2,4]triazolo[4,3-a]quinoxalin-8-yl)-2-(trifluoromethyl)phenoxy)-N,N-dimethylpropan-1-amine;
1-(4-(1-((2R,6S)-2,6-dimethyltetrahydro-2H-pyran-4-yl)-[1,2,4]triazolo[4,3-a]quinoxalin-8-yl)-2-(trifluoromethyl)phenyl)-N,N-dimethylpiperidin-4-amine;
N,N-dimethyl-3-(4-(1-(piperidin-1-yl)-[1,2,4]triazolo[4,3-a]quinoxalin-8-yl)-2-(trifluoromethyl)phenoxy)propan-1-amine;
1-(2-fluoro-4-(1-(piperidin-1-yl)-[1,2,4]triazolo[4,3-a]quinoxalin-8-yl)phenyl)-N,N-dimethylpiperidin-4-amine;
1-(2-chloro-4-(1-(piperidin-1-yl)-[1,2,4]triazolo[4,3-a]quinoxalin-8-yl)phenyl)-N,N-dimethylpiperidin-4-amine;
N,N-dimethyl-1-(4-(1-(piperidin-1-yl)-[1,2,4]triazolo[4,3-a]quinoxalin-8-yl)-2-(trifluoromethyl)phenyl)piperidin-4-amine;
3-(4-(1-((3R,5S)-3,5-dimethylpiperidin-1-yl)-[1,2,4]triazolo[4,3-a]quinoxalin-8-yl)-2-(trifluoromethyl)phenoxy)-N,N-dimethylpropan-1-amine;
1-(4-(1-((3R,5S)-3,5-dimethylpiperidin-1-yl)-[1,2,4]triazolo[4,3-a]quinoxalin-8-yl)-2-(trifluoromethyl)phenyl)-N,N-dimethylpiperidin-4-amine;
3-(2-bromo-4-(1-((3S,5R)-3,4,5-trimethylpiperazin-1-yl)-[1,2,4]triazolo[4,3-a]quinoxalin-8-yl)phenoxy)-N,N-dimethylpropan-1-amine;
3-(3-fluoro-4-(1-((3S,5R)-3,4,5-trimethylpiperazin-1-yl)-[1,2,4]triazolo[4,3-a]quinoxalin-8-yl)phenoxy)-N,N-dimethylpropan-1-amine;
3-(2-fluoro-6-(trifluoromethyl)-4-(1-((3S,5R)-3,4,5-trimethylpiperazin-1-yl)-[1,2,4]triazolo[4,3-a]quinoxalin-8-yl)phenoxy)-N,N-dimethylpropan-1-amine;
3-(2-chloro-6-(trifluoromethyl)-4-(1-((3S,5R)-3,4,5-trimethylpiperazin-1-yl)-[1,2,4]triazolo[4,3-a]quinoxalin-8-yl)phenoxy)-N,N-dimethylpropan-1-amine;
3-(2-chloro-3-fluoro-4-(1-((3S,5R)-3,4,5-trimethylpiperazin-1-yl)-[1,2,4]triazolo[4,3-a]quinoxalin-8-yl)phenoxy)-N,N-dimethylpropan-1-amine;
1-(2-bromo-4-(1-((3S,5R)-3,4,5-trimethylpiperazin-1-yl)-[1,2,4]triazolo[4,3-a]quinoxalin-8-yl)phenyl)-N,N-dimethylpiperidin-4-amine;
and pharmaceutically acceptable salts or prodrugs thereof.

11. A method for treating a disease caused by DDR functional deficiencies or benefiting from the inhibition of kinase activity, comprising administering to a subject in need thereof an effective amount of the compound of claim 1 or a pharmaceutically acceptable salt or prodrug thereof or a pharmaceutical composition comprising the compound of claim 1 or a pharmaceutically acceptable salt or prodrug thereof, wherein the disease is a cancer selected from liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, choriocarcinoma, mycosis fungoide, head and neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, or prostatic carcinoma.

12. The method of claim 11, wherein the method further comprises administering to the subject at least one anticancer drug, or a pharmaceutically acceptable salt thereof.

13. The method of claim 12, wherein the at least one anticancer drug is selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, methylhydroxy ellipticine, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, mAb, panitumumab, ofatumumab, avastin, trastuzumab, rituximab, imatinib, gefitinib, erlotinib, lapatinib, sorafinib, sunitinib, nilotinib, dasatinib, pazopanib, bortezomib, torisel, everolimus, vorinostat, romidepsin, tamoxifen, letrozole, fulvestrant, mitoguazone, octreotide, retinoic acid, arsenic trioxide, zoledronic acid, bortezomib, thalidomide, lenalidomide, venetoclax, aldesleukin, sipueucel-T, palbociclib, olaparib, niraparib, rucaparib and talazoparib.

14. The method of claim 11, wherein the compound of claim 1 or a pharmaceutically acceptable salt or prodrug thereof or the pharmaceutical composition comprising the compound of claim 1 or a pharmaceutically acceptable salt or prodrug thereof is used in combination with radiotherapy.

15. The method of claim 11, wherein the compound has Formula IIIa or IIIb:

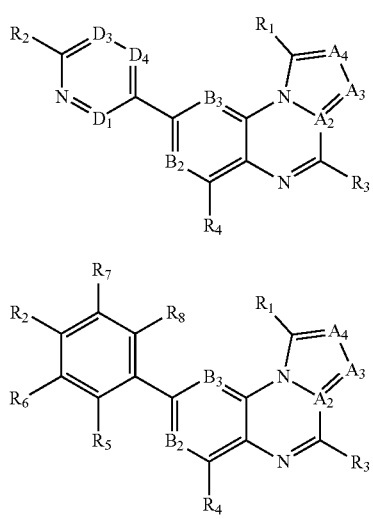

wherein:
  $A_2$ is CN;
  $A_3$ and $A_4$ each are independently N, O, S, or CR';
  A ring including $A_1$-$A_4$ is an optionally substituted 5-member heteroaryl containing 1-3 heteroatoms;
  $B_2$-$B_3$ each are independently CR";
  $D_1$, $D_3$ and $D_4$ each are independently N or CR'";
  $R_1$ is optionally substituted $C_{2-6}$ alkyl, optionally substituted alkoxy, optionally substituted amino, optionally substituted carbocyclic group, optionally substituted hetercyclic group, optionally substituted aryl or optionally substituted heteroaryl;
  $R_2$ is hydrogen, substituted alkoxy, substituted amino, optionally substituted carbocyclic group, optionally substituted hetercyclic group, optionally substituted aryl or optionally substituted heteroaryl;
  R', R", R'" and $R_3$ each are independently hydrogen, halo, optionally substituted amino, optionally substituted alkoxy, optionally substituted $C_{1-10}$ alkyl, alkenyl, alkynyl, nitro, cyano, acylamido, hydroxy, thiol, acyloxy, azido, carboxy, ethylenedioxo, hydroxyacylamido, or optionally substituted alkylthiol;
  $R_4$ is independently H, halo, optionally substituted amino, optionally substituted $C_{1-10}$ alkyl, alkenyl, alkynyl, nitro, cyano, acylamido, hydroxy, thiol, acyloxy, azido, carboxy, ethylenedioxo, hydroxyacylamido, or optionally substituted alkylthiol; and
  $R_5$-$R_6$ are independently H, halo, optionally substituted amino, optionally substituted alkoxy, optionally substituted $C_{1-10}$ alkyl, alkenyl, alkynyl, nitro, cyano, acylamido, hydroxy, thiol, acyloxy, azido, carboxy, ethylenedioxo, hydroxyacylamido, or optionally substituted alkylthiol.

16. A pharmaceutical composition comprising a compound of claim 1 or a pharmaceutically acceptable salt or prodrug thereof and a pharmaceutically acceptable carrier, and optionally at least one known anticancer drug, or a pharmaceutically acceptable salt thereof.

17. The pharmaceutical composition of claim 16, wherein the pharmaceutical composition further comprises at least one anticancer drug, or a pharmaceutically acceptable salt thereof; wherein the pharmaceutical composition further comprises at least one of the following anticancer drugs: busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, methylhydroxy ellipticine, etoposide, 5-azacytidine, gemcitabine, 5-fluorouracil, methotrexate, 5-fluoro-2'-deoxy-uridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, mAb, panitumumab, ofatumumab, avastin, trastuzumab, rituximab, imatinib, gefitinib, erlotinib, lapatinib, sorafinib, sunitinib, nilotinib, dasatinib, pazopanib, bortezomib, torisel, everolimus, vorinostat, romidepsin, tamoxifen, letrozole, fulvestrant, mitoguazone, octreotide, retinoic acid, arsenic trioxide, zoledronic acid, bortezomib, thalidomide, lenalidomide, venetoclax, aldesleukin, sipueucel-T, palbociclib, olaparib, niraparib, rucaparib and talazoparib.

18. The pharmaceutical composition of claim 16, wherein the compound has Formula IIIa or IIIb:

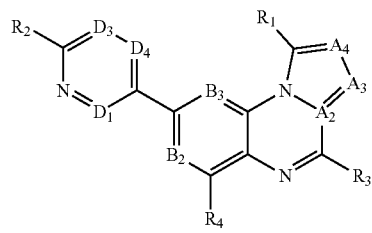

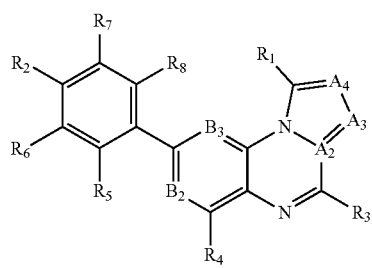

wherein:
- $A_2$ is C or N;
- $A_3$ and $A_4$ each are independently N, O, S, or CR';
- A ring including $A_1$-$A_4$ is an optionally substituted 5-member heteroaryl containing 1-3 heteroatoms;
- $B_2$-$B_3$ each are independently CR";
- $D_1$, $D_3$ and $D_4$ each are independently N or CR";
- $R_1$ is optionally substituted $C_{2-6}$ alkyl, optionally substituted alkoxy, optionally substituted amino, optionally substituted carbocyclic group, optionally substituted hetercyclic group, optionally substituted aryl or optionally substituted heteroaryl;
- $R_2$ is hydrogen, substituted alkoxy, substituted amino, optionally substituted carbocyclic group, optionally substituted hetercyclic group, optionally substituted aryl or optionally substituted heteroaryl;
- R', R", R'" and $R_3$ each are independently hydrogen, halo, optionally substituted amino, optionally substituted alkoxy, optionally substituted $C_{1-10}$ alkyl, alkenyl, alkynyl, nitro, cyano, acylamido, hydroxy, thiol, acyloxy, azido, carboxy, ethylenedioxo, hydroxyacylamido, or optionally substituted alkylthiol;
- $R_4$ is independently H, halo, optionally substituted amino, optionally substituted $C_{1-10}$ alkyl, alkenyl, alkynyl, nitro, cyano, acylamido, hydroxy, thiol, acyloxy, azido, carboxy, ethylenedioxo, hydroxyacylamido, or optionally substituted alkylthiol; and
- $R_5$-$R_8$ are independently H, halo, optionally substituted amino, optionally substituted alkoxy, optionally substituted $C_{1-10}$ alkyl, alkenyl, alkynyl, nitro, cyano, acylamido, hydroxy, thiol, acyloxy, azido, carboxy, ethylenedioxo, hydroxyacylamido, or optionally substituted alkylthiol.

19. The pharmaceutical composition of claim 16, wherein compound is selected from the group consisting of:
- N,N-dimethyl-3-((5-(1-(tetrahydro-2H-pyran-4-yl)-[1,2,4]triazolo[4,3-a]quinoxalin-8-yl)pyridin-2-yl)oxy)propan-1-amine;
- N,N-dimethyl-3-(4-(1-(tetrahydro-2H-pyran-4-yl)-[1,2,4]triazolo[4,3-a]quinoxalin-8-yl)phenoxy)propan-1-amine;
- N,N-dimethyl-3-((6-(1-(tetrahydro-2H-pyran-4-yl)-[1,2,4]triazolo[4,3-a]quinoxalin-8-yl)pyridin-3-yl)oxy)propan-1-amine;
- N,N-dimethyl-3-((5-(1-(tetrahydro-2H-pyran-4-yl)-[1,2,4]triazolo[4,3-a]quinoxalin-8-yl)pyrimidin-2-yl)oxy)propan-1-amine;
- N,N-dimethyl-3-((2-(1-(tetrahydro-2H-pyran-4-yl)-[1,2,4]triazolo[4,3-a]quinoxalin-8-yl)pyrimidin-5-yl)oxy)propan-1-amine;
- N,N-dimethyl-3-((5-(1-(tetrahydro-2H-pyran-4-yl)-[1,2,4]triazolo[4,3-a]quinoxalin-8-yl)pyrazin-2-yl)oxy)propan-1-amine;
- N,N-dimethyl-2-(4-(1-(tetrahydro-2H-pyran-4-yl)-[1,2,4]triazolo[4,3-a]quinoxalin-8-yl)phenoxy)ethan-1-amine;
- N-(3-(dimethylamino)propyl)-4-(1-(tetrahydro-2H-pyran-4-yl)-[1,2,4]triazolo[4,3-a]quinoxalin-8-yl)aniline;
- N-(3-(dimethylamino)propyl)-N-methyl-4-(1-(tetrahydro-2H-pyran-4-yl)-[1,2,4]triazolo[4,3-a]quinoxalin-8-yl)aniline;
- N,N-dimethyl-1-(4-(1-(tetrahydro-2H-pyran-4-yl)-[1,2,4]triazolo[4,3-a]quinoxalin-8-yl)phenyl)piperidin-4-amine;
- 8-(4-(4-methylpiperazin-1-yl)phenyl)-1-(tetrahydro-2H-pyran-4-yl)-[1,2,4]triazolo[4,3-a]quinoxaline;
- 1-(tetrahydro-2H-pyran-4-yl)-8-(4-((3S,5R)-3,4,5-trimethylpiperazin-1-yl)phenyl)-[1,2,4]triazolo[4,3-a]quinoxaline;
- N,N-dimethyl-1-(5-(1-(tetrahydro-2H-pyran-4-yl)-[1,2,4]triazolo[4,3-a]quinoxalin-8-yl)pyridin-2-yl)piperidin-4-amine;
- 8-(6-(4-methylpiperazin-1-yl)pyridin-3-yl)-1-(tetrahydro-2H-pyran-4-yl)-[1,2,4]triazolo[4,3-a]quinoxaline;
- 1-(tetrahydro-2H-pyran-4-yl)-8-(6-((3S,5R)-3,4,5-trimethylpiperazin-1-yl)pyridin-3-yl)-[1,2,4]triazolo[4,3-a]quinoxaline;
- N,N-dimethyl-4-(4-(1-(tetrahydro-2H-pyran-4-yl)-[1,2,4]triazolo[4,3-a]quinoxalin-8-yl)phenyl)cyclohexan-1-amine;
- N,N-dimethyl-4-(5-(1-(tetrahydro-2H-pyran-4-yl)-[1,2,4]triazolo[4,3-a]quinoxalin-8-yl)pyridin-2-yl)cyclohexan-1-amine;
- N,N-dimethyl-3-(4-(1-(piperidin-1-yl)-[1,2,4]triazolo[4,3-a]quinoxalin-8-yl)phenoxy)propan-1-amine;
- N,N-dimethyl-3-(4-(1-morpholino-[1,2,4]triazolo[4,3-a]quinoxalin-8-yl)phenoxy)propan-1-amine;
- N,N-dimethyl-3-(4-(1-(4-methylpiperazin-1-yl)-[1,2,4]triazolo[4,3-a]quinoxalin-8-yl)phenoxy)propan-1-amine;
- N,N-dimethyl-3-(4-(1-((3S,5R)-3,4,5-trimethylpiperazin-1-yl)-[1,2,4]triazolo[4,3-a]quinoxalin-8-yl)phenoxy)propan-1-amine;
- N,N-dimethyl-3-((5-(1-morpholino-[1,2,4]triazolo[4,3-a]quinoxalin-8yl)pyridin-2-yl)oxy)propan-1-amine;
- N,N-dimethyl-3-((5-(1-(4-methylpiperazin-1-yl)-[1,2,4]triazolo[4,3-a]quinoxalin-8-yl)pyridin-2-yl)oxy)propan-1-amine;
- N,N-dimethyl-3-((5-(1-((3S,5R)-3,4,5-trimethylpiperazin-1-yl)-[1,2,4]triazolo[4,3-a]quinoxalin-8-yl)pyridin-2-yl)oxy)propan-1-amine;
- N,N-dimethyl-3-(4-(1-(morpholinomethyl)-[1,2,4]triazolo[4,3-a]quinoxalin-8-yl)phenoxy)propan-1-amine;
- 3-(4-(1-(1H-imidazol-1-yl)-[1,2,4]triazolo[4,3-a]quinoxalin-8-yl)phenoxy)-N,N-dimethylpropan-1-amine;
- 3-(4-(1-(1H-imidazol-4-yl)-[1,2,4]triazolo[4,3-a]quinoxalin-8-yl)phenoxy)-N,N-dimethylpropan-1-amine;
- N,N-dimethyl-3-(4-(1-(tetrahydro-2H-pyran-4-yl)imidazo[1,2-a]quinoxalin-8-yl)phenoxy)propan-1-amine;
- N,N-dimethyl-3-(4-(1-(tetrahydro-2H-pyran-4-yl)imidazo[1,5-a]quinoxalin-8-yl)phenoxy)propan-1-amine;
- N,N-dimethyl-3-(4-(1-(tetrahydro-2H-pyran-4-yl)pyrrolo[1,2-a]quinoxalin-8-yl)phenoxy)propan-1-amine;
- 8-phenyl-1-(tetrahydro-2H-pyran-4-yl)-[1,2,4]triazolo[4,3-a]quinoxaline;
- N,N,N-trimethyl-3-((4-(1-(tetrahydro-2H-pyran-4-yl)-[1,2,4]triazolo[4,3-a]quinoxalin-8-yl)phenyl)amino)propan-1-aminium;
- 1-(4-(1-(tetrahydro-2H-pyran-4-yl)-[1,2,4]triazolo[4,3-a]quinoxalin-8-yl)phenyl)piperidin-4-amine;
- N-methyl-1-(4-(1-(tetrahydro-2H-pyran-4-yl)-[1,2,4]triazolo[4,3-a]quinoxalin-8-yl)phenyl)piperidin-4-amine;
- N-ethyl-1-(4-(1-(tetrahydro-2H-pyran-4-yl)-[1,2,4]triazolo[4,3-a]quinoxalin-8-yl)phenyl)piperidin-4-amine;
- 1-(2-fluoro-4-(1-(tetrahydro-2H-pyran-4-yl)-[1,2,4]triazolo[4,3-a]quinoxalin-8-yl)phenyl)-N,N-dimethylpiperidin-4-amine;
- 1-(2-chloro-4-(1-(tetrahydro-2H-pyran-4-yl)-[1,2,4]triazolo[4,3-a]quinoxalin-8-yl)phenyl)-N,N-dimethylpiperidin-4-amine;

N,N-dimethyl-1-(2-methyl-4-(1-(tetrahydro-2H-pyran-4-yl)-[1,2,4]triazolo[4,3-a]quinoxalin-8-yl)phenyl)piperidin-4-amine;
N,N-dimethyl-1-(4-(1-(tetrahydro-2H-pyran-4-yl)-[1,2,4]triazolo[4,3-a]quinoxalin-8-yl)-2-(trifluoromethyl)phenyl)piperidin-4-amine;
1-(3-fluoro-4-(1-(tetrahydro-2H-pyran-4-yl)-[1,2,4]triazolo[4,3-a]quinoxalin-8-yl)phenyl)-N,N-dimethylpiperidin-4-amine;
1-(3-chloro-4-(1-(tetrahydro-2H-pyran-4-yl)-[1,2,4]triazolo[4,3-a]quinoxalin-8-yl)phenyl)-N,N-dimethylpiperidin-4-amine;
N,N-dimethyl-1-(3-methyl-4-(1-(tetrahydro-2H-pyran-4-yl)-[1,2,4]triazolo[4,3-a]quinoxalin-8-yl)phenyl)piperidin-4-amine;
N,N-dimethyl-1-(4-(1-(tetrahydro-2H-pyran-4-yl)-[1,2,4]triazolo[4,3-a]quinoxalin-8-yl)-3-(trifluoromethyl)phenyl)piperidin-4-amine;
N,N-dimethyl-1-(6-(1-(tetrahydro-2H-pyran-4-yl)-[1,2,4]triazolo[4,3-a]quinoxalin-8-yl)pyridin-3-yl)piperidin-4-amine;
N,N-dimethyl-1-(1-(4-(1-(tetrahydro-2H-pyran-4-yl)-[1,2,4]triazolo[4,3-a]quinoxalin-8-yl)phenyl)piperidin-4-yl)methanamine;
N,N-dimethyl-2-(1-(4-(1-(tetrahydro-2H-pyran-4-yl)-[1,2,4]triazolo[4,3-a]quinoxalin-8-yl)phenyl)piperidin-4-yl)ethan-1-amine;
3-(2-fluoro-4-(1-((3S,5R)-3,4,5-trimethylpiperazin-1-yl)-[1,2,4]triazolo[4,3-a]quinoxalin-8-yl)phenoxy)-N,N-dimethylpropan-1-amine;
3-(2-chloro-4-(1-((3S,5R)-3,4,5-trimethylpiperazin-1-yl)-[1,2,4]triazolo[4,3-a]quinoxalin-8-yl)phenoxy)-N,N-dimethylpropan-1-amine;
N,N-dimethyl-3-(2-(trifluoromethyl)-4-(1-((3S,5R)-3,4,5-trimethylpiperazin-1-yl)-[1,2,4]triazolo[4,3-a]quinoxalin-8-yl)phenoxy)propan-1-amine;
N,N-dimethyl-1-(4-(1-((3S,5R)-3,4,5-trimethylpiperazin-1-yl)-[1,2,4]triazolo[4,3-a]quinoxalin-8-yl)phenyl)piperidin-4-amine;
1-(2-fluoro-4-(1-((3S,5R)-3,4,5-trimethylpiperazin-1-yl)-[1,2,4]triazolo[4,3-a]quinoxalin-8-yl)phenyl)-N,N-dimethylpiperidin-4-amine;
1-(2-chloro-4-(1-((3S,5R)-3,4,5-trimethylpiperazin-1-yl)-[1,2,4]triazolo[4,3-a]quinoxalin-8-yl)phenyl)-N,N-dimethylpiperidin-4-amine;
N,N-dimethyl-1-(2-(trifluoromethyl)-4-(1-((3S,5R)-3,4,5-trimethylpiperazin-1-yl)-[1,2,4]triazolo[4,3-a]quinoxalin-8-yl)phenyl)piperidin-4-amine;
1-(2-fluoro-6-(trifluoromethyl)-4-(1-((3S,5R)-3,4,5-trimethylpiperazin-1-yl)-[1,2,4]triazolo[4,3-a]quinoxalin-8-yl)phenyl)-N,N-dimethylpiperidin-4-amine;
1-(2-chloro-6-(trifluoromethyl)-4-(1-((3S,5R)-3,4,5-trimethylpiperazin-1-yl)-[1,2,4]triazolo[4,3-a]quinoxalin-8-yl)phenyl)-N,N-dimethylpiperidin-4-amine;
1-(4-(1-(4-(dimethylamino)piperidin-1-yl)-[1,2,4]triazolo[4,3-a]quinoxalin-8-yl)phenyl)-N,N-dimethylpiperidin-4-amine;
N,N-dimethyl-1-(4-(1-(morpholinomethyl)-[1,2,4]triazolo[4,3-a]quinoxalin-8-yl)phenyl)piperidin-4-amine;
N-methyl-1-(4-(1-(morpholinomethyl)-[1,2,4]triazolo[4,3-a]quinoxalin-8-yl)phenyl)piperidin-4-amine;
1-(2-fluoro-4-(1-((3S,5R)-3,4,5-trimethylpiperazin-1-yl)-[1,2,4]triazolo[4,3-a]quinoxalin-8-yl)phenyl)-N-methylpiperidin-4-amine;
N-methyl-1-(2-(trifluoromethyl)-4-(1-((3S,5R)-3,4,5-trimethylpiperazin-1-yl)-[1,2,4]triazolo[4,3-a]quinoxalin-8-yl)phenyl)piperidin-4-amine;
N-ethyl-1-(2-fluoro-4-(1-((3S,5R)-3,4,5-trimethylpiperazin-1-yl)-[1,2,4]triazolo[4,3-a]quinoxalin-8-yl)phenyl)piperidin-4-amine;
N-ethyl-1-(2-(trifluoromethyl)-4-(1-((3S,5R)-3,4,5-trimethylpiperazin-1-yl)-[1,2,4]triazolo[4,3-a]quinoxalin-8-yl)phenyl)piperidin-4-amine;
1-(4-(1-((3S,5R)-4-ethyl-3,5-dimethylpiperazin-1-yl)-[1,2,4]triazolo[4,3-a]quinoxalin-8-yl)-2-(trifluoromethyl)phenyl)-N,N-dimethylpiperidin-4-amine;
1-(4-(1-((3S,5R)-4-isopropyl-3,5-dimethylpiperazin-1-yl)-[1,2,4]triazolo[4,3-a]quinoxalin-8-yl)-2-(trifluoromethyl)phenyl)-N,N-dimethylpiperidin-4-amine;
3-(4-(1-((2S,6R)-2,6-dimethylmorpholino)-[1,2,4]triazolo[4,3-a]quinoxalin-8-yl)-2-fluorophenoxy)-N,N-dimethylpropan-1-amine;
3-(2-chloro-4-(1-((2S,6R)-2,6-dimethylmorpholino)-[1,2,4]triazolo[4,3-a]quinoxalin-8-yl)phenoxy)-N,N-dimethylpropan-1-amine;
3-(4-(1-((2S,6R)-2,6-dimethylmorpholino)-[1,2,4]triazolo[4,3-a]quinoxalin-8-yl)-2-(trifluoromethyl)phenoxy)-N,N-dimethylpropan-1-amine;
1-(4-(1-((2S,6R)-2,6-dimethylmorpholino)-[1,2,4]triazolo[4,3-a]quinoxalin-8-yl)phenyl)-N,N-dimethylpiperidin-4-amine;
1-(4-(1-((2S,6R)-2,6-dimethylmorpholino)-[1,2,4]triazolo[4,3-a]quinoxalin-8-yl)-2-fluorophenyl)-N,N-dimethylpiperidin-4-amine;
1-(2-chloro-4-(1-((2S,6R)-2,6-dimethylmorpholino)-[1,2,4]triazolo[4,3-a]quinoxalin-8-yl)phenyl)-N,N-dimethylpiperidin-4-amine;
1-(4-(1-((2S,6R)-2,6-dimethylmorpholino)-[1,2,4]triazolo[4,3-a]quinoxalin-8-yl)-2-(trifluoromethyl)phenyl)-N,N-dimethylpiperidin-4-amine;
1-(4-(1-((2S,6R)-2,6-dimethylmorpholino)-[1,2,4]triazolo[4,3-a]quinoxalin-8-yl)-2-(trifluoromethyl)phenyl)-N-methylpiperidin-4-amine;
1-(4-(1-((2S,6R)-2,6-dimethylmorpholino)-[1,2,4]triazolo[4,3-a]quinoxalin-8-yl)-2-(trifluoromethyl)phenyl)-N-ethylpiperidin-4-amine;
3-(4-(1-((2R,6S)-2,6-dimethyltetrahydro-2H-pyran-4-yl)-[1,2,4]triazolo[4,3-a]quinoxalin-8-yl)-2-(trifluoromethyl)phenoxy)-N,N-dimethylpropan-1-amine;
1-(4-(1-((2R,6S)-2,6-dimethyltetrahydro-2H-pyran-4-yl)-[1,2,4]triazolo[4,3-a]quinoxalin-8-yl)-2-(trifluoromethyl)phenyl)-N,N-dimethylpiperidin-4-amine;
N,N-dimethyl-3-(4-(1-(piperidin-1-yl)-[1,2,4]triazolo[4,3-a]quinoxalin-8-yl)-2-(trifluoromethyl)phenoxy)propan-1-amine;
1-(2-fluoro-4-(1-(piperidin-1-yl)-[1,2,4]triazolo[4,3-a]quinoxalin-8-yl)phenyl)-N,N-dimethylpiperidin-4-amine;
1-(2-chloro-4-(1-(piperidin-1-yl)-[1,2,4]triazolo[4,3-a]quinoxalin-8-yl)phenyl)-N,N-dimethylpiperidin-4-amine;
N,N-dimethyl-1-(4-(1-(piperidin-1-yl)-[1,2,4]triazolo[4,3-a]quinoxalin-8-yl)-2-(trifluoromethyl)phenyl)piperidin-4-amine;
3-(4-(1-((3R,5S)-3,5-dimethylpiperidin-1-yl)-[1,2,4]triazolo[4,3-a]quinoxalin-8-yl)-2-(trifluoromethyl)phenoxy)-N,N-dimethylpropan-1-amine;
1-(4-(1-((3R,5S)-3,5-dimethylpiperidin-1-yl)-[1,2,4]triazolo[4,3-a]quinoxalin-8-yl)-2-(trifluoromethyl)phenyl)-N,N-dimethylpiperidin-4-amine;
3-(2-bromo-4-(1-((3S,5R)-3,4,5-trimethylpiperazin-1-yl)-[1,2,4]triazolo[4,3-a]quinoxalin-8-yl)phenoxy)-N,N-dimethylpropan-1-amine;

3-(3-fluoro-4-(1-((3S,5R)-3,4,5-trimethylpiperazin-1-yl)-[1,2,4]triazolo[4,3-a]quinoxalin-8-yl)phenoxy)-N,N-dimethylpropan-1-amine;

3-(2-fluoro-6-(trifluoromethyl)-4-(1-((3S,5R)-3,4,5-trimethylpiperazin-1-yl)-[1,2,4]triazolo[4,3-a]quinoxalin-8-yl)phenoxy)-N,N-dimethylpropan-1-amine;

3-(2-chloro-6-(trifluoromethyl)-4-(1-((3S,5R)-3,4,5-trimethylpiperazin-1-yl)-[1,2,4]triazolo[4,3-a]quinoxalin-8-yl)phenoxy)-N,N-dimethylpropan-1-amine;

3-(2-chloro-3-fluoro-4-(1-((3S,5R)-3,4,5-trimethylpiperazin-1-yl)-[1,2,4]triazolo[4,3-a]quinoxalin-8-yl)phenoxy)-N,N-dimethylpropan-1-amine; and 1-(2-bromo-4-(1-((3S,5R)-3,4,5-trimethylpiperazin-1-yl)-[1,2,4]triazolo[4,3-a]quinoxalin-8-yl)phenyl)-N,N-dimethylpiperidin-4-amine.

* * * * *